(12) United States Patent
DiMaio et al.

(10) Patent No.: US 11,259,870 B2
(45) Date of Patent: Mar. 1, 2022

(54) INTERACTIVE USER INTERFACES FOR MINIMALLY INVASIVE TELESURGICAL SYSTEMS

(71) Applicants: Intuitive Surgical Operations, Inc., Sunnyvale, CA (US); The Johns Hopkins University, Baltimore, MD (US)

(72) Inventors: Simon P. DiMaio, San Carlos, CA (US); Christopher J. Hasser, Los Altos, CA (US); Russell H. Taylor, Severna Park, MD (US); David Q. Larkin, Menlo Park, CA (US); Peter Kazanzides, Towson, MD (US); Anton Deguet, Baltimore, MD (US); Balazs Peter Vagvolgyi, Baltimore, MD (US); Joshua Leven, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 859 days.

(21) Appl. No.: 15/725,271

(22) Filed: Oct. 4, 2017

(65) Prior Publication Data
US 2018/0042680 A1 Feb. 15, 2018

Related U.S. Application Data

(60) Division of application No. 13/775,574, filed on Feb. 25, 2013, now Pat. No. 9,795,446, which is a
(Continued)

(51) Int. Cl.
*A61B 1/00* (2006.01)
*A61B 34/10* (2016.01)
(Continued)

(52) U.S. Cl.
CPC .......... *A61B 34/10* (2016.02); *A61B 1/00193* (2013.01); *A61B 8/12* (2013.01);
(Continued)

(58) Field of Classification Search
CPC ...... G16H 30/20; G16H 30/40; G06F 3/0325; G06F 3/0346; G06F 8/34; A61B 34/20;
(Continued)

(56) References Cited

U.S. PATENT DOCUMENTS

| | | | |
|---|---|---|---|
| 4,642,687 A | 2/1987 | Wedgwood et al. | |
| 4,672,963 A | 6/1987 | Barken | |

(Continued)

FOREIGN PATENT DOCUMENTS

| | | |
|---|---|---|
| DE | 10015826 A1 | 10/2001 |
| EP | 514584 A2 | 11/1992 |

(Continued)

OTHER PUBLICATIONS

3D Slicer, http://slicer.org/welcome.html, downloaded Oct. 25, 2006, p. 1; and Introduction, http:/slicer.org/intro/index.html, downloaded Oct. 25, 2006, pp. 1-4.
(Continued)

*Primary Examiner* — Alexandra L Newton
(74) *Attorney, Agent, or Firm* — Alford Law Group, Inc.; Vy H. Vu; William E. Alford

(57) ABSTRACT

In one embodiment of the invention, a a minimally invasive surgical system is disclosed. The system configured to capture and display camera images of a surgical site on at least one display device at a surgeon console; switch out of a following mode and into a masters-as-mice (MaM) mode; overlay a graphical user interface (GUI) including an interactive graphical object onto the camera images; and render a pointer within the camera images for user interactive control. In the following mode, the input devices of the
(Continued)

surgeon console may couple motion into surgical instruments. In the MaM mode, the input devices interact with the GUI and interactive graphical objects. The pointer is manipulated in three dimensions by input devices having at least three degrees of freedom. Interactive graphical objects are related to physical objects in the surgical site or a function thereof and are manipulatable by the input devices.

9 Claims, 37 Drawing Sheets

Related U.S. Application Data continuation of application No. 12/189,615, filed on Aug. 11, 2008, now Pat. No. 8,398,541, which is a continuation-in-part of application No. 11/447,668, filed on Jun. 6, 2006, now abandoned.

(60) Provisional application No. 60/954,869, filed on Aug. 9, 2007, provisional application No. 60/688,013, filed on Jun. 6, 2005.

(51) Int. Cl.
| | | |
|---|---|---|
| *A61B 8/12* | (2006.01) | |
| *A61B 8/00* | (2006.01) | |
| *A61B 34/00* | (2016.01) | |
| *A61B 34/37* | (2016.01) | |
| *A61B 34/30* | (2016.01) | |
| *A61B 17/00* | (2006.01) | |
| *A61B 90/00* | (2016.01) | |

(52) U.S. Cl.
CPC ............ *A61B 8/4245* (2013.01); *A61B 34/30* (2016.02); *A61B 34/37* (2016.02); *A61B 34/70* (2016.02); *A61B 34/71* (2016.02); *A61B 34/76* (2016.02); *A61B 8/00* (2013.01); *A61B 34/25* (2016.02); *A61B 90/361* (2016.02); *A61B 2017/00203* (2013.01); *A61B 2090/365* (2016.02); *A61B 2090/378* (2016.02)

(58) Field of Classification Search
CPC ......... A61B 34/25; A61B 34/30; A61B 34/37; A61B 1/00039; A61B 2090/365; A61B 34/35; A61B 1/00002; A61B 1/00004; A61B 1/00006; A61B 1/00009; A61B 1/00045

See application file for complete search history.

(56) References Cited

U.S. PATENT DOCUMENTS

| | | | |
|---|---|---|---|
| 5,279,309 A | 1/1994 | Taylor et al. | |
| 5,397,323 A | 3/1995 | Taylor et al. | |
| 5,408,409 A | 4/1995 | Glassman et al. | |
| 5,417,210 A | 5/1995 | Funda et al. | |
| 5,482,029 A | 1/1996 | Sekiguchi et al. | |
| 5,493,595 A | 2/1996 | Schoolman | |
| 5,551,432 A | 9/1996 | Iezzi | |
| 5,572,999 A | 11/1996 | Funda et al. | |
| 5,601,549 A | 2/1997 | Miyagi | |
| 5,749,362 A | 5/1998 | Funda et al. | |
| 5,759,153 A | 6/1998 | Webler et al. | |
| 5,765,561 A | 6/1998 | Chen et al. | |
| 5,788,688 A | 8/1998 | Bauer et al. | |
| 5,797,849 A | 8/1998 | Vesely et al. | |
| 5,797,900 A | 8/1998 | Madhani et al. | |
| 5,808,665 A | 9/1998 | Green et al. | |
| 5,810,007 A | 9/1998 | Holupka et al. | |
| 5,810,008 A | 9/1998 | Dekel et al. | |
| 5,817,022 A | 10/1998 | Vesely | |
| 5,823,958 A | 10/1998 | Truppe | |
| 5,836,880 A | 11/1998 | Pratt | |
| 5,842,473 A | 12/1998 | Fenster et al. | |
| 5,842,993 A | 12/1998 | Eichelberger et al. | |
| 5,851,183 A | 12/1998 | Bucholz | |
| 5,853,367 A | 12/1998 | Chalek et al. | |
| 5,876,325 A | 3/1999 | Mizuno et al. | |
| 5,887,121 A | 3/1999 | Funda et al. | |
| 6,019,724 A | 2/2000 | Gronningsaeter et al. | |
| 6,129,670 A | 10/2000 | Burdette et al. | |
| 6,167,297 A | 12/2000 | Benaron | |
| 6,201,984 B1 | 3/2001 | Funda et al. | |
| 6,226,566 B1 | 5/2001 | Funda et al. | |
| 6,241,725 B1 | 6/2001 | Cosman | |
| 6,256,529 B1 | 7/2001 | Holupka et al. | |
| 6,325,758 B1 | 12/2001 | Carol et al. | |
| 6,402,737 B1 | 6/2002 | Tajima et al. | |
| 6,425,865 B1 | 7/2002 | Salcudean et al. | |
| 6,440,072 B1 | 8/2002 | Schuman et al. | |
| 6,459,926 B1 | 10/2002 | Nowlin et al. | |
| 6,468,212 B1* | 10/2002 | Scott ...................... | A61B 8/00 600/437 |
| 6,493,608 B1 | 12/2002 | Niemeyer | |
| 6,505,063 B2 | 1/2003 | Van Den Brink et al. | |
| 6,522,906 B1 | 2/2003 | Salisbury, Jr. et al. | |
| 6,547,782 B1 | 4/2003 | Taylor | |
| 6,599,247 B1 | 7/2003 | Stetten | |
| 6,602,185 B1 | 8/2003 | Uchikubo | |
| 6,642,836 B1 | 11/2003 | Wang et al. | |
| 6,659,939 B2* | 12/2003 | Moll ...................... | A61B 34/37 600/102 |
| 6,714,839 B2 | 3/2004 | Salisbury et al. | |
| 6,725,080 B2 | 4/2004 | Melkent et al. | |
| 6,799,065 B1 | 9/2004 | Niemeyer | |
| 6,819,785 B1 | 11/2004 | Vining et al. | |
| 6,837,883 B2 | 1/2005 | Moll et al. | |
| 6,918,876 B1 | 7/2005 | Kamiyama | |
| 6,961,405 B2 | 11/2005 | Scherch | |
| 6,968,224 B2 | 11/2005 | Kessman et al. | |
| 7,103,399 B2 | 9/2006 | Miga et al. | |
| 7,107,090 B2 | 9/2006 | Salisbury et al. | |
| 7,107,124 B2 | 9/2006 | Green | |
| 7,144,367 B2 | 12/2006 | Chen et al. | |
| 7,155,042 B1 | 12/2006 | Cowan et al. | |
| 7,155,316 B2 | 12/2006 | Sutherland et al. | |
| 7,319,897 B2 | 1/2008 | Leitner et al. | |
| 7,413,565 B2 | 8/2008 | Wang et al. | |
| 7,522,953 B2 | 4/2009 | Kaula et al. | |
| 7,831,292 B2 | 11/2010 | Quaid et al. | |
| 7,835,785 B2 | 11/2010 | Scully et al. | |
| 7,881,770 B2 | 2/2011 | Melkent et al. | |
| 8,152,756 B2 | 4/2012 | Webster et al. | |
| 8,155,479 B2 | 4/2012 | Hoffman et al. | |
| 8,206,299 B2 | 6/2012 | Foley et al. | |
| 8,267,853 B2 | 9/2012 | Fisher et al. | |
| 8,398,541 B2 | 3/2013 | Dimaio et al. | |
| 8,700,123 B2 | 4/2014 | Okamura et al. | |
| 9,101,397 B2 | 8/2015 | Guthart et al. | |
| 9,603,508 B2 | 3/2017 | Hale et al. | |
| 9,718,190 B2 | 8/2017 | Larkin et al. | |
| 9,795,446 B2 | 10/2017 | Dimaio et al. | |
| 2001/0037064 A1 | 11/2001 | Shahidi | |
| 2002/0193800 A1 | 12/2002 | Kienzle, III | |
| 2003/0176778 A1* | 9/2003 | Messing ................ | A61B 18/00 600/374 |
| 2004/0143181 A1 | 7/2004 | Damasco et al. | |
| 2004/0201752 A1 | 10/2004 | Parulski et al. | |
| 2005/0085718 A1 | 4/2005 | Shahidi | |
| 2005/0187432 A1* | 8/2005 | Hale ...................... | A61B 1/00183 600/117 |
| 2005/0187472 A1 | 8/2005 | Lysyansky et al. | |
| 2005/0267359 A1 | 12/2005 | Hussaini et al. | |
| 2005/0281444 A1 | 12/2005 | Lundberg et al. | |
| 2006/0041180 A1 | 2/2006 | Viswanathan et al. | |
| 2006/0058988 A1 | 3/2006 | Defranoux et al. | |
| 2006/0258938 A1 | 11/2006 | Hoffman et al. | |
| 2007/0021738 A1 | 1/2007 | Hasser et al. | |
| 2015/0065793 A1 | 3/2015 | Diolaiti et al. | |

(56) References Cited

U.S. PATENT DOCUMENTS

| | | | |
|---|---|---|---|
| 2017/0128041 | A1 | 5/2017 | Hasser et al. |
| 2017/0128144 | A1 | 5/2017 | Hasser et al. |
| 2017/0128145 | A1 | 5/2017 | Hasser et al. |

FOREIGN PATENT DOCUMENTS

| | | | |
|---|---|---|---|
| EP | 0732082 | B1 | 9/2002 |
| EP | 1310844 | A1 | 5/2003 |
| EP | 1424173 | A2 | 6/2004 |
| JP | H06110543 | A | 4/1994 |
| JP | H07184923 | A | 7/1995 |
| JP | H0819975 | A | 1/1996 |
| JP | H08215211 | A | 8/1996 |
| JP | H08299363 | A | 11/1996 |
| JP | H10146341 | A | 6/1998 |
| JP | 2000500679 | A | 1/2000 |
| JP | 2001000448 | A | 1/2001 |
| JP | 2002287613 | A | 10/2002 |
| JP | 2003053684 | A | 2/2003 |
| JP | 2003339725 | A | 12/2003 |
| JP | 2004105638 | A | 4/2004 |
| JP | 2004223128 | A | 8/2004 |
| JP | 2005110878 | A | 4/2005 |
| JP | 2005303327 | A | 10/2005 |
| JP | 2005334650 | A | 12/2005 |
| JP | 2007508913 | A | 4/2007 |
| JP | 2007531553 | A | 11/2007 |
| WO | WO-2005039391 | A2 | 5/2005 |
| WO | WO-2005043319 | A2 | 5/2005 |

OTHER PUBLICATIONS

Abolmaesumi, Purang et al., "A User Interface for Robot-Assisted Diagnostic Ultrasound," IEEE Robotics and Automation Conference, 2001, pp. 1549-1554, vol. 2, IEEE.

Abolmaesumi, Purang et al., "Image Guided Control of a Robot for Medical Ultrasound," IEEE Transactions on Robotics and Automation, 2002, pp. 11-23, vol. 18—Issue 1, IEEE.

Ahlering, Thomas. E. et al., "Robotic radical prostatectomy: a technique to reduce pT2 positive margins," Urology, 2004, pp. 1224-1228, vol. 64 Issue 6, Elsevier Inc.

Arun, K.S. et al., "Least-Squares Fitting of Two 3-D Point Sets," IEEE Transactions on Pattern Analysis and Machine Intelligence (PAMI), vol. 9, No. 5, pp. 698-700, Sep. 1987.

Azuma, Ronald T., "A Survey of Augmented Reality," Teleoperators and Virtual Environments, 1997, pp. 355-385, vol. 6—No. 4.

Bajura, Michael et al., "Merging Virtual Objects with the Real World: Seeing Ultrasound Imagery within the Patient," Computer Graphics, Jul. 26, 1992, pp. 203-210, vol. 26, Issue 2, ACM Press.

Banovac, Filip et al., "Liver Tumor Biopsy in a Respiring Phantom with the Assistance of a Novel Electromagnetic Navigation Device," 2002, pp. 200-207, Springer-Verlag.

Bartels, Richard H. et al., "An Introduction to Splines for use in Computer Graphics and Geometric Modeling," 1987, 6 Pages total , Morgan kaufmann publishers, INC.

Bartels, Richard H. et al., "Solution of the Matrix Equation AX+XB=C," Communications of the ACM, 1972, pp. 820-826, vol. 15—Issue 9, ACM Press.

Berkelman, Peter J. et al., "A Compact Compliant Laparoscopic Endoscope Manipulator," IEEE International Conference on Robotics and Automation, 2002, pp. 1870-1875, vol. 2, IEEE.

Berkelman, Peter J. et al., "A miniature Instrument Tip Force Sensor for Robot/Human Cooperative Micro surgical Manipulation with Enhanced Force Feedback," Proceedings of the Third International Conference on Medical Image Computing and Computer-Assisted Intervention, Springer-Verlag, 2000, pp. 897-906, vol. 1935.

Berkelman, Peter J. et al., "A miniature microsurgical instrument tip force sensor for enhanced force feedback during robot-assisted manipulation," IEEE Transactions on Robotics and Automation, 2000, pp. 917-922, vol. 19—Issue 5, IEEE.

Berkelman, Peter J. et al., "Performance Evaluation of a Cooperative Manipulation Microsurgical Assistant Robot Applied to Stapedotomy," Medical Image Computing and Computer-Assisted Interventions, Lecture Notes in Computer Science, 2001, pp. 1426-1429, vol. 2208.

Besl, Paul J. et al., "A Method for Registration of 3-D Shapes," IEEE Transactions on Pattern Analysis and Machine Intelligence (PAMI), vol. 14, Issue 2, pp. 239-256, Feb. 1992.

Bettini , A. et al., "Vision Assisted Control for Manipulation Using Virtual Fixtures: Experiments at Macro and Micro Scales," IEEE Conference on Robots and Automation (ICRA '02), May 11-15, 2002, pp. 3354-3361, vol. 4, IEEE.

Bettini , A. et al., "Vision Assisted Control for Manipulation Using Virtual Fixtures," IEEE/RSJ International Conference on Intelligent Robots and Systems (IROS), Oct. 29-Nov. 3, 2001, pp. 1171-1176, vol. 2.

Bettini, Alessandro et al., "Vision Assisted Control for Manipulation Using Virtual Fixtures," IEEE Transactions on Robotics, 2004, pp. 953-966, vol. 20—Issue 6, IEEE.

Birkett, Desmond H., "Three-Dimensional Video Imaging Systems," Chapter 1 in Primer of Robotic & Telerobotic Surgery, Eds. Garth H. Ballantyne et al., Pub. by Lippincott Williams & Wilkins, Philadelphia, 2004, pp. 7-11.

Boctor, Emad et al., "A Novel Closed Form Solution for Ultrasound Calibration," IEEE International Symposium on Biomedical Imaging (ISBI), Arlington, VA, vol. 1, pp. 527-530, Apr. 15-18, 2004.

Boctor, Emad, M. et al., "A dual-armed robotic system for intraoperative ultrasound guided hepatic ablative therapy: a prospective study," Proc of IEEE 2004 International Conference on Robotics & Automation, 2004, pp. 2517-2522, vol. 3, IEEE.

Boctor, Emad, M. et al., "A Rapid calibration method for registration and 3D tracking of ultrasound images using spatial localizer," Ultrasonic Imaging and Signal Processing, 2003, pp. 521-532, vol. 5035, SPIE.

Boctor, Emad, M. et al., "CISUS: An integrated 3D ultrasound system for IGT using a modular tracking API," Proceedings of the SPIE, 2004, pp. 247-256, vol. 5367, SPIE.

Boctor, Emad, M. et al., "Development of a Robotically-Assisted 3-D Ultrasound System for Radiofrequency Ablation of Liver Tumors," 6th World Congress of the Hepato-Pancreato-Biliary Association, Abstract No. 167, 2004, pp. 46, vol. 6—Supplement 1, Taylor & Francis Health Science.

Boctor, Emad, M. et al., "PC Based system for calibration, Reconstruction Processing and Visualization of 3D Ultrasound Data Based on a Magnetic-Field Position and Orientation Sensing System," Proceedings of the International Conference on Computational Science—Part II, Lecture Notes in Computer Science , 2001, pp. 13-22, vol. 2074, Springer.

Boctor, Emad, M. et al., "Robot-assisted 3D strain imaging for monitoring thermal ablation of liver," Annual congress of the Society of American Gastrointestinal Endoscopic Surgeons (SAGES),Emerging Technology Lunch Poster TP004, 2005, pp. 240-241.

Boctor, Emad, M. et al., "Robotic Strain Imaging for Monitoring Thermal Ablation of Liver," Medical Image Computing and Computer-Assisted Intervention MICCAI, 2004, pp. 81-88, vol. 2, Springer-Verlag.

Boctor, Emad, M. et al., "Robotically assisted intraoperative ultrasound with application to ablative therapy of liver cancer," Medical Imaging:Visualization, Image Guided Procedures, and Display, 2003, pp. 281-291, vol. 5029, SPIE.

Boctor, Emad, M. et al., "Tracked 3D ultrasound in radio-frequency liver ablation," in Medical Imaging 2003:Ultrasonic Imaging and Signal Processing, 2003, pp. 174-182, vol. 5035, SPIE.

Boudet,Sylvie et al., "An Integrated Robotics and Medical Control Device to Quantify Atheromatous Plaques: Experiments on the Arteries of a Patient," Proc of IEE/RSH International Conference on Intelligent Robots and Systems, 1997, pp. 1533-1538, vol. 3.

Brown, Myron M. et al., "Advances in Computational Stereo," IEEE Transactions on Pattern Analysis and Machine Intelligence (PAMI), 2003, pp. 993-1008, vol. 25 Issue, IEEE.

(56) References Cited

OTHER PUBLICATIONS

Burschka, Darius et al., "Scale-Invariant Registration of Monocular Endoscopic Images to CT-Scans for Sinus Surgery," Med Image Anal, 2004, pp. 413-421, vol. 2, Springer-Verlag.
Burschka, Darius et al., "Scale-Invariant Registration of Monocular Stereo Images to 3D Surface Models," IEEE Int. Conf. on Robots and Systems, 2004, pp. 2581-2586, vol. 3, IEEE.
Burschka, Darius et al., "Navigating Inner Space: 3-D Assistance for Minimally Invasive Surgery," Robotics and Autonomous Systems, 2005, pp. 5-26, vol. 52—Issue 1, Elsevier.
Burschka, Darius et al., "Principle and Practice of Real-Time Visual Tracking for Navigation and Mapping," IEEE Workshop on Robotic Sensing: Robotics in the Automotive Industry, 2004, pp. 1-8, IEEE.
Bzostek, Andrew, "Computer-Integrated needle therapy systems: Implementation and Analysis," Computer Science, 2005, 379 pages.
Bzostek, Andrew et al., "A Testbed System for Robotically Assisted Percutaneous Pattern Therapy," Medical Image Computing and Computer-Assisted Surgery, Lecture Notes In Computer Science, 1999, pp. 1098-1107, vol. 1679, Springer.
Bzostek, Andrew et al., "An automated system for precise percutaneous access of the renal collecting system," Proceedings of the First Joint Conference on Computer Vision, Virtual Reality and Robotics in Medicine and Medial Robotics and Computer-Assisted Surgery, Lecture Notes In Computer Science, 1997, pp. 299-308, vol. 1205, Springer-Verlag.
Bzostek, Andrew, "Image Guided Percutaneous Pattern Placement in Soft Tissue," The Johns Hopkins University Dept. of Computer Science: Baltimore, 1997, pp. Jan. 22, 2007.
Cadeddu, Jeffrey A. et al., "A Robotic System for Percutaneous Renal Access," The Journal of Urology, 1997, pp. 1589-1593, vol. 158—Issue 4.
Cadeddu, Jeffrey et al., "A robotic system for percutaneous renal access incorporating a remote center of motion design," Journal of Endourolog, 1998, S237, vol. 12.
Cannon, Jeremy W. et al., "Real-time three-dimensional ultrasound for guiding surgical tasks," Computer Aided Surgery, 2003, pp. 82-90, vol. 8—No. 2, John Wiley & Sons.
Carr, J., "Surface reconstruction in 3D medical imaging," PhD Thesis, Part 1, University of Canterbury, Christchurch, New Zealand, 1996, 112 Pages.
Carr, J., "Surface reconstruction in 3D medical imaging," PhD Thesis, Part 2, University of Canterbury, Christchurch, New Zealand, 1996, 112 Pages.
Cash, David M. et al., "Incorporation of a laser range scanner into an image-guided surgical system," The International Society for Optical Engineering (SPIE), Medical Imaging 2003: Visualization, Image-Guided Procedures, and Display; San Diego, CA, Ed. Robert L. Galloway, 2003, pp. 269-280, vol. 5029.
Chang, Jun Keun et al., "Intravascular micro active catheter for minimal invasive surgery," 1st Annual International Conference on Microtechnologies in Medicine and Biology, 2000, pp. 243-246.
Chen, Homer H. "A Screw Motion Approach to Uniqueness Analysis of Head-Eye Geometry," Computer Vision and Pattern Recognition, 1991, pp. 145-151, IEEE.
Chinzei, Kiyoyuki et al., "MR Compatible Surgical Assist Robot: System Integration and Preliminary Feasibility Study," in Proceedings of Third International Conference On Medical Imaging and Computer Assisted Surgery (MICCAI), 2000, pp. 921-930, vol. 1935, Springer-Verlag.
Choti, Michael A. et al., "Trends in Long Term Survival Following Liver Resection for Hepatic Colorectal Metastases," Ana Surg, 2002, pp. 759-766, vol. 235—No. 6, Lippincott Williams & Wilkins.
Choti, Michael A., "Hepatic Radiofrequency Ablation," Cancer Journal, 2000, pp. S291-S292, vol. 6—issue 4, Jones and Bartlett.
Choti, Michael A., "Surgical Management of Hepatocellular Carcinoma: Resection and Ablation," Journal of Vascular and Interventional Radiology, 2002, pp. S197-S203, vol. 13—No. 9.
Chung, Mathew et al., "Laparoscopic Radiofrequency Ablation of Unresectable Hepatic Malignancies," Surg Endosc, 2001, pp. 1020-1026, vol. 15—No. 9, Springer-Verlag.

Cleary, Kevin et al., "State of the Art in Surgical Robotics:Clinical Applications and Technology Challenges," Computer Aided Surgery, 2001 [retrieved on Feb. 24, 2002], pp. 1-26.
Cleary, Kevin et al., "State of the art surgical robotics clinical applications and technology challenges," Computer Aided Surgery, 2001, pp. 312-328, vol. 6; Part 6, John Wiley & Sons.
Cleary,K. et al., "Robotically-assisted spine nerve blocks," Radiology, 2001, 1 page, vol. 221—No. 618,.
D'Angelica M., "Staging Laparoscopy for Potentially Respectable Noncolorectal," Ann Surg Oncol, 2002, pp. 204-209, vol. 9—No. 2, Lippincott Williams & Wilkins.
Daniilidis, Konstantinos, Hand-Eye Calibration Using Dual Quaternions, Int. J. of Robotics Research, 2000, pp. 286-298, vol. 19—No. 3, Sage Publications, Inc.
Davies, Brain L. et al., "A Robotic system for tkr surgery," Proceedings of 3rd Annual North American Program on Computer Assisted Orthopaedic Surgery (CAOS USA), University of Pittsburgh Medical Center, Pittsburgh, Pennsylvania,published in Computer Aided Surgery, Jun. 17-19, 1999, p. 339, vol. 4—Iss. 6.
Davies, S. C.et al., "Ultrasound quantitaion of respiratory organ motion in the upper abdomen," British Journal of Radiology, 1994, pp. 1096-1102, vol. 37—Iss. 803.
De Cunha, D. et al., The MIDSTEP System for Ultrasound guided Remote Telesurgery, Proceedings of the 20th Annual International Conference of the IEEE Engineering in Medicine and Biology Society, 1998, pp. 1266-1269, vol. 3—No. 29, IEEE.
Degoulange, E. et al., "HIPPOCRATE: an intrinsically safe robot for medical applications," IEEE/RSH International Conference on Intelligent Biomedicine, 1998, pp. 959-964, vol. 2, IEEE.
Delgorge, Cecile et al., "A Tele-Operated Mobile Ultrasound Scanner Using a Light-Weight Robo," IEEE Transactions on Information Technology in Biomedicine, 2005, pp. 50-58, vol. 9 No 1, IEEE.
Dewan, Maneesh et al., "Vision-Based Assistance for Ophthalmic Micro-Surgery," Proceedings of Seventh International Conference on Medical Image Computing and Computer-Assisted Intervention (MICCAI), 2004, pp. 49-57, vol. 3217, Springer-Verlag.
Dodds, Zachary et al., "A hierarchical architecture for vision-based robotic manipulation tasks," in Proceedings of the International Conference on Vision Systems, 1999, pp. 312-330, vol. 542, Springer-Verlag.
Doggett, Stephen W., "Image Registered Real Time Intra-Operative Treatment Planning: Permanent Seed Brachytherapy," 2000, pp. 4.
Eldridge, B. et al., "A Remote Center of Motion Robotic Arm for Computer Assisted Surgery," Robotica, 1996, pp. 103-109, vol. 14 Issue 1.
Ellsmere, James et al., "A navigation system for augmenting laparoscopic ultrasound," Medical Image Computing and Computer-Assisted Intervention, Lecture Notes in Computer Science, 2003, pp. 184-191, Springer.
Extended European Search Report for Application No. 11150207.6, dated Jan. 12, 2015, 6 pages.
Extended European Search Report for Application No. EP11150208, dated Feb. 17, 2014, 5 pages.
Fattal, Lischinsk, "Variational Classification for Visualization of 3D Ultrasound Data," Proceedings of the conference on Visualization, 2001, pp. 403-410, IEEE Computer Society.
Fenster, Aaron, et al., "3-D Ultrasound Imaging:A Review," IEEE Engineering and Medicine and Biology Magazine, Nov.-Dec. 1996, pp. 41-51, vol. 15—Issue 6, IEEE.
Fenster, Aaron, et al., "Three-dimensional ultrasound imaging of the prostate," SPIE International Symposium on Medical Imaging,San Diego, California,Published in SPIE: Medical Physics, Feb. 20-26, 1999, pp. 2-11, vol. 3859, SPIE.
Fichtinger, Gabor et al., "Robotically Assisted Percutaneous Local Therapy and Biopsy," 10th International Conference of Advance Robotics, 2001, pp. 133-151, IEEE.
Fichtinger, Gabor et al., "Transrectal prostate biopsy inside closed MRI scanner with remote actuation under real-time image guidance," Medical Image Computing and Computer-Assisted Intervention, Lecture Notes in Computer Science, 2002, pp. 91-98, vol. 2488, Springer Verlag.

(56) References Cited

OTHER PUBLICATIONS

Fichtinger, Gabor et al., "Surgical CAD/CAM and its application for robotically assisted percutaneous procedures," 30th Applied Imagery Pattern Recognition Workshop (AIPR), 2001, pp. 3-8, IEEE.

Fichtinger, Gabor et al., "System For Robotically Assisted Prostate Biopsy And Therapy With intraOperative CT Guidance," Journal of Academic Radiology, 2002, pp. 60-74, vol. 9 No. 1, Elsevier.

Frantz D.D et al., "Accuracy assessment protocols for electromagnetic tracking systems," Physics in Medicine and Biology, 2003, pp. 2241-2251, Issue 48.

Fuchs, Henry et al., "Augmented Reality Visualization for Laparoscopic Surgery," Medical Image Computing and Computer-Assisted Intervention, 1998, pp. 934-943, vol. 1496, Springer-Verlag.

Funda, Janez, "An experimental user interface for an interactive surgical robot," In 1st International Symposium on Medical Robotics and Computer Assisted Surgery (MRCAS 94), Pittsburgh, 1994, pp. 196-201, 203.

Funda, Janez et al., "Comparison of two manipulator designs for laparoscopic surgery," SPIE International Symposium on Optical Tools for Manufacturing and Advanced Automation, 1994, pp. 172-183, vol. 2351, Telemanipulator and Telepresence Technologies.

Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.

Funda, Janez et al., "Control and evaluation of a 7-axis surgical robot for laparoscopy," IEEE Int. Conf. on Robotics and Automation, 1995, pp. 1477-1484, vol. 2, IEEE.

Funda, Janez et al., "Image-Guided Command and Control of a Surgical Robot," Proc. Medicine Meets Virtual Reality II, 1994, pp. 52-57.

Funda, Janez et al., "Optimal Motion Control for Teleoperated Surgical Robots," Intl. Symp. on Optical Tools for Manuf. & Adv Autom,Telemanipulator Technology and Space Telerobotics, 1993, pp. 211-222, vol. 2057, SPIE.

Garrett, William F. et al., "Real-Time Incremental Visualization of Dynamic Ultrasound Volumes Using Parallel BSP Trees," IEEE Proceedings Visualization, 1996, pp. 235-240, 490, IEEE.

Gee, Andrew et al., "Processing and visualizing three-dimensional ultrasound data," Journal of Radiology, 2004, pp. 186-193, vol. 77.

Gelb, A., et al., Table of Contents for"Applied Optimal Estimation," The Analytic Science Corporation, MIT Press, Cambridge, Massachusetts,1974, 4 pages.

Gennari, G. et al., "Probabilistic data association methods in visual tracking of groups," IEEE Conference on Computer Vision and Pattern Recognition, 2004, pp. I-790-1-797, vol. 1—issue. 27, IEEE.

Gigot, Jean-Francois et al., "Laparoscopic Liver Resection for Malignant Liver Tumors Prelimary Results of a Multicenter European Study," Ann Surg, 2002, pp. 90-97, vol. 236—issue 1.

Gonzales, Adriana Vilchis et al., "A System for Robotic Tele-echography," Medical Image Computing and Computer-Assisted Intervention, 2001, pp. 326-334, vol. 2208, Springer.

Grimson, W. Eric et al., "Automated Registration for Enhanced Reality Visualization in Surgery," 1st International Symposium on Medical Robotic and Computer Assisted Surgery (MRCAS), Pittsburgh, 1994, pp. 82-89.

Grimson, W.E.L., et al., "An automatic registration method for frameless stereotaxy, image guided surgery, and enhanced reality visualization," IEEE Transactions on Medical Imaging, vol. 15, No. 2, Apr. 1996, pp. 129-140.

Hager, Gregory D., "A Modular System for Robust Hand Eye Coordination Using Feedback from Stereo Vision," IEEE Transactions on Robotics and Automation, 1997, pp. 582-595, vol. 13—issue(4), IEEE.

Hager, Gregory D. et al., "Efficient Region Tracking With Parametric Models of Geometry and Illumination," IEEE Transactions on Pattern Analysis and Machine Intelligence, 1998, pp. 1025-1039, vol. 20—issue. 10, IEEE.

Hager Gregory D. et al., "Multiple Kernel Tracking with SSD," Proceedings of the IEEE Conference on Computer Vision and Pattern Recognition (CVPR 2004), 2004, pp. I-790-I-797, vol. 1—issue 27, IEEE.

Hager, Gregory D. et al., "The XVision System: A Portable Substrate for Real Time Vision Applications," 1998, pp. 23-37, vol. 69—issue 1.

Hannaford, Blake et al., "Performance Evaluation of a Six-Axis Generalized Force-Reflecting Teleoperator," IEEE Transactions on Systems, Man, and Cybernetics, 1991, pp. 620-633, vol. 21—No. 3, IEEE.

Harris, S.J. et al., "Experiences with Robotic Systems for Knee Surgery," First Joint Conference of CVRMed and MRCAS. Mar. 19-22, 1997, Grenoble, France; Springer, 1997, pp. 757-766, .

Herline, Alan J. et al., "Image-Guided Surgery: Preliminary Feasibility Studies of Frameless Stereotactic Liver Surgery," Archives of Surgery, 1999, pp. 644-650, vol. 134—No. 6.

Herline, Alan J. et al., "Surface Registration for Use in Interactive," Image-Guided Liver Surgery, Computer Aided Surgery, 2000, pp. 11-17, vol. 5—No. 2.

Herman, Barry C., et al, "Telerobotic surgery creates opportunity for augmented reality surgery," Abstract No. T1F2, Telemedicine Journal and E-Health, vol. 11, Issue 2, p. 203, Apr. 2005.

Herman, Barry C., "On the Role of Three Dimensional Visualization for Surgical Applications in Interactive Human Machine Systems," Masters of Science Thesis in Computer Science, The Johns Hopkins University, Baltimore, 2005, 216 pages.

Hespanha J.P. et al., "What Tasks Can Be Performed with an Uncalibrated Stereo Vision System", International Journal of Computer Vision, 1999, pp. 65-85, vol. 35—issue. (1).

Ho, S. C.et al., "Robot Assisted Knee Surgery," IEEE Engineering in Medicine and Biology Magazine, 1995, pp. 292-300, vol. 14—Iss. 3, IEEE.

Hong, Jae-Sung et al., "A Motion Adaptable Needle Placement Instrument Based on Tumor Specific Ultrasonic Image Segmentation," Fifth International Conference on Medical Image Computing and Computer Assisted Intervention, MICCAI '02, Tokyo, Japan, Jul. 2002, pp. 122-129.

Horn, Berthold K.P., "Closed-form solution of absolute orientation using unit quaternions," Journal of the Optical Society of America A, vol. 4, No. 4, pp. 629-642, Apr. 1987.

Hutchinson, Seth et al., "A Tutorial Visual Servo Control," IEEE Transactions on Robotics and Automation, 1996, pp. 651-670, vol. 12 issue.5, IEEE.

IEEE Systems and Software Engineering—Recommended Practice for Architectural Description of Software-Intensive Systems, IEEE Std 1471-2000, 34 pages, First Edition, Jul. 15, 2007.

Intuitive Surgical, Inc., "Intuitive Surgical daVinci API v5.0 Reference Manual," generated Jul. 17, 2006, 149 pages.

Jain, Ameet Kumar et al., "Understanding Bone Responses in B-mode Ultrasound Images and Automatic Bone Surface Extraction using a BayesianProbabilistic Framework," SPIE Medical Imaging, 2004, pp. 131-142, vol. 5373.

Johns Hopkins University and Intuitive Surgical, Inc., "System Requirements for the Surgical Assistant Workstation," Rev. 2, Jan. 29, 2007, 17 pages.

Joskowicz, Leo et al., "Computers in Imaging and Guided Surgery," Computing in Science and Engineering, 2001, pp. 65-72, vol. 3—Issue: 5, IEEE.

Jurie, Frederic et al., "Hyperplane Approximation for Template Matching," IEEE Transactions on Pattern Analysis and Machine Intelligence(PAMI), 2002, pp. 996-1000, vol. 24—Issue 7, IEEE.

Kane, Robert A., "Intraoperative Ultrasonography, History, Current State of the Art, and Future Directions," J Ultrasound Med, 2004, pp. 1407-1420, vol. 23.

Kaplan, Irving, "Minimizing Rectal and Urinary Complications in Prostate Brachytherapy," Journal of Endourology, 2000, pp. 381-383.

Kapoor, Ankur and Russell H. Taylor, "A constrained optimization approach to virtual fixtures for multi-handed tasks," 2008 International Conference on Robotics and Automation (ICRA 2008), May 19-23, 2008, Pasadena, California, pp. 3401-3406.

(56) References Cited

OTHER PUBLICATIONS

Kapoor, Ankur et al., "Constrained Control for Surgical Assistant Robots," 2006 IEEE International Conference on Robotics and Automation (ICRA 2006), Orlando, Florida, May 15-19, 2006, pp. 231-236.

Kapoor, Ankur et al., "Simple Biomanipulation Tasks with a Steady Hand Cooperative Manipulator," In Proceedings of the Sixth International Conference on Medical Image Computing and Computer Assisted Intervention—MICCAI,, Lecture Notes in Computer Science, 2003, vol. 1, Springer.

Kapoor, Ankur et al., "Suturing in Confined Spaces: Constrained Motion Control of a Hybrid 8-DOF Robot," Proceedings, 12th International Conference on Advanced Robotics, 2005, pp. 452-459.

Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.

Kavoussi, Louis R., "Laparoscopic donor nephrectomy," Kidney International, 2000, pp. 2175-2186, vol. 57.

Kazanzides, Peter et al., "A cooperatively-controlled image guided robot system for skull base surgery," Medicine Meets Virtual Reality 16 (MMVR 16) Conference, Jan. 30-Feb. 1, 2008, Long Beach, California, J.D. Westwood et al., eds., IOS Press, 2008, pp. 198-203.

Kazanzides, Peter et al., "Force Sensing and Control for a Surgical Robot," Int. Conference on Robotics and Automation, May 1992, Nice, France; pp. 612-617, vol. 1, IEEE.

Kazerooni, H., "Human Extenders," ASME J. Dynamic Systems, Measurements and Control, 1993, pp. 281-290, vol. 115 No. 2(B).

Koizumi, Naoshi et al., "Development of Three-Dimensional Endoscopic Ultrasound System with Optical Tracking," Medical Image Computing and Computer-Assisted Intervention—MICCAI '02, Tokyo, 2002, pp. 60-65, vol. 2488, Springer-Verlag.

Koizumi, Norihiro et al., "Continuous Path Controller of Slave Manipulator in Remote Ultrasound Diagnostic System," Int. Conference on Robotics and Automation (ICRA 2002), 2002, pp. 3368-3373, vol. 4, IEEE.

Kon, Ryan et al., "An open-source ultrasound calibration toolkit," Medical Imaging Ultrasonic Imaging and Signal Processing, 2005, pp. 516-523, vol. 5750, SPIE.

Korein James U. et al., "A Configurable System for Automation Programming and Control," IEEE Conf. on Robotics and Automation. San Francisco, 1986, pp. 1871-1877, vol. 3, IEEE.

Kragic D. et al., "Human-Machine Collaborative Systems for Microsurgical Applications," International Symposium on Robotics Research, 2005, pp. 731-741, vol. 24—Issue 9, Sage Publications.

Kruchten, Philippe B., "The 4+1 View Model of Architecture," IEEE Software, vol. 12, Issue 6, pp. 42-50, Nov. 1995.

Krupa, A. et al., "Automatic 3-D Positioning of Surgical Instruments during Laparoscopic Surgery Using Automatic Visual Feedback," Proceedings of the 5th International Conference on Medical Image Computing and Computer-Assisted Intervention-Part , Lecture Notes In Computer Science, 2002, pp. 9-16, vol. 2488, Springer Verlag.

Kumar, Rajesh, "An Augmented Steady Hand System for Precise Micromanipulation," 2001, 109 pages.

Kumar, Rajesh et al., "An Augmentation System for Fine Manipulation," Proceedings of the Third International Conference on Medical Image Computing and Computer-Assisted Intervention, Lecture Notes In Computer Science, 2000, pp. 956-964, vol. 1935, Springer Verlang.

Kumar, Rajesh et al., "Application of Task-Level Augmentation for Cooperative Fine Manipulation Tasks in Surgery," Proceedings of the 4th International Conference on Medical Image Computing and Computer-Assisted Intervention, Lecture Notes In Computer Science, 2001, pp. 1417-1418, vol. 2208, Springer Verlang.

Kumar, Rajesh et al., "Experiments with a Steady Hand Robot in Constrained Compliant Motion and Path Following", 1999, pp. 92-97, IEEE.

Kumar, Rajesh et al., "Preliminary Experiments in Cooperative Human/Robot Force Control for Robot Assisted Microsurgical Manipulation," Conference on Robotics and Automation, 2000, pp. 610-617, vol. 1, IEEE.

Kumar, Rajesh et al., "Preliminary experiments in robot/human microinjection," IEEE/RSJ International Conference on Intelligent Robots and Systems, 2003, pp. 3186-3191, vol. 3, IEEE.

Lacroute, Philippe G., "Fast Volume Rendering Using a Shear-Warp Factorization of the Viewing Transformation PhD Thesis," Computer Science, Stanford, California, 1995, 236 Pages.

Lang, Samuel J., Xvision 2—A Framework for Dynamic Vision. Masters Thesis, Computer Science, Johns Hopkins University, Baltimore, 2001, pp. 1-49.

Lange, Thomas et al., Augmenting Intraoperative 3D Ultrasound with Preoperative Models for Navigation in Liver Surgery, Medical Image Computing and Computer-Assisted Interventions, 2004, pp. 534-541, vol. 3217, Springer Verlag.

Lau, William W. et al., "Stereo-Based Endoscopic Tracking of Cardiac Surface Deformation," Proceedings of Seventh International Conference on Medical Image Computing and Computer-Assisted Intervention (MICCAI), Lecture Notes in Computer Science, 2004, pp. 494-501, vol. 2, Springer Verlag.

Lavonius, Maija I. et al., "Staging of Gastric Cancer: A Study with Spiral Computed Tomography,Ultrasonography, Laparoscopy, and Laparoscopic Ultrasonography," Surgical Laparoscopy, Endoscopy & Percutaneous Techniques, 2002, pp. 77-81, vol. 12—No. 2, Lippincott Williams & Wilkins, Inc.

Lawson, Charles L. et al., "Linear least squares with linear inequality constraints Solving Least Squares Problems," 1974, pp. 158-173, Prentice Hall Inc.

Lee Jr, Fred T. et al., "CT-monitored percutaneous cryoablation in a pig liver model," Radiology, 1999, pp. 687-692, vol. 211(3).

Leven, Joshua, "A Telerobotic Surgical System With Integrated Robot-Assisted Laparoscopic Ultrasound Capability," Thesis for Master of Science in Engineering in Computer Science, The Johns Hopkins University, Baltimore, Maryland, May 2005, 63 pages.

Leven, Joshua et al. "DaVinci Canvas: A Telerobotic Surgical System with Integrated, Robot-Assisted, Laparoscopic Ultrasound Capability," Medical Image Computing and Computer-Assisted Intervention (MICCAI), Lecture Notes in Computer Science, J. Duncan et al. Eds., Palm Spring, Springer Verlag, 2005, vol. 3749, pp. 811-818.

Levoy, Marc, "Display of Surfaces from Volume Data," IEEE Computer Graphics and Applications, 1988, pp. 29-37, vol. 8—Iss. 3, IEEE.

Li, M., "Intelligent Robotic Surgical Assistance for Sinus Surgery," Ph.D. Dissertation, Johns Hopkins University, Baltimore, Aug. 2005, 246 pages.

Li, Ming and Russell H. Taylor, "Spatial Motion Constraints in Medical Robots Using Virtual Fixtures Generated by Anatomy," IEEE International Conference on Robotics and Automation, New Orleans, Apr. 2004, pp. 1270-1275.

Li, Ming and Russell H. Taylor, "Performance of surgical robots with automatically generated spatial virtual fixtures," IEEE International Conference on Robotics and Automation, Barcelona, Spain, Apr. 2005, pp. 217-222.

Li, Ming et al, "A Constrained Optimization Approach to Virtual Fixtures," IEEE/RSJ International Conference on Intelligent Robots and Systems (IROS 2005), Edmonton, Alberta, Canada, Aug. 2-6, 2005, pp. 1408-1413.

Li, Ming et al., "Optimal Robot Control for 3D Virtual Fixture inConstrained ENT Surgery," Proceedings of the Sixth International Conference on Medical Image Computing and Computer Assisted Intervention—MICCAI, Lecture Notes in Computer Science, 2003, pp. 165-172, vol. I, Springer Verlag.

Li, Ming et al., "Recognition of Operator Motions for Real-Time Assistance using Virtual Fixtures," IEEE, Haptics 2003, 11th Symposium on Haptic Interfaces for Virtual Environment and Teleoperator Systems, Mar. 22-23, 2003, pp. 125-131, IEEE.

Loser, Michael H. et al., "A New Robotic System for Visually Controlled Percutaneous Interventions under CT Fluoroscopy,"

(56) References Cited

OTHER PUBLICATIONS

Medical Image Computing and Computer-Assisted Interventions,Lecture Notes in Computer Science, 2000, pp. 887-896, vol. 1935, Springer Verlag.

Loser, Michael H. et al., "Visual servoing for automatic and uncalibrated percutaneous procedures," SPIE Medical Imaging, 2000, pp. 270-281, vol. 3976, SPIE.

Maehara, S. et al., "Laparoscopy-Assisted Hepatectomy Using the Endoclose," Surg Endosc, 2002, pp. 1362-1365, vol. 16(9), Springer Verlag.

Maier, Georg, E. et al., "A Dynamically Configurable General Purpose Automation Controller," Proceedings of IFAC/IFIP Symp. on Software for Computer Control, 1986, pp. 47-52, Pergamon Press.

Mala, T. et al., "A Comparative Study of the Short-Term Outcome Following Open and Laparoscopic Liver Resection of Colorectal Metastases," Surg Endosc, 2002, pp. 1059-1063, vol. 16(7), Springer Verlag.

Marayong, Panadda et al., "Spatial Motion Constraints: Theory and Demonstrations for Robot Guidance Using Virtual Fixtures," IEEE International Conference on Robotics and Automation Robotics and Automation, 2003, pp. 1954-1959, vol. 2, No. 14-19, IEEE.

Marescaux, Jadques and Francesco Rubino, "Virtual Operative Fields for Surgical Simulation," Chapter 4 in Primer of Robotic & Telerobotic Surgery, Eds. Garth H. Ballantyne et al., Pub. by Lippincott Williams & Wilkins, Philadelphia, 2004, pp. 26-31.

Masamune K., et al., "Development of a MRI Compatible Needle Insertion Manipulator for Stereotactic Neurosurgery," Journal of Image Guided Surgery, 1995, vol. 1, pp. 242-248.

Masamune, Ken et al., "Development of a MRI Compatible Needle Insertion Manipulator for Stereotactic Neurosurgery," Image Guid Surg, 1995, pp. 165-172.

Masamune Ken et al., "Development of CT-PAKY frame system—CT image guided needle puncturing manipulator and a single slice registration for urological surgery," Proc. 8th annual meeting of Japanese Society for Computer Aided Surgery (JSCAS), 1999, pp. 89-90.

Masamune, Ken et al., "System for Robotically Assisted Percutaneous Procedures With Computed Tomography Guidance," Journal of Computer-Assisted Surgery, 2001, pp. 370-383, vol. 6—No. 6, Wiley-Liss, Inc.

Masamune, Ken H. et al., "A Newly Developed Stereotactic Robot with Detachable Drive for Neurosurgery," 1st International Conference on Medical Image Computing and Computer-Assisted Intervention—MICCAI,Cambridge, Massachusetts; Springer, Oct. 11-13, 1998, pp. 215-222, vol. 1496.

Mayer, Hermann et al., "Skill Transfer and Learning by Demonstration in a Realistic Scenario of Laparoscopic Surgery," International Conference on Humanoids, 2003, 17 pages, IEEE.

Mayer, Hermann et al., "The Endo [PA]R System for Minimally Invasive Robotic Surgery," IEEE/RSJ International Conference on Intelligent Robots and Systems (IROS), 2004, pp. 3637-3642, vol. 4, IEEE.

Megali, Giusepp et al., "A Computer-Assisted Robotic Ultrasound-Guided Biopsy System for Video-Assisted Surgery," Proceedings of the 4th International Conference on Medical Image Computing and Computer-Assisted Intervention, Lecture Notes in Computer Science, 2001, pp. 343-350, vol. 2208, Springer-Verlag.

Menack, M. et al., "Staging of pancreatic and ampullary cancers for resectability using laparoscopy with laparoscopic ultrasound," Surg Endosc, 2001, pp. 1129-1134, vol. 15—No. 10, Springer-Verlag.

Menon, Mani, "Vattikuti Institute prostatectomy, a technique of robotic radical prostatectomy for management of localized carcinoma of the prostate: experience of over 1100 cases," Urol Clin N Am, 2004, pp. 701-717, vol. 31.

Merola, Stephen et al., "Comparison of Laparoscopic Colectomy With and Without the Aid of a Robotic Camera Holder," Surg Laparosc Endosc Percutan Tech, 2002, pp. 45-61, vol. 12—No. 1, Lippincott Williams & Wilkins, Inc.

Migga, Michael I. et al., "Intraoperative Registration of the Liver for Image-Guided Surgery System," The International Society for Optical Engineering (SPIE), Medical Imaging 2003: Visualization, Image-Guided Procedures, and Display; San Diego, CA, Ed. Robert L. Galloway, 2003, pp. 350-359, vol. 5029.

Mitsuishi, Mamoru et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.

Mitsuishi, Mamoru et al., "Remote Ultrasound Diagnostic System," Conf. on Robotics and Automation, 2001, pp. 1567-1574, vol. 2, IEEE.

Mourgues, Fabienet al., "Flexible Calibrations of Actuated Stereoscopic Endoscope for Overlay in Robot Assisted Surgery," Proceedings of the 5th International Conference on Medical Image Computing and Computer-Assisted Intervention—Part I, Lecture Notes In Computer Science, 2002, pp. 25-34, vol. 2488, Springer-Verlag.

Muratore, Diane M. et al., "Beam Calibration Without a Phantom for Creating a 3D Free-hand Ultrasound System," Ultrasound in Medicine and Biology, 2001, pp. 1557-1566, vol. 27—No. 11, Elsevier.

Nakakura, Eric K et al., "Hepatocellular Carcinoma: Current Management Recommendations," Advances on Oncology, 2000, pp. 12-18, vol. 16—No. 2.

Nelson, Thomas R. et al., "Interactive Acquisition, Analysis, and Visualization of Sonographic Volume Data," International Journal of Imaging Systems and Technology, 1997, pp. 26-37, vol. 8, John Wiley & Sons, Inc.

Nelson, Thomas, R. et al., "Three-dimensional ultrasound imaging," Ultrasound in Medicine & Biology, 1998, pp. 1243-1270, vol. 24—No. 9, Elsevier.

Novotny Paul M. et al., "Tool Localization in 3D Ultrasound Images," Medical Image Computing and Computer-Assisted Intervention, 2003, pp. 969-970, vol. 2879, Springer.

Office Action dated Jan. 5, 2009 for European Application No. 20060784595 filed Jun. 5, 2006, 2 pages.

Office Action dated Jan. 12, 2012 for Japanese Application No. 20080515812 filed Jun. 5, 2005, 5 pages.

Office Action dated Feb. 13, 2015 for Japanese Application No. 20140086093 filed Apr. 18, 2014, 1 page.

Office Action dated Mar. 16, 2015 for Japanese Application No. 20110272384 filed Dec. 13, 2011, 22 pages.

Office Action dated Jun. 19, 2014 for Japanese Application No. 20110272384 filed Dec. 13, 2011, 3 pages.

Office Action dated Nov. 19, 2013 for Chinese Application No. 2006820112 filed Jun. 5, 2006, 9 pages.

Office Action dated Jun. 20, 2013 for Japanese Application No. 20110272385 filed Dec. 13, 2011, 5 pages.

Office Action dated Jun. 20, 2013 for Japanese Application No. 20110272386 filed Dec. 13, 2011, 8 pages.

Office Action dated Jun. 20, 2013 for Japanese Application No. JP20110272384 filed Dec. 13, 2011, 7 pages.

Office Action dated Dec. 27, 2013 for Japanese Application No. 20110272384 filed Dec. 13, 2011, 5 pages.

Office Action dated Dec. 27, 2013 for Japanese Application No. 20110272386 filed Dec. 13, 2011, 8 pages.

Office Action dated Feb. 27, 2015 for Japanese Application No. 20130194017 filed Sep. 19, 2013, 4 pages.

Office Action dated Aug. 28, 2015 for Japanese Application No. 20140086093, filed Apr. 18, 2014, 3 page.

Office Action dated Aug. 31, 2011 for Japanese Application No. 20080515812 filed Jun. 5, 2005, 10 pages.

Office Action dated Jul. 31, 2014 for Japanese Application No. 2013-194017 filed Sep. 19, 2013.

Ohbuchi, Ryutarou et al., "Incremental Volume Reconstruction and Rendering for 3D Ultrasound Imaging," The International Society of Optical Engineering, 1992, pp. 312-323, vol. 1808, SPIE.

Park, Shinsuk et al., "Virtual Fixtures for Robotic Cardiac Surgery," Proceedings of the 4th International Conference on Medical Image Computing and Computer-Assisted Intervention, 2001, pp. 1419-1420, vol. 2208, Springer-Verlag.

(56) References Cited

OTHER PUBLICATIONS

Patriciu Alexandru et al., "Motion-based robotic instrument targeting under c-arm fluoroscopy," Medical Image Computing and Computer-Assisted Interventions, 2000, pp. 988-998, vol. 1935, Springer.
PCT/US06/21852 International Search Report dated Nov. 2, 2006, 3 pages.
PCT/US06/21852 Written Opinion of the International Search Authority dated Nov. 2, 2006, 6 pages.
PCT/US06/40754 International Search Report dated Jul. 11, 2007, 4 pages.
PCT/US06/40754 Written Opinion of the International Search Authority dated Apr. 23, 2008, 8 pages.
Podnos, Yale, D. et al., "Laparoscopic Ultrasound with Radiofrequency Ablation in Cirrhotic Patients with Hepatocellular Carcinoma," Am Surg, 2001, pp. 1181-1184, vol. 67—No. 12.
Poulose P. K et al., "Human vs Robotic Organ Retraction During Laparoscopic Nissen Fundoplication," Surgical Endoscopy, 1999, pp. 461-465, vol. 13, Springer-Verlag.
Prager Richard et al., "Practical segmentation of 3D ultrasound," In Proceedings of Medical Image Understanding and Analysis, 1999, pp. 161-164.
Prager Richard et al., "Rapid Calibration for 3D Freehand Ultrasound," Ultrasound in Medicine and Biology, 1998, pp. 855-869, vol. 24—No. 6, Elsevier.
Prasad, Srinivas K. et al., "A minimally invasive approach to pelvic osteolysis," 2002, in Proc. Computer-Assisted Orthopaedic Surgery (CAOS), pp. 349-350.
Prasad Srinivas K. et al., "A Modular 2-DOF Force-Sensing Instrument for Laparoscopic Surgery," Proceedings of the Sixth International Conference on Medical Image Computing and Computer Assisted Intervention—MICCAI,Lecture Notes in Computer Science, 2003, pp. 279-286, vol. I, Springer.
Ramey, N. A., "Stereo-Based Direct Surface Tracking with Deformable Parametric Models," Thesis submitted to The Johns Hopkins University, Maryland, Apr. 2003, 104 pages.
Ramey, Nicholas A. et al., "Evaluation of Registration Techniques in a robotic approach to pelvic osteolysis," International Proceedings of Computer Assisted Orthopaedic Surgery (CAOS), 2004, pp. 26-27.
Rasmussen, Christopher et al., "Joint Probabilistic Techniques for Tracking Multi-Part Objects," Computer Vision and Pattern Recognition, 1998. Proceedings. 1998 IEEE Computer Society Conference on Jun. 23-25, 1998, pp. 16-21.
Rasmussen, Christopher et al., "Probabilistic data association methods for tracking complex visual objects," IEEE Transactions on Pattern Analysis and Machine Intelligence, 2001, pp. 560-576, vol. 23, Issue 6, IEEE.
Ratner, Lloyd E. et al., "Laparoscopic live donor nephrectomy removes disincentives to live donation," Transplantation, 1997, pp. 3402-3403, vol. 29—Issue 8, Elsevier.
Ratner, Lloyd E. et al., "Laparoscopic live donor nephrectomy," Transplantation, 1995, pp. 1047-1049.
Rau, Beate, M. eta al., "Is There Additional Information From Laparoscopic Ultrasound in Tumor Staging", Digestive Surgery, 2002, pp. 479-483, vol. 19—No. 6.
Rockall, Timothy A., "The da Vinci Telerobotic Surgical System," Chapter 8 in Primer of Robotic & Telerobotic Surgery, Eds. Garth H. Ballantyne et al., Pub. by Lippincott Williams & Wilkins, Philadelphia, 2004, pp. 57-60.
Rohling, Robert et al., "Three-dimensional spatial compounding of ultrasound images," Medical Image Analysis, 1996, pp. 177-193, vol. 1—No. 3, Oxford University Press.
Rohling, Robert N. et al., "Radial basis function interpolation for 3-d ultrasound," CUED/F-INFENG/TR 327, Cambridge University, Jul. 1998, 28 Pages.
Rosen, Jacob et al., "The BlueDRAGON—A System for Measuring the Kinematics and the Dynamics of Minimally Invasive Surgical Tools In-Viva," Proceedings of the 2002 IEEE International Conference on Robotics 8 Automation, 2002, pp. 1876-1881, IEEE.
Rosenberg, Louis B., "Virtual Fixtures: Perceptual Tools for Telerobotic Manipulation," IEEE Virtual Reality International Symposium, 1993, pp. 76-82, IEEE.
Rothbaum Daniel L. et al., "Robot-assisted stapedotomy: micropick fenestration of the stapes footplate," Otolaryngology—Head and NeckSurgery, 2002, pp. 417-426, vol. 127.
Rothbaum Daniel L. et al., "Task Performance in stapedotomy: Comparison between surgeons of different experience levels," Otolaryngology—Head and Neck Surgery, 2003, pp. 71-77, vol. 128—No. 1.
Roy, Jaydeep, "Advances in the design, analysis and control of force controlled robots," Master's Thesis, Mechanical Engineering, Johns Hopkins University, Baltimore, 2001, 210 Pages.
Sakas, Georgios et al., "Extracting surfaces from fuzzy 3D-Ultrasound data," Proceedings of the 22nd annual conference on Computer graphics and interactive techniques, 1995, pp. 465-474.
Salcudean, Septimiu E. et al., "A Robot System for Medical Ultrasound," 9th International Symposium of Robotics Research (ISRR'99), 1999, pp. 195-202.
Santambrogio, R. et al., "Ultrasound-Guided Interventional Procedures of the Liver During Laparoscopy: Technical Considerations," Surg Endosc, 2002, pp. 349-354, Springer-Verlag.
Schorr, Oliver et al., "Distributed Modular Computer-Integrated Surgical Robotic Systems: Architecture for Intelligent Object Distribution," Proceedings of the Third International Conference on Medical Image Computing and Computer-Assisted Intervention, Lecture Notes In Computer Science, 2000, pp. 979-978, vol. 1935, Springer.
Schreiner, Steve et al., "A system for percutaneous delivery of treatment with a fluoroscopically-guided robot," Proceedings of the First Joint Conference on Computer Vision, Virtual Reality and Robotics in Medicine and Medial Robotics and Computer-Assisted Surgery,Lecture Notes in Computer Science, 1997, pp. 747-756, Springer-Verlag.
Schweikard, Achim et al., "Motion Planning in Stereotaxic Radiosurgery," IEEE Transactions on Robotics and Automation, 1993, pp. 909-916, vol. 1, IEEE.
Scott, D.J., "Accuracy and Effectiveness of Laparoscopic vs. Open Hepatic Radiofrequency Ablation," Surg Endosc, 2001, pp. 349-354, vol. 16—No. 2, Springer.
Shahram, Payandeh, et al., "On Application of Virtual Fixtures as an Aid for Telemanipulation and Training," IEEE 10th Symposium on Haptic Interfaces for Virtual Environment and Teleoperator systems, Mar. 24-25, 2002, pp. 18-23, IEEE.
Simaan, Nabil et al., "A Dexterous System for Laryngeal Surgery: Multi-Backbone Bending Snake-like Slaves for Teleoperated Dextrous Surgical Tool Manipulation," IEEE International Conference on Robotics and Automation, 2004, pp. 351-357, IEEE.
Simaan, Nabil et al., "High Dexterity Snake-Like Robotic Slaves for Minimally Invasive Telesurgery of the Upper Airway," MICCAI 2004—the 7th International Conference on Medical Image Computing and Computer-Assisted Intervention, 2004, pp. 17-24.
Solomon, S. B. et al., "Robotically Driven Interventions: A Method of Using CT Fluoroscopy without Radiation Exposure to the Physician," Radiology, 2002, vol. 225, pp. 277-282.
Solus-3D Ultrasound Project in Obstetrics and Gynaecology, University of Cambridge, http://mi.eng.cam.ac.uk/research/projects/Solus/, downloaded Jul. 5, 2007, 4 pages.
Sommer, Graham et al., "Liver tumors: utility of characterization at dual frequency US," Radiology, 1999, pp. 629-636, vol. 211—No. 3.
Steele, Micah R. et al., "Shared control between human and machine: using a haptic steering wheel to aid in land vehicle guidance," Human Factors and Ergonomics Society 45th Annual Meeting , Minneapolis, Minnesota, 2001, pp. 1671-1675.
Steen, Erik et al., "Volume Rendering of 3D Medical Ultrasound Data Using Direct Feature Mapping," IEEE Transactions on Medical Imaging, 1994, pp. 517-525, vol. 13—Iss. 3, IEEE.
Stefansic, James D. et al., "Registration of Physical Space to Laparoscopic Image Space for Use in Minimally Invasive Hepatic Surgery," IEEE Transactions on Medical Imaging, 2000, pp. 1012-1023, vol. 19—No. 10, IEEE.

(56) References Cited

OTHER PUBLICATIONS

Stetten, George D et al., "Overlaying Ultrasound Images on Direct Vision," Journal of Ultrasound in Medicine, 2001, pp. 235-240, vol. 20—No. 3.

Stewart, Charles V. et al., "The Dual-Bootstrap Iterative Closest Point Algorithm With Application to Retinal Image Registration," IEEE Transactions on Medical Imaging, Nov. 2003, pp. 1379-1394, vol. 22—No. 11, IEEE.

Stoainovici D., et al., "Robotic Telemanipulation for Percutaneous Renal Access," in 16th World Congress On Endourology, New York City, Sep. 3-6, 1998, Poster Session 17-5, p. S201.

Stoianovici, Dan, "A Modular Surgical Robotic System for Image Guided Percutaneous Procedures," Proceedings of the First International Conference on Medical Image Computing and Computer-Assisted Intervention, pp. 404-410, vol. 1496, Springer-Verlag, 1998.

Stoianovici, Dan et al., "Robotic For Precise Percutaneous Needle Insertion," In Thirteenth Annual Meeting of the Society for Urology and Engineering. San Diego, May 1998, pp. 4.

Stoll, Jeff, "Ultrasound-based servoing of manipulators for telesurgery," Telemanipulator and Telepresence Technologies VIII Conference, 2001, pp. 78-85, SPIE.

Sublett, John W. et al. "Design and implementation of a digital teleultrasound system for real-time remote diagnosis," 8th IEEE Symposium on Computer-Based Medical Systems, IEEE Computer Society Press, Jun. 9-10, 1995, pp. 292-298.

Suramo, I. et al., "Cranio-caudal movements of the liver, pancreas and kidneys in respiration," Acta Radiologica: Diagnosis, 1984, pp. 129-131, vol. 25, Radiological Societies.

Susil, Robert, C. et al., "A Single Image Registration Method for CT Guided Interventions," 2nd International Symposium on Medical Image Computing and Computer-Assisted Interventions (MICCAI' 99),Lecture Notes in Computer Science, 1999, pp. 798-808, vol. 1679, Springer-Verlag.

Szeliski, Richard, "Motion Estimation with Quadtree Splines," IEEE 5th International Conference on Computer Vision, 1995, pp. 757-763, vol. 18—Issue. 12, IEEE Computer Society Washington, DC, USA .

Taylor R.H., et al., Table of Contents,"Computer-Integrated Surgery," Technology and Clinical Applications, The MIT Press, Cambridge, MA,1996, 8 pages.

Taylor, Russell H., "A Perspective on Medical Robotics," Proceedings of the IEEE, vol. 94, No. 9, Sep. 2006, pp. 1652-1664.

Taylor, Russell H. "An Image-directed Robotic System for Precise Orthopaedic Surgery," IEEE Transactions on Robotics mid Automation, 1994, pp. 261-275, vol. 10—No. 3, IEEE.

Taylor, Russell H. and Christopher Hasser, "Development of a Surgical Assistant Workstation for Teleoperated Surgical Robots," NSF Proposal No. 0646678, Aug. 2006, 16 pages.

Taylor, Russell H. and Dan Stoianovici, "Medical Robotic Systems in Computer-Integrated Surgery," Problems in General Surgery, by Lippincott Williams & Wilkins, Inc., Philadelphia, Pennsylvania. vol. 20, No. 2, pp. 1-9, 2003.

Taylor, Russell H. and Peter Kazanzides, "Medical Robotics and Computer-Integrated Interventional Medicine," Chapter 18: Biomedical Information Technology, David Dagan Feng, Ed., Academic Press (Elsevier), 2008, pp. 393-416.

Taylor, Russell H. et al., "A Computational Architecture for Programmable Automation Research," Conference on Intelligent Robots and Computer Vision, 1986, pp. 438-440, vol. 726, SPIE.

Taylor, Russell H. et al., "A General Purpose Control Architecture for Programmable Automation Research," Proceedings of the Third International Symposium on Robotics, 1986, pp. 165-174, MIT Press.

Taylor, Russell, H et al., "A Steady-Hand Robotic System for Microsurgical Augmentation," International Journal of Robotics Research, 1999, pp. 1201-1210, vol. 18—No. 12, Springer-Verlag.

Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.

Taylor, Russell H. et al., "A Telerobotic System for Augmentation of Endoscopic Surgery," in IEEE Conference on Engineering in Medicine and Biology, vol. 14, 1992, pp. 1054-1056, vol. 3, IEEE.

Taylor, Russell, H et al., "AML A Manufacturing Language," The International Journal of Robotics Research, 1982, pp. 19-41, vol. 1—No. 3, SAGE Publications.

Taylor, Russell H. et al., "An Image-directed Robotic System for Hip Replacement Surgery," J. Robotics Society of Japan, 1990, pp. 615-620, vol. 8—issue 5.

Taylor, Russell, H. et al., "An Integrated Robot Systems Architecture," Proceedings of the IEEE, 1983, pp. 842-856, vol. 71—Issue 7, IEEE.

Taylor, Russell H., et al., "An overview of computer-integrated surgery at the IBM Thomas J. Watson Research Center," IBM J Research and Development, 1996, pp. 163-183, vol. 40, Issue 2, IBM Corp.

Taylor, Russell H., et al., "Chapter 46: A Telerobotic Assistant for Laparoscopic Surgery," in Computer-Integrated Surgery, R. H. Taylor, et al., Editors, 1996, MIT Press, pp. 581-592.

Taylor, Russell H. et al., "Computer-Integrated Revision Total Hip Replacement Surgery: Concept and Preliminary Results," 1999, Medical image analysis, pp. 301-319, vol. 3—Issue 3, Oxford University Press.

Taylor, Russell H. et al., "Medical Robotics and Computer-Integrated Surgery," Chapter 52 in Springer Handbook of Robotics, Springer, 2008, pp. 1199-1222.

Taylor, Russell H. et al., "Medical Robotics in Computer-Integrated Surgery," IEEE Transactions on Robotics md Automation, 2003, pp. 765-781, vol. 19—No. 5, IEEE.

Taylor, Russell, H. et al., "Redundant Consistency Checking in a Precise Surgical Robot," in 12'th Annual Conference on Engineering in Medicine and Biology, 1990, pp. 1933-1935, vol. 12—No. 5, IEEE.

Taylor, Russell, H et al., "The Architecture of an Integrated Robot System," First Int. Conf. on Advanced Robotics (ICAR)., 1983, pp. 389-398.

Taylor, Russell H. "Medical Robotics and Computer-Integrated Surgery," Handbook of Industrial Robotics, Second Edition, 1999, pp. 1213-1230, Chapter 65, John Wiley & Sons.

Taylor, Russell H. "Medical Robots," in Computer and Robotic Assisted Knee and Hip Surgery, 2004, pp. 54-59, Oxford Press.

Taylor, Russell H., "Robotics in Orthopedic Surgery," In Computer Assisted Orthopaedic Surgery (CAOS), L.P. Nolte and R. Ganz, Editors. 1999, Hogrefe and Huber, 1999, pp. 35-41.

Taylor, Russell H. "The Planning and Execution of Straight Line Manipulator Trajectories," IBM Journal of Research and Development, 1979, pp. 424-436, vol. 23—Issue 4.

Taylor, Russell H., "Ultrasound Assistant for a Laparoscopic Surgical Robot," NIH STTR Phase II Proposal R42-RR019159, revised May 2001, 54 pages.

Taylor, Russell H., Videotape: "Computer Assisted Surgery at IBM T. J. Watson Research Center," 22 minutes 10 seconds, 1994 and 1995.

Teistler, Michael et al., "Virtual Tomography: A New Approach to Efficient Human-Computer Interaction for Medical Imaging," Proc. of SPIE., The International Society for Optical Engineering (SPIE), Medical Imaging 2003: Visualization, Image-Guided Procedures, and Display; San Diego, CA, Ed. Robert L. Galloway, 2003, pp. 512-519, vol. 5029.

Tewari, Ashutosh et al., "Technique of da Vinci Robot-Assisted Anatomic Radical Prostatectomy," Urology, 2002, pp. 569-572,vol. 60—No. 4, Elsevier.

The VolPack Volume Rendering Library, https://graphics.stanford.edu/software/volpack/, 1995, 4 pages.

Toyama, Kentaro et al., "Incremental Focus of Attention for Robust Vision-based Tracking," International Journal of Computer Vision, 1999, pp. 45-63, vol. 35—No. 1, Kluwer Academic Publishers.

Troccaz, Jocelyne et al., "The use of localizers, robots, and synergistic devices in CAS," Proceedings of the First Joint Conference on Computer Vision, Virtual Reality and Robotics in Medicine and Medial Robotics and Computer-Assisted Surgery,Lecture Notes in Computer Science, 1997, pp. 727-736, vol. 1205, Springer-Verlag.

(56) References Cited

OTHER PUBLICATIONS

Uecker, Darrin R. et al., "A Speech-Directed Multi-Modal Man-Machine Interface for Robotically Enhanced Surgery," 1994, pp. 176-183.

Umeyama, Shinji, "Least-Squares Estimation of Transformation Parameters between Two Point Patterns," IEEE Transactions on Pattern Analysis and Machine Intelligence (PAMI), vol. 13, No. 4, pp. 376-380, Apr. 1991.

U.S. Appl. No. 11/583,963 Non-Final Office Action dated Jul. 9, 2009, 40 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Vilchis, Adriana et al., "A New Robot Architecture for Tele-Echography," IEEE Trans. Robotics & Automation, pp. 922-926, 2003, vol. 19—No. 5, IEEE.

Viswanathan, Anand et al., "Immediate Ultrasound Calibration with Three Poses and Minimal Image Processing," MICCAI, 2004, pp. 446-454, vol. 2, Springer-Verlag.

Webster Robert J. et al., "Design Considerations for Robotic Needle Steering," International Conference on Robotics and Automation, 2005, pp. 3588-3594, IEEE.

Webster Robert J. et al "Nonholonomic Modeling of Needle Steering," The International Journal of Robotics Research, 2004, pp. 509-525, vol. 25—No. 5-6, SAGE Publications.

Wei, Zhouping et al "Robot-assisted 3D-TRUS guided prostate brachytherapy: system integration and validation," Medical Physics, 2004, pp. 539-548, vol. 31—No. 3.

Wengert, C., "Camera Calibration Toolbox for Matlab," http://www.vision.caltech.edu/bouguetj/calib_doc/, downloaded Oct. 24, 2006, 9 pages.

Wilhelm, Dirk et al., "Electromagnetically Navigated Laparoscopic Ultrasound," Surg. Technol. Int, 2003, pp. 50-54, vol. 11.

Wood Thomas F. et al., "Radiofrequency ablation of 231 Unresectable hepatic tumors:indications, limitations, and complications," Ann. Surg. Oncol, 2000, pp. 593-600, vol. 7, Lippincott Williams & Wilkins.

Wu, Xiaohui et al., "A Framework for Calibration of Electromagnetic Surgical Navigation Systems," IEEE RSJ International Conference on Intelligent Robot Systems (IROS), 2003, pp. 547-552, vol. 1, IEEE.

Xu, Sheng et al., "3D Motion Tracking of Pulmonary Lesions Using CT Fluoroscopy Images for Robotically Assisted Lung Biopsy," Proc. SPIE. 5367, Medical Imaging 2004: Visualization, Image-Guided Procedures, and Display, 394. (May 5, 2004), pp. 394-402.

Yamagata, Hitoshi, "Development of a New Display Method for Compound 3D Ultrasound Images: Fusion 3D Images From B-mode and 3D Doppler Images," 1999, pp. 43-46, vol. 70.

Yao, Jianhua et al., "A C-arm fluoroscopy-guided progressive cut refinement strategy using a surgical robot," Computer Aided Surgery, 2000, pp. 373-390, vol. 5—No. 6, Wiley-Liss, Inc.

Yao, Jianhua, et al., "A Progressive Cut Refinement Scheme for Revision Total Hip Replacement Surgery Using C-arm Fluoroscopy," Proceedings of the 2nd International Conference on Medical Image and Computer-Assisted Intervention (MICCAI'99), Springer-Verlag, 1999, pp. 1010-1019, vol. 1679.

Yao, Jianhua et al., "Deformable registration between a statistical born density atlas and X-ray images," Second International Conference on Computer Assisted Orthopaedic Surgery, 2002, pp. 168-169.

Zacherl, Johannes et al., "Current value of intraoperative sonography during surgery for hepatic neoplasms," World J Surg, 2002, pp. 550-554, vol. 26—No. 5.

Zhang, Z., "A Flexible New Technique for Camera Calibration," Technical report MSR-TR-98-71, Microsoft Research, Microsoft Corporation, Redmond, WA, Dec. 1998, pp. 1-21.

Extended European Search Report for Application No. EP20158283.0 dated Jun. 17, 2020, 6 pages.

\* cited by examiner

INTERACTIVE USER INTERFACES FOR MINIMALLY INVASIVE TELESURGICAL SYSTEMS

CROSS REFERENCE TO RELATED APPLICATIONS

This non-provisional United States (U.S.) patent application claims the benefit and is a divisional of U.S. patent application Ser. No. 13/775,574, entitled SYSTEMS AND METHODS FOR INTERACTIVE USER INTERFACES FOR ROBOTIC MINIMALLY INVASIVE SURGICAL SYSTEMS, filed on Feb. 25, 2013, now issued as U.S. Pat. No. 9,765,446. U.S. patent application Ser. No. 13/775,574 claims the benefit of and is a divisional of U.S. patent application Ser. No. 12/189,615 filed on Aug. 11, 2008 by Simon P. Dimaio et al., entitled INTERACTIVE USER INTERFACES FOR ROBOTIC MINIMALLY INVASIVE SURGICAL SYSTEMS, now U.S. Pat. No. 8,398,541. U.S. patent application Ser. No. 12/189,615 is a non-provisional application and claims the benefit of provisional U.S. Patent Application No. 60/954,869 filed on Aug. 9, 2007 by inventors Christopher J. Hasser, et al., entitled ROBOTIC MINIMALLY INVASIVE SURGICAL SYSTEMS, which is incorporated herein by reference. U.S. patent application Ser. No. 12/189,615 also claims the benefit of and is a continuation-in-part (CIP) of U.S. patent application Ser. No. 11/447,668 filed on Jun. 6, 2006 by Christopher J. Hasser et al entitled ULTRASOUND GUIDANCE FOR A LAPAROSCOPIC SURGICAL ROBOT which is incorporated herein by reference. U.S. patent application Ser. No. 11/447,668 further claims the benefit of U.S. patent application Ser. No. 60/688,013 filed on Jun. 6, 2005.

U.S. patent application Ser. No. 11/447,668 further incorporates by reference U.S. patent application Ser. No. 11/130,471 entitled METHODS AND SYSTEM FOR PERFORMING 3-D TOOL TRACKING BY FUSION OF SENSOR AND/OR CAMERA DERIVED DATA DURING MINIMALLY INVASIVE SURGERY, filed on May 16, 2005 by Brian David Hoffman et al.; U.S. Pat. No. 6,659,939 entitled COOPERATIVE MINIMALLY INVASIVE TELESURGICAL SYSTEM, issued on Dec. 9, 2003 to Frederic H. Moll et al.; and U.S. Pat. No. 5,797,900 entitled WRIST MECHANISM FOR SURGICAL INSTRUMENT FOR PERFORMING MINIMALLY INVASIVE SURGERY WITH ENHANCED DEXTERITY AND SENSITIVITY, issued on Aug. 25, 1998 to Akhil J. Madhani et al., which are also incorporated herein by reference.

Furthermore, U.S. Pat. No. 6,522,906 entitled DEVICES AND METHODS FOR PRESENTING AND REGULATING AUXILIARY INFORMATION ON AN IMAGE DISPLAY OF A TELESURGICAL SYSTEM TO ASSIST AN OPERATOR IN PERFORMING A SURGICAL PROCEDURE, issued on Feb. 18, 2003 to J. Kenneth Salisbury, Jr. et al.; U.S. Pat. No. 6,459,926 entitled REPOSITIONING AND REORIENTATION OF MASTER/SLAVE RELATIONSHIP IN MINIMALLY INVASIVE TELESURGERY, issued on Oct. 1, 2006 to William C. Nowlin et al.; U.S. Pat. No. 6,493,608 entitled ASPECTS OF A CONTROL SYSTEM OF A MINIMALLY INVASIVE SURGICAL APPARATUS, issued on Dec. 10, 2002 to Gunter D. Niemeyer; U.S. Pat. No. 6,799,065 entitled IMAGE SHIFTING APPARATUS AND METHOD FOR A TELEROBOTIC SYSTEM, issued on Sep. 28, 2004 to Gunter D. Niemeyer; and U.S. Pat. No. 6,714,939 entitled MASTER HAVING REDUNDANT DEGREES OF FREEDOM, issued on Mar. 30, 2004 to Salisbury et al. are all incorporated herein by reference.

FEDERALLY SPONSORED RESEARCH OR DEVELOPMENT

The assignees of this United States (U.S.) patent application elect to retain the rights in this invention. This invention was made with government support under EEC9731748 and EEC0646678 awarded by the National Science Foundation and under RR019159 awarded by the National Institutes of Health. The government has certain rights in the invention.

FIELD OF INVENTION

Aspects of the invention are related to user interfaces for a surgeon's workstation in robotic surgical systems.

BACKGROUND OF INVENTION

Minimally invasive robotic surgical systems, such as the da Vinci® Surgical System, are manufactured by Intuitive Surgical, Inc., of Sunnyvale, Calif. The Johns Hopkins University Engineering Research Center for Computer-Integrated Surgical Systems and Technology (ERC-CISST) conducts research in aspects of minimally invasive surgical systems.

The number of robotic arms available in minimally invasive robotic surgical systems has been slowly increasing to support additional robotic surgical tools over a patient. Additionally, some more recent robotic surgical tools have a greater number of controllable features. Unfortunately, a surgeon has only a pair of eyes, hands and feet to select and control the greater number of tools and controllable features of the robotic surgical tools.

SUMMARY OF INVENTION

The embodiments of the invention are summarized by the claims that follow below.

DETAILED DESCRIPTION

In the following detailed description of the embodiments of the invention, numerous specific details are set forth in order to provide a thorough understanding of the invention. However, the embodiments of the invention may be practiced without these specific details. In other instances well known methods, procedures, components, and circuits have not been described in detail so as not to unnecessarily obscure aspects of the embodiments of the invention.

Introduction

Various embodiments of a minimally invasive surgical master/slave robotic system allow ultrasonic image display, image manipulation, supervisor/trainee master consoles, automatic movement limitation, and interchangeable slave consoles. For example, U.S. patent application Ser. No. 11/447,668 entitled ULTRASOUND GUIDANCE FOR A LAPAROSCOPIC SURGICAL ROBOT to which priority is claimed, describes a minimally invasive surgical robotic system with a laparoscopic ultrasonic robotic tool.

Figure 1:
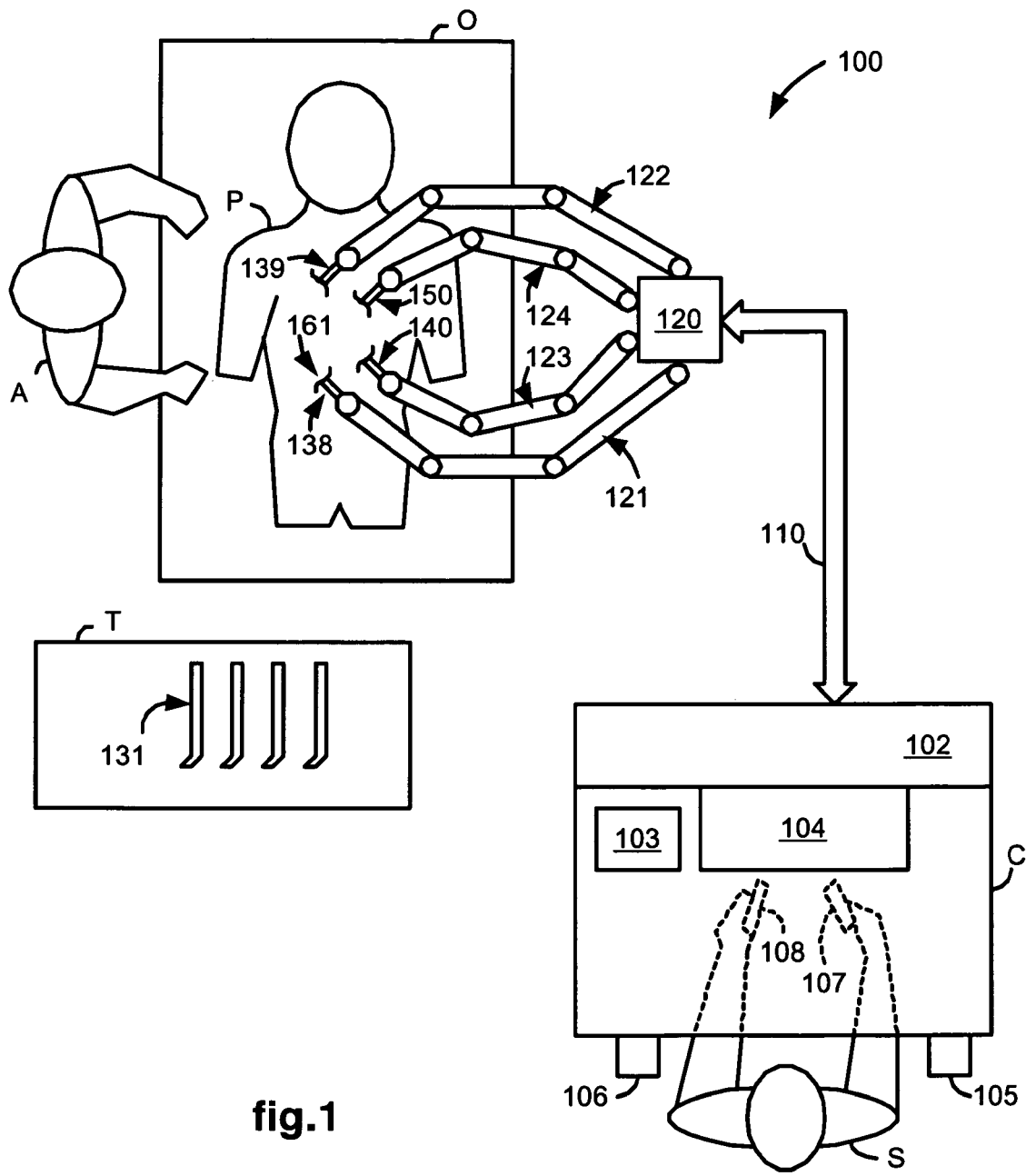
FIG. 1 illustrates a top view of an operating room employing a laparoscopic ultrasound robotic surgical system utilizing aspects of the embodiments of the invention.

FIG. 1 illustrates, as an example, a top view of an operating room employing a robotic surgical system. The robotic surgical system in this case is a laparoscopic ultrasound robotic surgical system 100 including a console ("C") (also may be referred to herein as a surgeon console, master console, master surgeon console, or surgical console) utilized by a surgeon ("S") while performing a minimally invasive diagnostic or surgical procedure with assistance from one or more assistants ("A") on a patient ("P") who is reclining on an operating table ("O").

The console C includes a master display 104 (also referred to herein as a display screen or display device) for displaying one or more images of a surgical site within the patient as well as perhaps other information to the surgeon. Also included are master input devices 107 and 108 (also referred to herein as master manipulators or master tool manipulators (MTM), master grips, hand control devices), one or more foot pedals 105 and 106, a microphone 103 for receiving voice commands from the surgeon, and a processor 102. The master input devices 107 and 108 may include any one or more of a variety of input devices such as joysticks, gloves, trigger-guns, hand-operated controllers, or the like. The processor 102 may be a computer or a part of a computer that may be integrated into the surgeon console or otherwise connected to the surgeon console in a conventional manner.

The surgeon performs a minimally invasive surgical procedure by manipulating the master input devices 107 and 108 so that the processor 102 causes their respectively associated slave arms 121 and 122 (also referred to herein as slave manipulators or slave robots) of the patient side cart (PSC) 120 to manipulate their respective removeably coupled and held surgical instruments 138 and 139 (also referred to herein as tools or minimally invasive surgical instruments) accordingly, while the surgeon views three-dimensional ("3D") images of the surgical site on the master display 104.

The tools 138 and 139, in one embodiment of the invention, are Intuitive Surgical Inc.'s proprietary ENDOWRIST™ articulating instruments, which are modeled after the human wrist so that when added to the motions of the robot arm holding the tool, they allow a full six degrees of freedom of motion, which is comparable to the natural motions of open surgery. Additional details on such tools may be found in U.S. Pat. No. 5,797,900 entitled WRIST MECHANISM FOR SURGICAL INSTRUMENT FOR PERFORMING MINIMALLY INVASIVE SURGERY WITH ENHANCED DEXTERITY AND SENSITIVITY, issued on Aug. 25, 1998 to Akhil J. Madhani et al. which is incorporated herein by this reference. At the operating end of each of the tools 138 and 139 is a manipulatable end effector such as a clamp, grasper, scissor, stapler, blade, needle, or needle holder.

The master display 104 is a high-resolution stereoscopic video display device. In one embodiment of the invention, the high-resolution stereoscopic video display device is formed of two progressive scan cathode ray tubes ("CRTs"). In another embodiment of the invention, the high-resolution stereoscopic video display device is formed of two liquid crystal display ("LCDs") devices. The system offers higher fidelity than polarization, shutter eyeglass, or other techniques. Each eye views a separate display presenting the left or right eye perspective, through an objective lens and a series of mirrors. The surgeon sits comfortably and looks into this display throughout surgery, making it an ideal place for the surgeon to display and manipulate 3-D intraoperative imagery.

A stereoscopic endoscope 140 (also referred to herein as an endoscopic camera) provides right and left camera views to the processor 102 so that it may process the information according to programmed instructions and cause it to be displayed on the master display 104. A laparoscopic ultrasound ("LUS") probe 150 provides two-dimensional ("2D") ultrasound image slices of an anatomic structure to the processor 102 so that the processor 102 may generate a 3D ultrasound computer model of the anatomic structure and cause the 3D computer model (or alternatively, 2D "cuts" of it) to be displayed on the master display 104 as an overlay to the endoscope derived 3D images or within a picture-in-picture ("PIP") in either 2D or 3D and from various angles and/or perspectives according to surgeon or stored program instructions.

Each of the tools 138 and 139, as well as the endoscope 140 and LUS probe 150, is preferably inserted through a cannula or trocar (not shown) or other tool guide into the patient so as to extend down to the surgical site through a corresponding minimally invasive incision such as Incision 166. Each of the slave arms 121-124 is conventionally formed of linkages which are coupled together and manipulated through motor controlled joints (also referred to as "active joints"). Setup arms (not shown) comprising linkages and setup joints are used to position the slave arms 121-124 vertically and horizontally so that their respective surgical related instruments may be coupled for insertion into the cannulae.

The number of surgical tools used at one time and consequently, the number of slave arms being used in the system 100 will generally depend on the diagnostic or surgical procedure and the space constraints within the operating room, among other factors. If it is necessary to change one or more of the tools being used during a procedure, the Assistant may remove the tool no longer being used from its slave arm, and replace it with another tool, such as a minimally invasive surgical tool 131, from a tray ("T") in the operating room.

Preferably, the master display 104 is positioned near the surgeon's hands so that it will display a projected image that is oriented so that the surgeon feels that he or she is actually looking directly down onto the surgical site. To that end, an image of the tools 138 and 139 preferably appear to be located substantially where the surgeon's hands are located even though the observation points (i.e., that of the endoscope 140 and LUS probe 150) may not be from the point of view of the image.

In addition, the real-time image is preferably projected into a perspective image such that the surgeon can manipulate the end effector of a tool, 138 or 139, through its associated master input device, 107 or 108, as if viewing the workspace in substantially true presence. By true presence, it is meant that the presentation of an image is a true perspective image simulating the viewpoint of an operator that is physically manipulating the tools. Thus, the processor 102 transforms the coordinates of the tools to a perceived position so that the perspective image is the image that one would see if the endoscope 140 was looking directly at the tools from a surgeon's eye-level during an open cavity procedure.

The processor 102 performs various functions in the system 100. One function that it performs is to translate and transfer the mechanical motion of master input devices 107 and 108 to their associated slave arms 121 and 122 through control signals over bus 110 so that the surgeon can effectively manipulate their respective tools 138 and 139. Another function of the processor 102 is to implement the various methods and functions described herein, including providing a robotic assisted LUS capability.

Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware. Program code or instructions for the processor 102 to implement the various methods and functions described herein may be stored in processor readable storage media, such as memory (e.g., memory 240 illustrated in FIG. 2).

Prior to performing a minimally invasive surgical procedure, ultrasound images captured by the LUS probe 150, right and left 2D camera images captured by the stereoscopic endoscope 140, and end effector positions and orientations as determined using kinematics of the slave arms 121-124 and their sensed joint positions, are calibrated and registered with each other.

In order to associate the ultrasound image with the rest of the surgical environment, both need to be expressed in the same coordinate frame. Typically, the LUS probe 150 is either labeled with markers and tracked by a tracking device such as the OPTORAK® position sensing system manufactured by Northern Digital Inc. of Ontario, Canada, or held by a robot with precise joint encoders. Then the rigid transformation between the ultrasound image and the frame being tracked is determined (which is typically referred to as the ultrasound calibration).

For example, using the OPTOTRAK® frame for the ultrasound calibration, the ultrasound image generated by the LUS probe 150 is calibrated to an OPTOTRAK® rigid body using an AX=XB formulation. "AX=XB" is a rubric for a class of calibration/registration problem commonly encountered in computer vision, surgical navigation, medical imaging, and robotics. The mathematical techniques are well known. See, e.g., E. Boctor, A. Viswanathan, M. Chioti, R. Taylor, G. Fichtinger, and G. Hager, "A Novel Closed Form Solution for Ultrasound Calibration," *International Symposium on Biomedical Imaging*, Arlington, Va., 2004, pp. 527-530.

"A" and "B" in this case, are transformations between poses of the OPTOTRAK® rigid body (A) and the ultrasound image (B). Thus, "X" is the transformation from the ultrasound image to the rigid body.

To perform the ultrasound calibration, the LUS probe 150 may be placed in three known orientations defined by the AX=XB calibration phantom. The ultrasound image frame may then be defined by three fiducials which appear in each of the three poses. The three poses allow three relative transformations based on OPTOTRAK® readings (A) and three relative transformations based on the ultrasound images (B) for the AX=XB registration.

Camera calibration is a common procedure in computer vision applications. As an example, in order to determine the intrinsic and extrinsic parameters of the endoscope 140, a checkerboard phantom with a multi-plane formulation may be provided by the Caltech's camera calibration toolbox. To construct the phantom, OPTOTRAK® markers are added to a typical checkerboard video calibration phantom, and each corner of the checkerboard is digitized using a calibrated OPTOTRAK® pointer. Thus, the corner positions may be reported with respect to the OPTOTRAK®.

The calibration may then be performed by placing the phantom in view of the endoscope 140 in several dozen orientations, and recording both stereo image data and OPTOTRAK® readings of the four checkerboard corners. The images may then be fed into the calibration toolbox, which determines the intrinsic and extrinsic camera parameters, as well as the 3D coordinates of the grid corners in the camera frame. These coordinates may then be used with the OPTOTRAK® readings to perform a point-cloud to point-cloud registration between the endoscope 140 rigid body and camera frame.

The processor/controller 102 is configured to use the robot kinematics to report a coordinate frame for the LUS probe 150 tip relative to the endoscope 140. However, due to inaccuracies in the setup joint encoders, both of these coordinate frames may be offset from their correct values. Thus, it may be necessary to register the offsets between the real camera frame of the endoscope 140 and the camera frame calculated from the kinematics as well as between the real and kinematic LUS probe 150 frames. With this complete, the kinematics may be used in place of the OPTOTRAK® readings to determine ultrasound image overlay placement.

If the position of the endoscope 140 doesn't overly change, a constant transformation may be assumed between the kinematic tool tip and the laparoscopic OPTOTRAK® rigid body. Using an AX=XB formulation, the LUS probe 150 may be moved, for example, to several positions, and the static offset between the tool tip and OPTOTRAK® rigid body registered. Knowing this offset, the endoscope 140 offset may be calculated directly:

$$C_{CD} = D_{LusD}(C_{LusUrb})^{-1} T_{OUrb}(T_{OErb})^{-1} F_{CErb} \quad (1)$$

where $C_{CD}$ is the camera offset from the real endoscope 140 (also referred to herein simply as the "camera") frame to the camera frame calculated from the kinematics, $F_{CErb}$ is the transformation from the camera to the endoscope rigid body, $T_{OUrb}*(T_{OErb})^{-1}$ is the transformation from the camera rigid body to the LUS rigid body, $C_{LusUrb}$ is the transformation from the LUS rigid body to the kinematic ultrasound tool tip, and $D_{LusD}$ is the reading from the processor/controller 102 giving the transformation from the kinematic ultrasound tool tip to a fixed reference point associated with the slave arms 121-124.

However, registration may be redone each time the camera is moved. For intra-operative, the registration may be better performed using video tracking of a visual marker on the LUS probe 150 instead of the OPTOTRAK® readings. Thus, if the camera were moved while using tool tracking, the registration can be corrected on the fly as the tool is tracked. For additional details on tool tracking, see, e.g., U.S. patent application Ser. No. 11/130,471 entitled METHODS AND SYSTEM FOR PERFORMING 3-D TOOL TRACKING BY FUSION OF SENSOR AND/OR CAMERA DERIVED DATA DURING MINIMALLY INVASIVE SURGERY, filed on May 16, 2005 by Brian David Hoffman et al., which is incorporated herein by reference. In addition to, or alternatively, manual registration of ultrasound and camera images may be performed using conventional grab, move and rotate actions on a 3D ultrasound computer model of an anatomic structure, so that the computer model is properly registered over a camera model of the anatomic structure in the master display 104.

Slave arms 123 and 124 may manipulate the endoscope 140 and LUS probe 150 in similar manners as slave arms 121 and 122 manipulate tools 138 and 139. When there are only two master input devices in the system, however, such as master input devices 107 and 108 in the system 100, in order for the surgeon to manually control movement of either the endoscope 140 or LUS probe 150, it may be required to temporarily associate one of the master input devices 107 and 108 with the endoscope 140 or the LUS probe 150 that the surgeon desires manual control over, while its previously associated tool and slave manipulator are locked in position.

Figure 2:
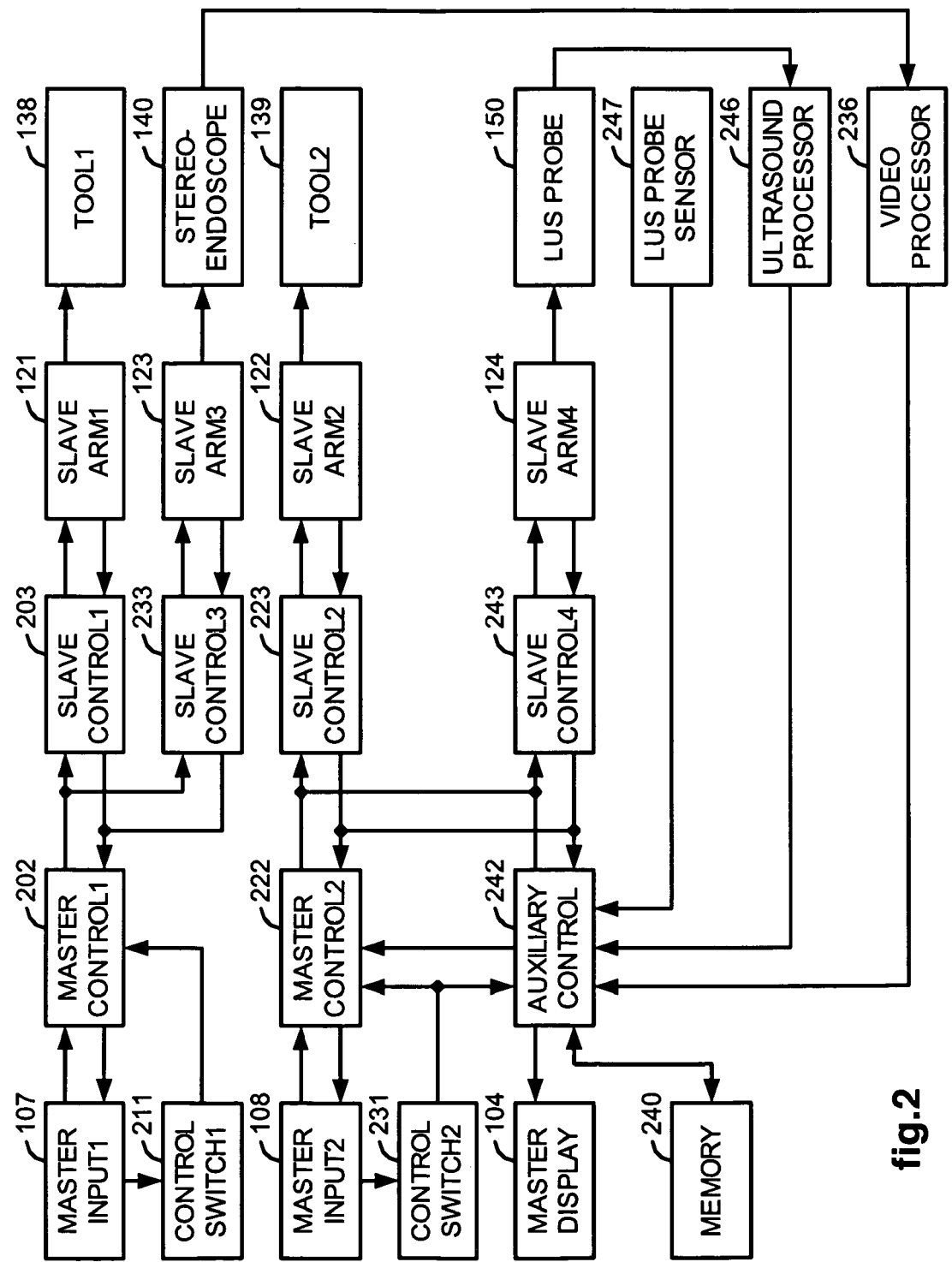
FIG. 2 illustrates a block diagram of a laparoscopic ultrasound robotic surgical system utilizing aspects of the embodiments of the invention.

FIG. 2 illustrates, as an example, a block diagram of the LUS robotic surgical system 100. In this system, there are two master input devices 107 and 108. The master input device 107 controls movement of either a tool 138 or a stereoscopic endoscope 140, depending upon which mode its control switch mechanism 211 is in, and master input device 108 controls movement of either a tool 139 or a LUS probe 150, depending upon which mode its control switch mechanism 231 is in.

The control switch mechanisms 211 and 231 may be placed in either a first or second mode by a surgeon using voice commands, switches physically placed on or near the master input devices 107 and 108, foot pedals 105 and 106 on the console, or surgeon selection of appropriate icons or other graphical user interface selection means displayed on the master display 104 or an auxiliary display (not shown).

When control switch mechanism 211 is placed in the first mode, it causes master controller 202 to communicate with slave controller 203 so that manipulation of the master input 107 by the surgeon results in corresponding movement of tool 138 by slave arm 121, while the endoscope 140 is locked in position. On the other hand, when control switch mechanism 211 is placed in the second mode, it causes master controller 202 to communicate with slave controller 233 so that manipulation of the master input 107 by the surgeon results in corresponding movement of endoscope 140 by slave arm 123, while the tool 138 is locked in position.

Similarly, when control switch mechanism 231 is placed in the first mode, it causes master controller 222 to communicate with slave controller 223 so that manipulation of the master input 108 by the surgeon results in corresponding movement of tool 139 by slave arm 122. In this case, however, the LUS probe 150 is not necessarily locked in position. Its movement may be guided by an auxiliary controller 242 according to stored instructions in memory 240. The auxiliary controller 242 also provides haptic feedback to the surgeon through master input 108 that reflects readings of a LUS probe force sensor 247. On the other hand, when control switch mechanism 231 is placed in the second mode, it causes master controller 222 to communicate with slave controller 243 so that manipulation of the master input 222 by the surgeon results in corresponding movement of LUS probe 150 by slave arm 124, while the tool 139 is locked in position.

Before switching back to the first or normal mode, the master input device 107 or 108 is preferably repositioned to where it was before the switch to the second mode of Control Switch 211 or 231, as the case may be, or kinematic relationships between the master input device 107 or 108 and its respective tool slave arm 121 or 122 is readjusted so that upon switching back to the first or normal mode, abrupt movement of the tool 138 or 139 does not occur. For additional details on control switching, see, e.g., U.S. Pat. No. 6,659,939 entitled COOPERATIVE MINIMALLY INVASIVE TELESURGICAL SYSTEM, issued on Dec. 9, 2003 to Frederic H. Moll et al., which is incorporated herein by this reference.

The auxiliary controller 242 also performs other functions related to the LUS probe 150 and the endoscope 140. It receives output from a LUS probe force sensor 247, which senses forces being exerted against the LUS probe 150, and feeds the force information back to the master input device 108 through the master controller 222 so that the surgeon may feel those forces even if he or she is not directly controlling movement of the LUS probe 150 at the time. Thus, potential injury to the patient is minimized since the surgeon has the capability to immediately stop any movement of the LUS probe 150 as well as the capability to take over manual control of its movement.

Another key function of the auxiliary control 242 is to cause processed information from the endoscope 140 and the LUS probe 150 to be displayed on the master display 104 according to user selected display options. As will be described in more detail below, such processing includes generating a 3D ultrasound image from 2D ultrasound image slices received from the LUS probe 150 through an Ultrasound processor 246, causing either 3D or 2D ultrasound images corresponding to a selected position and orientation to be displayed in a picture-in-picture window of the master display 104, and causing either 3D or 2D ultrasound images of an anatomic structure to overlay a camera captured image of the anatomic structure being displayed on the master display 104.

Although shown as separate entities, the master controllers 202 and 222, slave controllers 203, 233, 223, and 243, and auxiliary controller 242 are preferably implemented as software modules executed by the processor 102, as well as certain mode switching aspects of the control switch mechanisms 211 and 231. The Ultrasound processor 246 and Video processor 236, on the other hand, are separate boards or cards typically provided by the manufacturers of the LUS probe 150 and endoscope 140 that are inserted into appropriate slots coupled to or otherwise integrated with the processor 102 to convert signals received from these image capturing devices into signals suitable for display on the master display 104 and/or for additional processing by the auxiliary controller 242 before being displayed on the master display 104.

Figure 3:
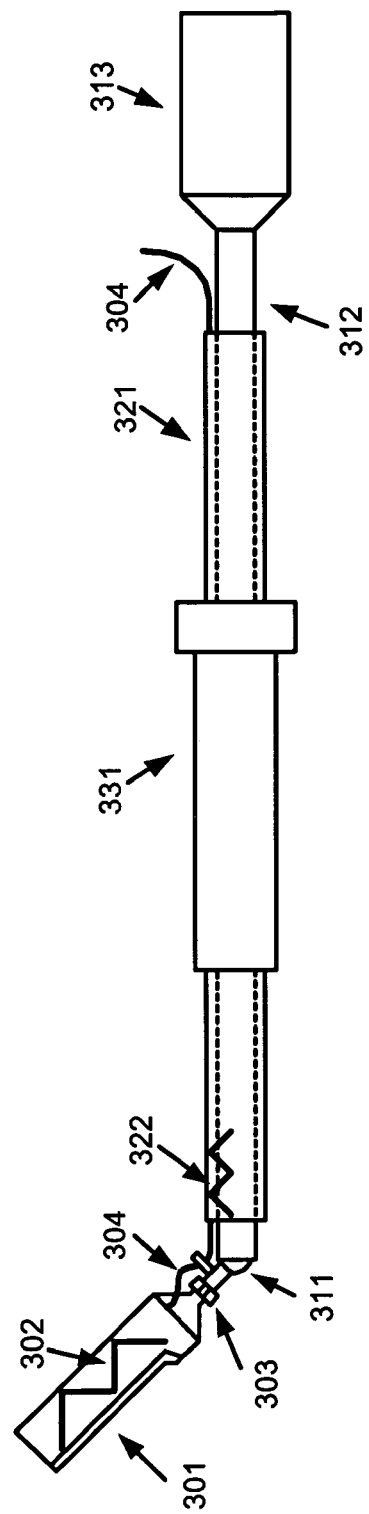
FIG. 3 illustrates a laparoscopic ultrasound probe utilizing aspects of the embodiments of the invention.

FIG. 3 illustrates a side view of one embodiment of the laparoscopic ultrasound (LUS) probe 150. The LUS probe 150 is a dexterous tool with preferably two distal degrees of freedom, permitting reorientation of laparoscopic ultrasound (LUS) sensor 301 through, for example, approximately ±80° in distal "pitch" and "yaw", and ±240° in "roll" about a ball joint type, pitch-yaw mechanism 311 (functioning as and also referred to herein as a "Wrist" mechanism). Opposing pairs of Drive Rods or cables (not shown) physically connected to a proximal end of the LUS sensor 301 and extending through an internal passage of elongated shaft 312 mechanically control pitch and yaw movement of the LUS sensor 301 using conventional push-pull type action. This flexibility of the LUS probe 150 (provided by the pitch/yaw wrist mechanism) is especially useful in optimally orienting the LUS probe 150 for performing ultrasonography on an anatomic structure during a minimally invasive surgical procedure.

The LUS sensor 301 captures 2D ultrasound slices of a proximate anatomic structure, and transmits the information back to the processor 102 through LUS cable 304. Although shown as running outside of the elongated shaft 312, the LUS cable 304 may also extend within it. A clamshell sheath 321 encloses the elongated shaft 312 and LUS cable 304 to provide a good seal passing through a cannula 331 (or trocar). Fiducial marks 302 and 322 are placed on the LUS sensor 301 and the sheath 321 for video tracking purposes.

A force sensing capability is provided by strain gauges 303 which provide direct feedback of how hard the LUS probe 150 is pushing on a structure being sonographed, supplementing whatever limited feedback is available from joint motor torques. Potential uses of this information include: providing a redundant safety threshold check warning the surgeon or preventing motion into the structure if forces get too great; providing the surgeon with an approved haptic appreciation of how hard he or she is pushing on a structure; and possibly permitting some measure of compensation for unmodeled deflections of the pitch-yaw or wrist mechanism 311 which are not detected for some reason by joint position sensors or encoders. The strain gauges 303 in this case serve the function of the LUS probe force sensor 247 as previously described in reference to FIG. 2.

Robotic assisted LUS has the potential to reduce variability in the ultrasound images produced, compared to freehand scanning, and can reduce operator workload and difficulty. Behaviors as simple as rocking the LUS probe 150 back and forth can maintain an updated 3D ultrasound image without operator intervention. More complicated behaviors can include movement of the LUS probe 150 along the surface of a target anatomical structure in a methodical pattern to generate a full image of the target, or reliably returning to a previously scanned probe location and orientation.

Figure 4:
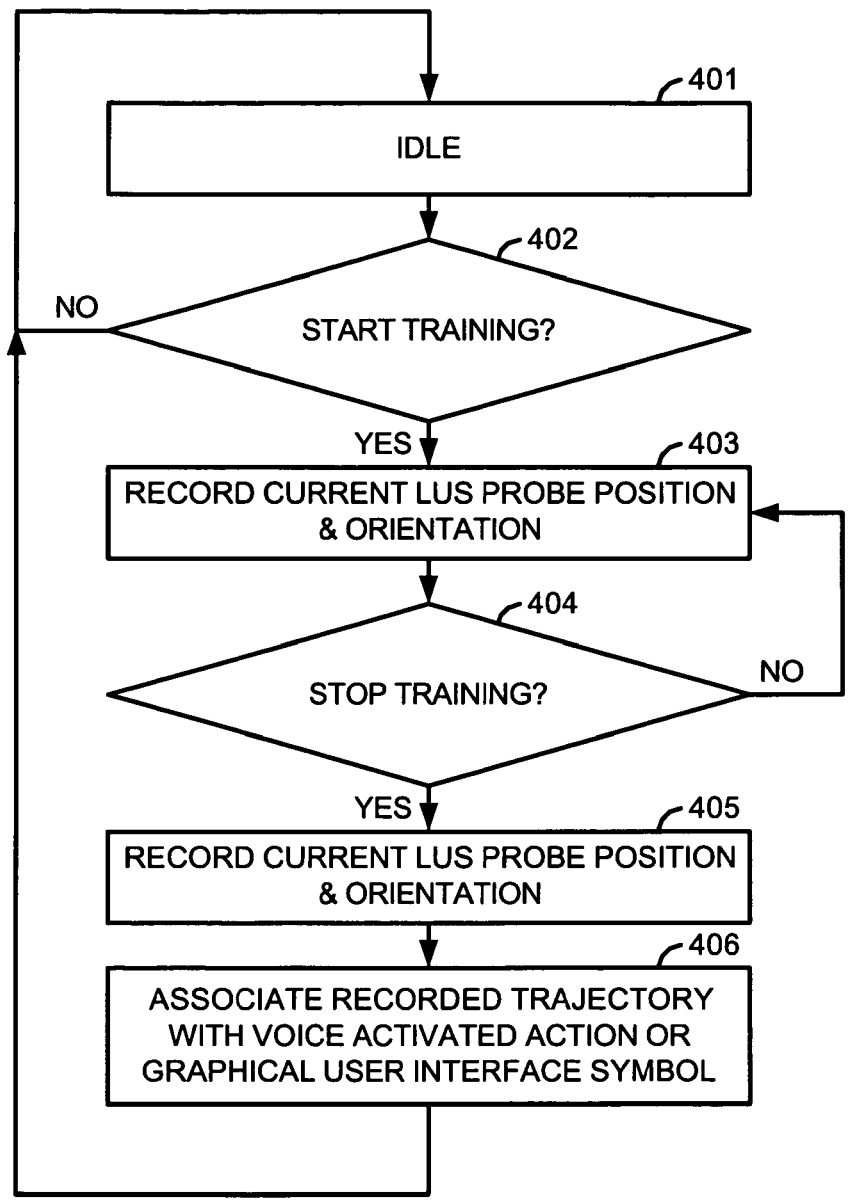
FIG. 4 illustrates a flow diagram of a method for training a LUS robotic surgical system to robotically move a LUS probe in a trained manner upon command, utilizing aspects of the embodiments of the invention.

FIG. 4 illustrates, as an example, a flow diagram of a method for training the auxiliary controller 242 (i.e., providing it with stored instructions) to cause the LUS probe 150 to be robotically moved in the trained manner upon command, in order to capture a sequence of 2D ultrasound image slices of an anatomic structure, which are used by the auxiliary controller 242 to generate a 3D computer model of the structure. Prior to performing the training, the control switch mechanism 231 is placed in its second mode so that the surgeon may move the LUS probe 150 for training purposes by manipulating the master input device 108. After performing training, the control switch mechanism 231 is then placed back into its first or normal mode so that the surgeon may manipulate the tool 139 to perform a minimally invasive surgical procedure using the master input device 108.

In process 401, the training module is initially idle (i.e., it is not being executed by the processor 102). In process 402, the processor 102 (or a training module agent running in the background) may periodically check whether a start of training indication is received. Alternatively, the start of training indication may act as an interrupt which initiates running of the training module. The start of training indication may be initiated by a surgeon through a recognized voice command, selection of a training option on a graphical user interface displayed on the master display 104, a switch mechanism that may physically be located on the corresponding master Control Input 108 or other convenient location accessible to the surgeon, or any other conventional means.

After the start of training indication is detected, in process 403, the training module records or stores the current LUS probe 150 position and orientation, and periodically (or upon surgeon command) continues to do so by looping around processes 403 and 404 until a stop training indication is detected or received. The stop training indication in this case may also be initiated by the surgeon in the same manner as the start of training indication, or it may be initiated in a different, but other conventional manner. After the stop training indication is detected or received, a last position and orientation of the LUS probe 150 is recorded or stored.

Between the start and stop of training, the surgeon moves the LUS probe 150 and the processor 102 stores its trajectory of points and orientations so that they may be retraced later upon command. In one type of training, the surgeon moves the LUS probe 150 back and forth near an anatomic structure in order to capture a sequence of 2D ultrasound image slices from which a 3D version (or computer model) of the anatomic structure may be rendered by the processor 102. In another type of training, the surgeon move the LUS probe 150 once or more times along the surface of the anatomic structure in order to capture a different sequence of 2D ultrasound image slices from which a 3D version (or computer model) of the anatomic structure may be rendered by the processor 102.

Although described as recording the positions and orientations of the LUS probe 150, in practice, the active joint positions of its slave arm 124 are stored instead since their measurements are directly obtainable through encoders attached to each of the joints and their positions correspond to the LUS probe 150 positions and orientations.

After storing the trajectory of positions and orientations of the LUS probe 150 in the memory 240, the trajectory is then associated with a means for the surgeon to command the auxiliary controller 242 to move the LUS probe 150 in the desired fashion. For example, the trajectory may be associated with a voice command which upon its detection, the auxiliary controller 242 causes the slave arm 124 to move the LUS probe 150 back and forth along the stored trajectory of positions and orientations. Likewise, the trajectory may also be associated with a user selectable option on a graphical user interface displayed on the master display 104, or it may be associated with a switch mechanism such as a button or unused control element on the master input device 108. It may also be associated with the depression of the foot pedal 106, so that the auxiliary controller 242 causes the slave arm 124 to move the LUS probe 150 back and forth along the stored trajectory of positions and orientations as long as the foot pedal 106 is being depressed, and stops such motion once the surgeon takes his or her foot off the foot pedal 106.

Figure 5:
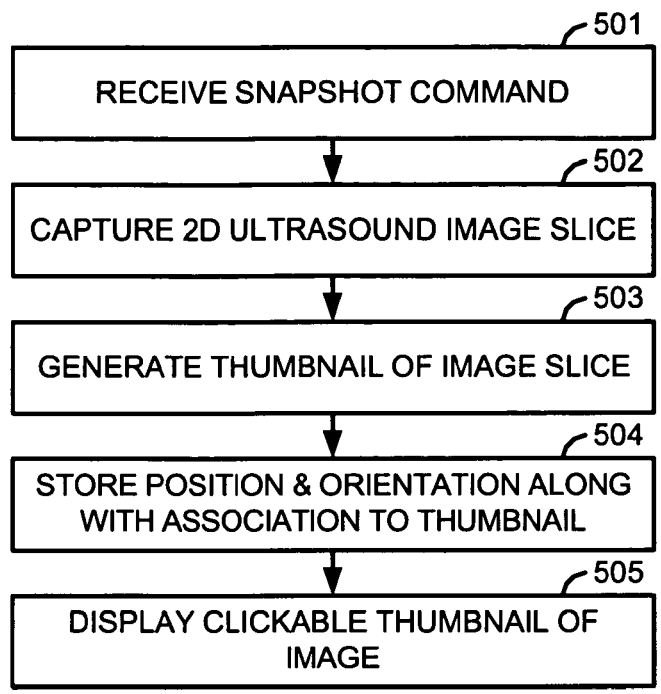
FIG. 5 illustrates a flow diagram of a method for generating a clickable thumbnail image that allows a user to command that a LUS probe be automatically moved to a position and orientation from which the image was captured, utilizing aspects of the embodiments of the invention.

FIG. 5 illustrates, as an example, a flow diagram of a method for generating clickable thumbnail images corresponding to LUS probe 150 positions and orientations that are stored in memory 240, so that when the surgeon clicks on one of the thumbnail images, the auxiliary controller 242 causes the slave arm 124 to move the LUS probe 150 to its stored position and orientation. This allows the surgeon to move the LUS probe 150 to see different views of an anatomic structure while the control switch mechanism 231 is in its first or normal mode. Thus, the surgeon can continue to perform a minimally invasive surgical procedure by manipulating tool 139 using the master input device 108. The method may then be combined with that described in reference to FIG. 4 in order to generate a sequence of 2D ultrasound image slices starting from that position and orientation, from which the auxiliary controller 242 may generate a 3D computer model rendition of the anatomic structure.

Prior to performing the method, however, the control switch mechanism 231 is placed in its second mode so that the surgeon may move the LUS probe 150 into the desired positions and orientations by manipulating the master input device 108. After generating the clickable thumbnail images, the control switch mechanism 231 is then placed back into its first or normal mode so that the surgeon may manipulate the tool 139 to perform the minimally invasive surgical procedure using the master input device 108.

In process 501, the auxiliary controller 242 receives a snapshot command from the surgeon. The snapshot command may be, for example, a voice command, graphical user interface selection, or switch position. In process 502, the auxiliary controller 242 causes the LUS probe 150 to capture a 2D ultrasound image slice, and in process 503, a thumbnail of the image is generated. The thumbnail in this case may include a simple JPEG or GIF file of the captured image. In process 504, the current position and orientation of the LUS probe 150 is stored in memory 240 along with information of its association with the thumbnail. In process 505, a clickable version of the thumbnail is displayed on the master display 104, so that the surgeon may command the auxiliary controller 242 to cause the LUS probe to be positioned and oriented at the stored position and orientation at any time upon clicking with his or her mouse or other pointing device on the clickable thumbnail. The surgeon may then move the LUS probe 150 to other positions and/or orientations, and repeat processes 501-505 to generate additional thumbnail images.

Figure 6:
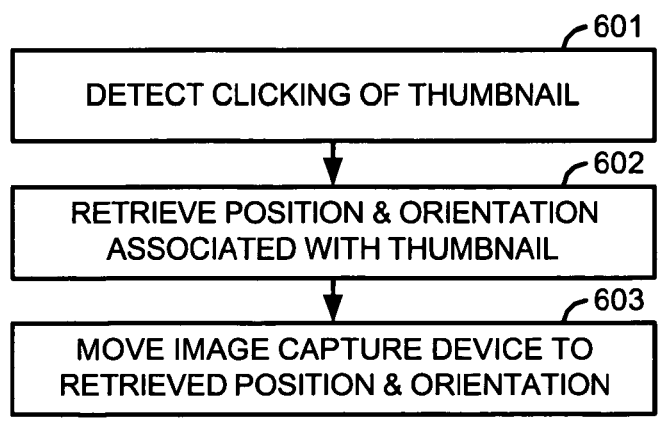
FIG. 6 illustrates a flow diagram of a method for automatically moving s LUS probe to a position and orientation associated with a clickable thumbnail image, utilizing aspects of the embodiments of the invention.

FIG. 6 illustrates, as an example, a flow diagram of a method for automatically moving the LUS probe 150 to a position and orientation associated with a clickable thumbnail upon command to do so by a surgeon while performing a minimally invasive surgical procedure using tool 139. In process 601, the clicking of a thumbnail generated by the method described in reference to FIG. 5 is detected by, for example, a conventional interrupt handling process. Upon such detection, in process 602, the auxiliary controller 242 is instructed by, for example, stored instructions corresponding to the interrupt handling process, to retrieve the position and orientation stored in memory 240 which is associated with the thumbnail. The auxiliary controller 242 then causes the LUS probe 150 to move to that position and orientation by appropriately controlling slave arm 124 in process 603. Thus, the surgeon is able to move the LUS probe 150 to a desired position without having to change modes of the control switch mechanism 231 and halt operation of the tool 139 until the LUS probe 150 is moved.

Virtual Fixtures

The processor 102 may generate a virtual fixture, such as a guidance virtual fixture or a forbidden region virtual fixture. To generate the virtual fixture, local kinematic constraints on the slave arm manipulating the tool may be specified by providing a table of constraints. Generally, a virtual fixture can limit movement of a surgical instrument or tool. For example, a guidance virtual fixture may be generated to assist in electronically constraining a tool to travel over a predetermined path. A forbidden region virtual fixture may be generated to A variety of types and shapes of virtual fixtures may be generated to limit movement of a minimally invasive surgical tool such as virtual planes, virtual chamfers, virtual springs, detents, etc. With these virtual fixtures based on position in mind, virtual dampers may be generated by adding velocity terms.

Figure 7:
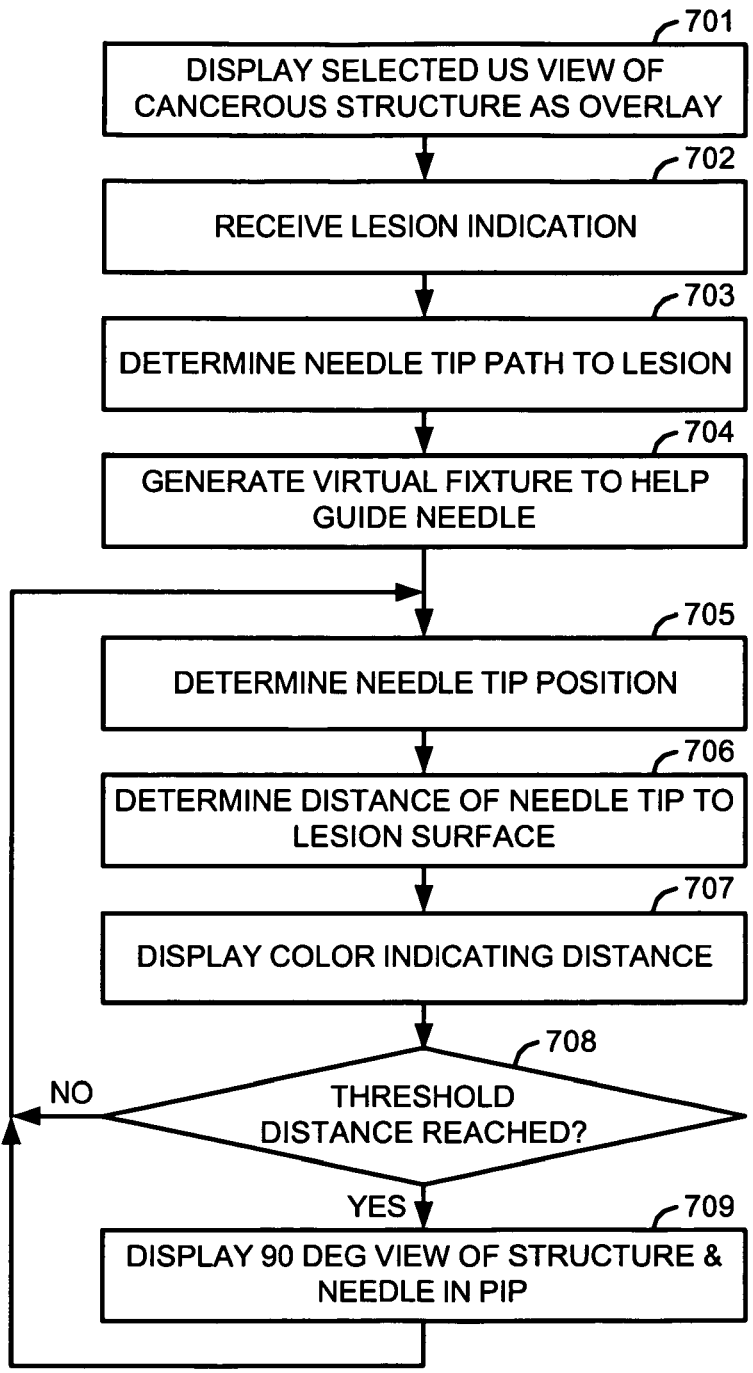
FIG. 7 illustrates a flow diagram of a method for robotically assisted needle guidance to a marked lesion of a cancerous structure, utilizing aspects of the embodiments of the invention.

FIG. 7 illustrates, as an example, a flow diagram of a method for robotically assisted needle guidance and penetration into a marked lesion of a cancerous structure, which allows appreciation for the aspects of robotic assisted LUS described herein. In process 701, a selected 2D ultrasound image slice view of a cancerous structure such as a liver is displayed at the proper depth on the master display 104 as an overlay to a 3D camera view of the cancerous structure. The selected 2D ultrasound image slice view may be a frontal view or an inner slice view as taken from a previously generated 3D ultrasound computer model of the cancerous structure.

Figure 8:
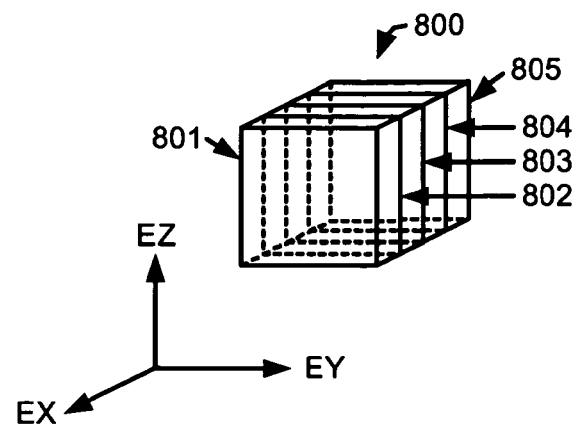
FIG. 8 illustrates a perspective view of a 3D ultrasound image of an anatomic structure in a camera reference frame with selectable 2D image slices as used in a medical robotic system utilizing aspects of the embodiments of the invention.
Figure 9:
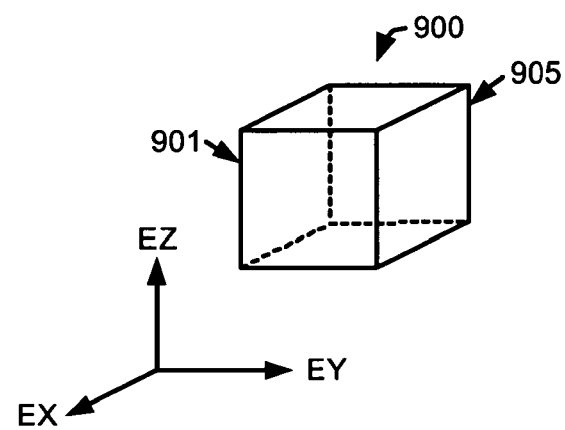
FIG. 9 illustrates a perspective view of a 3D camera view of an anatomic structure in a camera reference as used in a medical robotic system utilizing aspects of the embodiments of the invention.
Figure 10:
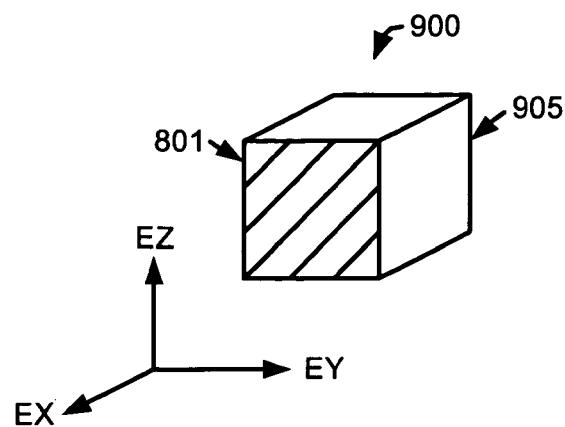
FIG. 10 illustrates a perspective view of a frontal 2D slice of a 3D ultrasound view of an anatomic structure that overlays a 3D camera view of the anatomic structure, as displayable in a medical robotic system utilizing aspects of the embodiments of the invention.
Figure 11:
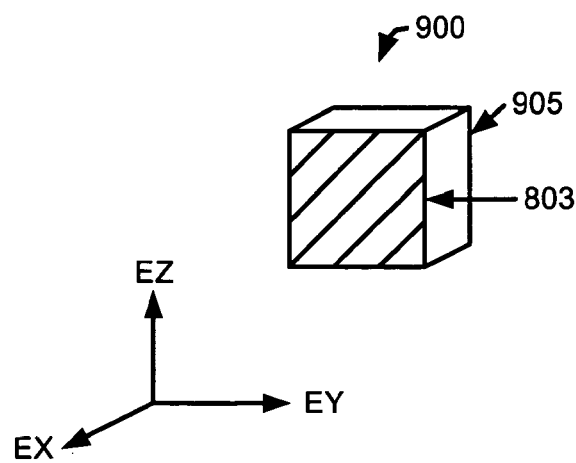
FIG. 11 illustrates a perspective view of an inner 2D slice of a 3D ultrasound view of an anatomic structure that overlays a 3D camera view of the anatomic structure, as displayable in a medical robotic system utilizing aspects of the embodiments of the invention.

As an example clarifying the process 701, FIG. 8 illustrates a simplified perspective view of a 3D ultrasound computer model 800 of the cancerous structure, which has been generated, for example, using the method described in reference to FIG. 4, and has been translated into the camera reference frame (EX, EY, EZ). FIG. 9, on the other hand, illustrates a simplified perspective view of a 3D camera view 900 of the cancerous structure as taken by the stereoscopic endoscope 140. If the surgeon selects a frontal slice 801 of the 3D ultrasound computer model 800 to be viewed as an overlay to the 3D camera view 900, then the overlay will appear as shown in FIG. 10. On the other hand, if the surgeon selects one of the inner slices 802-804 of the 3D ultrasound computer model 800, such as inner slice 803, to be viewed as an overlay to the 3D camera view 900, then the overlay will appear as shown in FIG. 11 with the 2D ultrasound image slice 803 displayed at the proper depth. To avoid confusion, the portion of the 3D camera view above that depth is made transparent.

Alternatively, the surgeon may manually control movement of the LUS probe 150 so that 2D ultrasound image slices captured by it appear as emanating in proper perspective and direction from the 3D camera image of the LUS probe 150 in the master display 104. Preferably, the emanated 2D image slices being displayed in the master display 104 do not occlude the anatomic structure being probed. This manual approach may be particularly useful to the surgeon for quickly spotting lesions in the anatomic structure.

In process 702, the surgeon marks lesions on the cancerous structure displayed as a result of process 701. Each marked lesion is preferably marked using a designated color in order to clearly show that the surgeon has already identified it, thereby avoiding double counting. The location in the camera reference frame (EX, EY, EZ) of each marked lesion is stored in memory 240, and in process 703, the processor 102 determines an optimal needle tip path to that location.

In process 704, the processor 102 generates a virtual fixture to help guide the needle to the marked lesion. To generate the virtual fixture, local kinematic constraints on the slave arm manipulating the needle tool may be specified by providing a table of constraints of the form:

$$(\vec{x} - \vec{x}_0)^T A_K (\vec{x} - \vec{x}_0) + \vec{b}_K (\vec{x} - \vec{x}_0) \leq c \quad (2)$$

where $\vec{x}$ represents, in simplified terms, the current 6 DOF kinematic pose of a master arm, or, in more general terms, a parameterization of a Cartesian pose F linearized about some nominal pose $F_0$ so that $(\vec{x} - \vec{x}_0) \sim F_0^{-1} F$. The tables are to be updated periodically based on visual feedback, user interaction, etc.

As can be appreciated, equation (2) can be easily checked and enforced.

Similarly, a simple table-driven interface for surgeon interaction forces can be implemented approximately as follows:

$$\begin{aligned}
&\vec{f} \leftarrow 0; y \leftarrow \vec{x} - \vec{x}_0; \\
&\text{for } k \leftarrow 1 \text{ to } N \text{ do} \\
&\quad \{\varepsilon \leftarrow \vec{y}^T C_K \vec{y} + \vec{d}_K \vec{y} - e_K; \\
&\quad \text{if } \varepsilon > 0 \text{ then } \{\vec{g} \leftarrow 2C_K \vec{y} d_k; \vec{f} \leftarrow \vec{f} + f(\varepsilon)\vec{g} / \|\vec{g}\|; \}; \\
&\};
\end{aligned} \quad (3)$$

output $\vec{f}$ (after limiting & spacing)

where ε corresponds, roughly, to a distance from a surface in state space and the function f (ε) corresponds to a (non-linear) stiffness.

The above formulation suffices to support a variety of virtual chamfers, virtual springs, detents, etc. The formulation can be easily extended to virtual dampers by adding velocity terms.

Now, more particularly, in the present case where it is desired to help aim an injection needle at a target in a live ultrasound image, let:

$$\vec{P}_{TROCAR} = \text{position where needle enters patient} \quad (4)$$
$$= \text{"RCM" point for needle insertion arm}$$

$$R_{NEEDLE} = R_0 R(\vec{\alpha}) = \text{orientation of needle arm} \quad (5)$$

$$\vec{\alpha} = \text{vector representation for small rotation} \quad (6)$$

$$F_{LUS} = [R_{LUS}, \vec{P}_{LUS}] = \text{pose of LUS sensor} \quad (7)$$

$$V_{TARGET} = \text{position of target wrt LUS sensor} \quad (8)$$

Then the basic constraint is that the needle axis (which is assumed for this example to be the $\vec{Z}$ axis of the needle driver) should be aimed at the target lesion, which will be given by $F_{LUS} \vec{V}_{TARGET}$. One metric for the aiming direction error will be:

$$\varepsilon_{AIMING}(\vec{\alpha}) = \left\|(R_{NEEDLE}\vec{z}) \times (F_{LUS}\vec{v}_{TARGET} - \vec{P}_{TROCAR})\right\|^2 \quad (9)$$

$$= \left\|(R(\vec{\alpha})\vec{z}) \times R_0^{-1}(F_{LUS}\vec{v}_{TARGET} - \vec{P}_{TROCAR})\right\|^2$$

which can be approximated as a quadratic form in $\vec{\alpha}$ and converted to a virtual fixture using the method described above. Similarly, if the position of the needle tip is $\vec{P}_{TIP}$, the penetration depth beyond the LUS target will be given by:

$$\varepsilon_{BEYOND} = (R_0 R(\vec{\alpha})\vec{z}) \bullet (F_{LUS} \vec{v}_{TARGET} - \vec{P}_{TIP}) \quad (10)$$

which can easily be transcribed into a virtual detent or barrier preventing over-penetration. Alternatively, a simple spherical attractor virtual fixture can be developed to minimize $\|F_{LUS} \vec{v}_{TARGET} - \vec{P}_{TIP}\|$.

In process 705, the processor 102 determines the needle tip position as it moves towards the target lesion, and in process 706, the processor 102 determines the distance between the needle tip position and the target lesion. The needle tip position may be determined from the slave arm kinematics and/or through visual tracking in the camera image.

In process 707, the color of the lesion or some other object in the display changes as the needle tip gets closer to the target. For example, the color may start off as blue when the needle tip is still far away from the target, and it may change through color spectrum so that it becomes red as it nears the target. Alternatively, a bar graph or other visual indicator may be used to give a quick sense of the distance.

In process 708, a determination is made whether the distance has reached a threshold distance (usually specified as some distance close to or even at the surface of the target lesion). If the threshold has not been reached, then the method loops back to process 705 and continually repeats processes 705-708 until the threshold is reached. Once the threshold is reached, in process 709, a 90 degree view of the cancerous structure and the approaching needle is shown in a picture-in-picture window of the master display 104. The method may then go back to process 705 and repeat processes 705-708 as the needle penetrates the cancerous structure or withdraws back to its start position.

Virtual fixtures, along with other objects, may be defined or manipulated through an interactive user interface at a surgeon console as more fully described below.

Interactive User Interface

Overview

Robotic surgical systems allow a surgeon to operate in situ. The benefits of non invasive surgery are well documented and continuing improvements in laparoscopic surgery are advancing the medical profession in a new and exciting direction. One of the many challenges of laparoscopic surgery is working within the confined space of a body cavity. Surgical instruments, endoscopes, ultrasound probes, etc. need to be directed with precision and celerity, or risk complications from accidental tissue damage and extended surgery times. Thus robot assisted laparoscopic surgery may benefit from an interactive user interface that provides a unified assistive environment for surgery. The interactive user interface integrates robotic devices, preoperative and intra-operative data sets, surgical task models, and human-machine cooperative manipulation. A surgical assistant workstation (SAW) for teleoperated surgical robots can enhance the capabilities of robot-assisted laparoscopic surgery by providing fully integrated image guidance and data-enhanced intra-operative assistance to the surgical team and to the surgeon in particular.

Master tool manipulators (MTM) (e.g., master tool manipulators 107-108 illustrated in FIG. 1) are input devices of a surgical console (e.g., surgeon console C illustrated in FIG. 1) that constitute the primary means of input and control for the surgeon. Details of a master tool manipulator are described in U.S. Pat. No. 6,714,939 entitled MASTER HAVING REDUNDANT DEGREES OF FREEDOM, issued on Mar. 30, 2004 to Salisbury et al. which is incorporated herein by reference.

The master tool manipulators (MTMs) can be switched to operate in different modes. U.S. Pat. No. 6,459,926 entitled REPOSITIONING AND REORIENTATION OF MASTER/SLAVE RELATIONSHIP IN MINIMALLY INVASIVE TELESURGERY, issued on Oct. 1, 2006 to William C. Nowlin et al. incorporated by reference, provides further details as to how the master tool manipulators (MTMs) (also referred to herein as master input devices) can be switched to operate in different modes.

In a following mode, the patient-side slave manipulators (PSMs) (also referred to sometimes as robotic arms) follow the motion of the master tool manipulators and are teleoperated. That is, the MTMs may couple motion into the patient-side slave manipulators. A third patient-side slave manipulator (PSM-3) can be activated by tapping the clutch pedal. This allows the surgeon to toggle between PSM-3 and either PSM-1 or PSM-2, depending on which side PSM-3 is positioned.

In a master clutch mode, the master clutch pedal is depressed and the system is taken out of following mode. The PSM motion is no longer coupled to MTM motion. During surgery, this allows the operator to re-center the MTMs within their range of motion, and thus increase the surgical workspace.

In a camera control mode, the camera clutch pedal is depressed and the PSMs are taken out of following mode and control is transferred to the endoscopic control manipulator (ECM) for camera repositioning.

The SAW framework adds another alternative mode (referred to as masters-as-mice mode) for the MTMs that overlaps with master clutch mode, allowing the surgeon to interact with the SAW graphical user interface (GUI). In this mode, each MTM operates as a 3D mouse, such that it can be used to position a graphical cursor overlaid on the stereo display console, while gripper open/close motions are used to emulate click and drag operations. In this way, the surgeon is able to interact with graphical objects and menus displayed by the SAW application. This mode is called a masters-as-mice (MaM) mode.

When using the surgeon or surgical console, the master tool manipulators are used as input devices for the graphical user interface within the surgical console. The MaM mode overlaps with the existing master clutch mode of the surgeon console in the following way:

---

Process MTM Event(Event)

1  if Event == MASTER CLUTCH PRESSED
2    then  InitMTM Pos = GetMTMPos( )
3    Wait(3 seconds)
4    ClutchState = GetMasterClutchState( )
5    MTM Pos = GetMTMPos( )
6    if (ClutchState == PRESSED) and ((MTM Pos – InitMTM Pos) < epsilon)

-continued

| | Process MTM Event(Event) |
|---|---|
| 7 | then EnterSAWConsoleMode( ) |
| 8 | else return |
| 9 | else return |

While in Saw Console Mode (MaM and/or GUI modes) the position and orientation of the MTM is used to drive the 3D pointer, while its gripper handle is used as a button.

Figure 12:
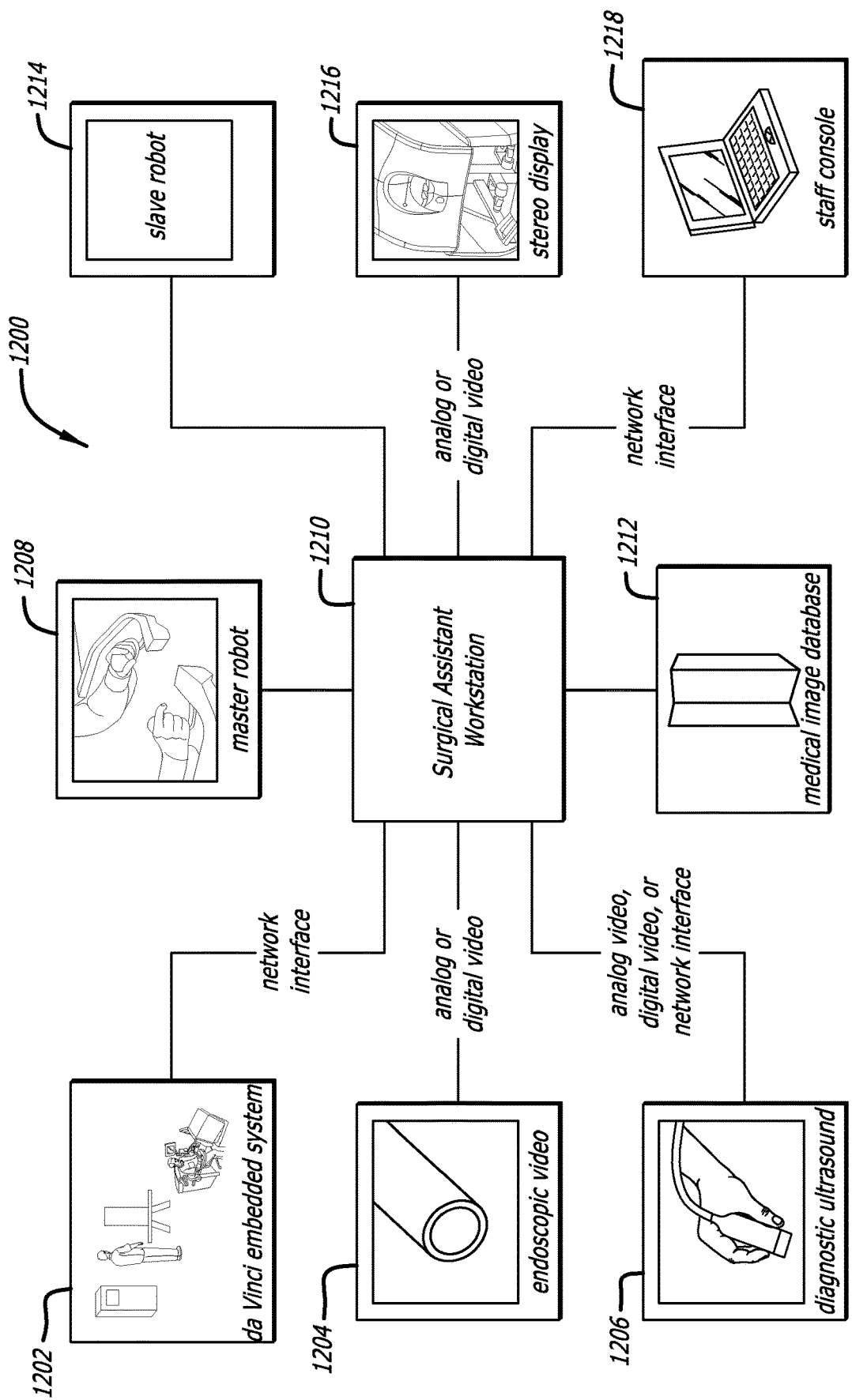
FIG. 12 is a diagrammatic physical view of a subsystem architecture for a surgical assistant workstation.

A diagrammatic view of a teleoperated surgical system including a surgical assistant workstation (SAW) is shown in FIG. 12. Deployment of the SAW framework is application specific. FIG. 12 shows a generic deployment view that illustrates a number of common components and sub-systems.

A user interface 1202 of a teleoperated surgical system is connected via a communication network to a SAW 1210. SAW 1210 will support at least two types of video sources, namely: stereo endoscopy 1204 and ultrasound 1206. Stereo endoscopy may be provided by two laparoscopic cameras (endoscopes or endoscopic cameras) transmitting independent video images to stereo displays 1216, such as at the master display 104 of the console C illustrated in FIG. 1 or head mounted displays or visors. Ultrasound 1206 may be an ultrasound probe attached to the end of a wristed robotic surgical arm inserted into the surgical site. Stereo endoscopy 1204 may be connected to SAW 1210 by analog or digital video. In addition to analog or digital video, ultrasound 1206 may be connected to SAW 1210 by network interface. Video images may also be provided by a medical image database 1212 connected to the SAW 1210. The medical image database 1212 is a source of medical images, models, surgical plans, and other application data. For example the medical images database could include preoperative images or a clinical Picture Archiving and Communication system (PACS).

Master robot 1208 and slave robot 1214 are research-grade interface devices generally with robotic surgical arms operating various surgical tools. Examples of the master robot 1208 include CISST MTMs and steady hand Robot. Examples of slave robot 1214 include CISST PSMs, and a snake robot.

Figure 13:
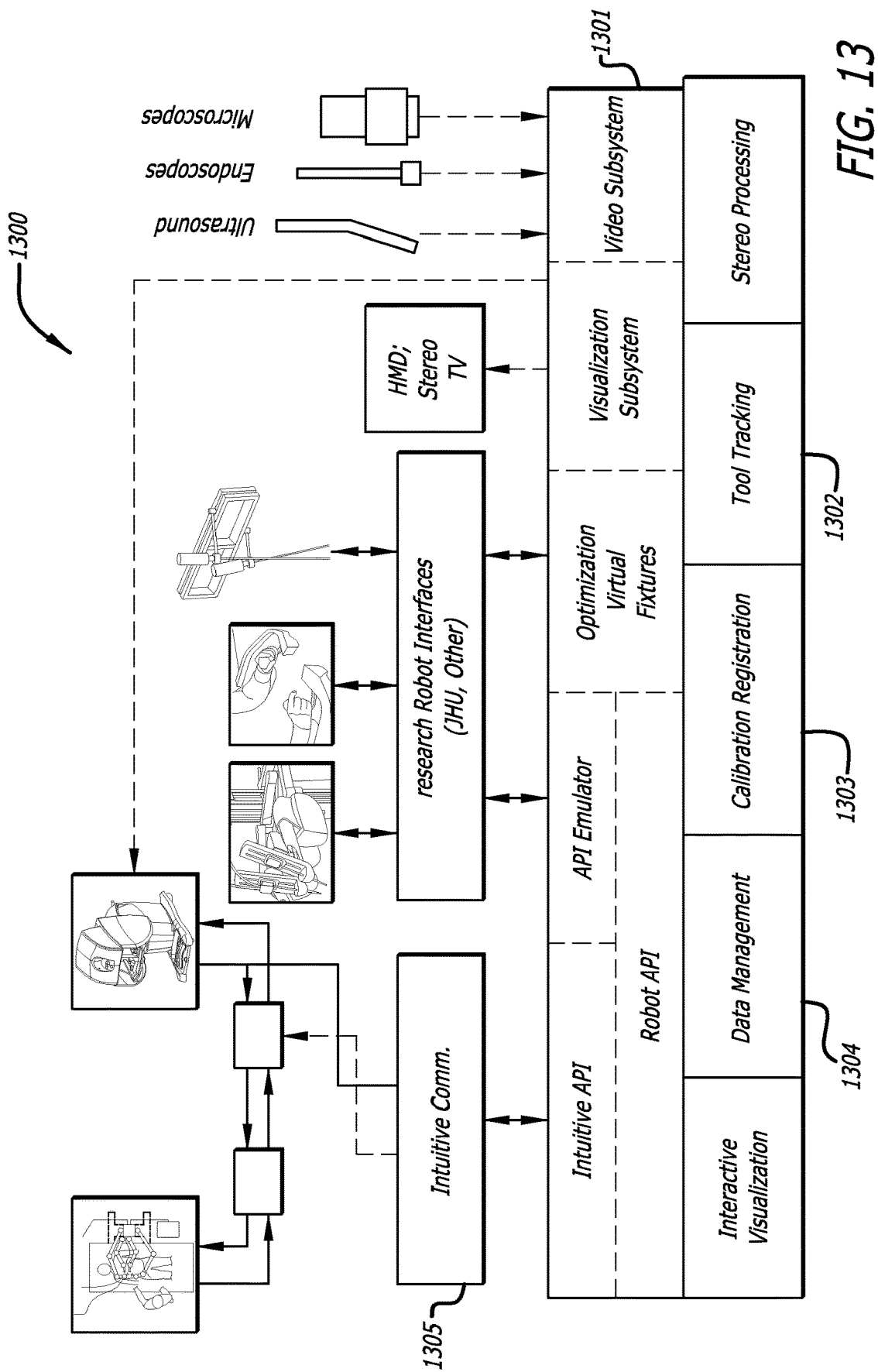
FIG. 13 is a diagrammatic view of a surgical assistant workstation for teleoperated surgical robots architecture.

FIG. 13 is a diagrammatic illustration of a surgical assistant workstation (SAW) system architecture 1300 for teleoperated surgical robots. The SAW system architecture 1300 includes multiple interconnected subsystems, which are briefly described hereafter. A video subsystem 1301 provides mechanisms for acquiring and processing streams of images, including ultrasound and stereo endoscopic video. Such image processing pipelines can be used to implement tool and tissue tracking algorithms. Tool tracking 1302 is a specialized image processing pipeline provided for tracking the positions of surgical instruments using a combination of kinematic and stereo vision feedback.

Another subsystem is the calibration and registration subsystem 1303. This subsystem may provide software tools for determining device calibration, as well as methods for computing coordinate transformations between data sources (i.e., registration). Such tools may include kinematic calibration, camera calibration, ultrasound calibration, pre-operative and intra-operative image registration, video registration, etc.

The data management subsystem 1304 provides means to both import and export archived application data, including medical images, models, surgical plans and annotations. In its implementation, this subsystem could accommodate data in various formats, including medical reality markup language (MRML), DICOM and clinical PACS.

The communication interface 1305 facilitates interactive manipulation and visualization of 2D and 3D data objects, including medical images and video, directly within the surgical console. A 3D graphical user interface manages user interaction from various input devices (including the master tool manipulators MTMs) and renders a menu system and graphical overlays to the stereo display of the surgical console. A 3D brick manager (as opposed to a 2D Window Manager) provides application-level widgets and interaction logic. A secondary user interface, called the staff console, will be provided to support the surgical interface. This is a conventional 2D interface that is intended for planning and monitoring outside of the surgical console.

Figure 14:
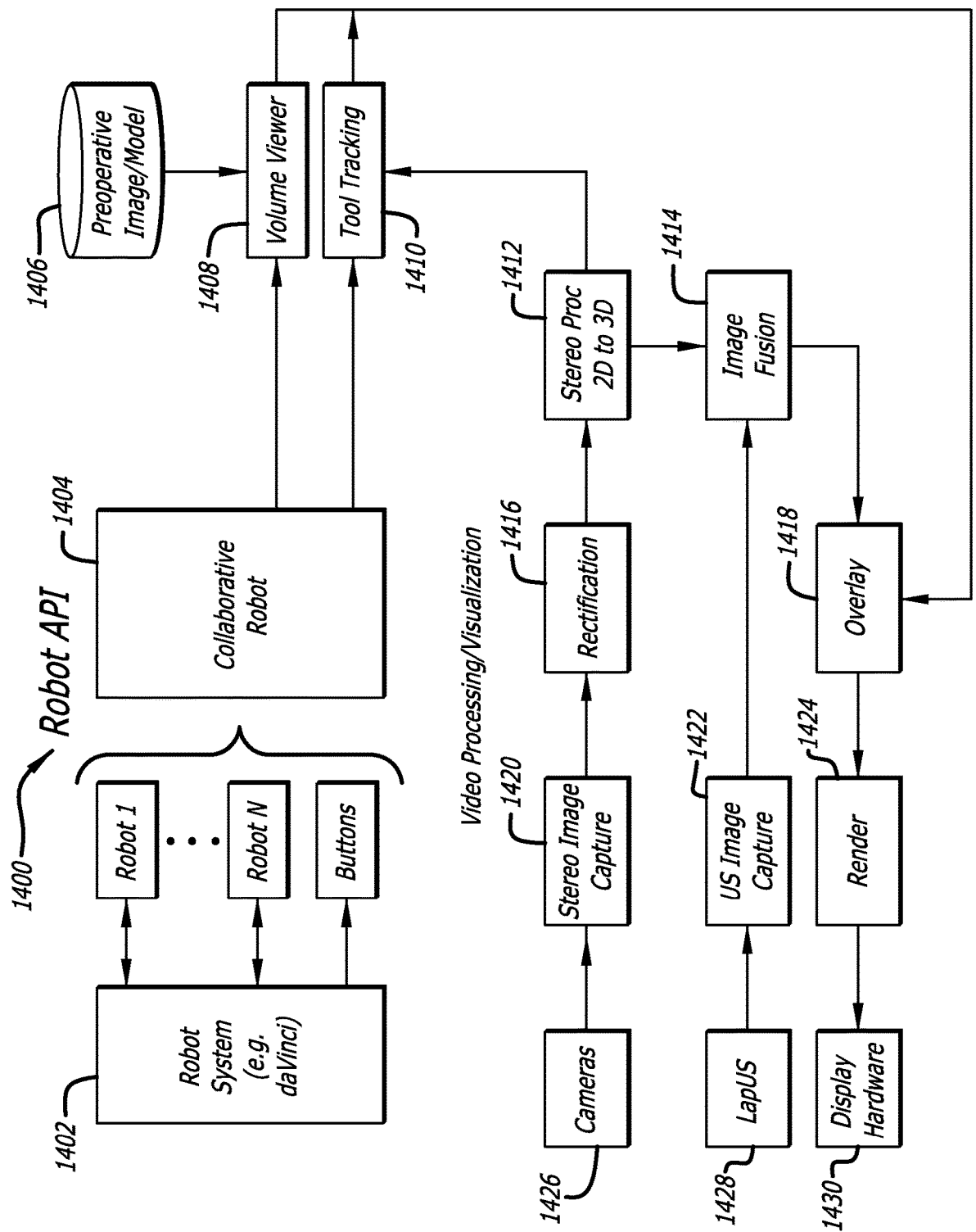
FIG. 14 is a diagrammatic view of an illustrative data flow.

FIG. 14 shows an illustrative data flow diagram, focusing on the robot application program interface (API) and the pipeline for video processing and visualization. This figure also shows the tool tracking and volume viewer subsystems. Although not specifically shown, calibration and registration functions may also be performed.

In FIG. 14, subsystems are shown with arrows illustrating data flow between the various subsystems of the SAW 1400. Robot system block 1402 and collaborative robot block 1404 transmit kinematic motion data to volume viewer block 1408 and tool tracking block 1410. Volume viewer block 1408 also receives preoperative image/model data 1406 from the data management subsystem 1304 in FIG. 13.

In the video processing/visualization pathways, image data from cameras 1426 and LapUS 1428 is captured by their respective image capture modules, stereo image capture module 1420 and ultrasound (US) image capture module 1422. Video image data from the endoscopic cameras 1426 is further rectified in the rectification block 1416 before being coupled into the stereo processor block 1412 for processing from 2D to 3D images. The 3D images of block 1412 are then transmitted to the tool tracking subsystem 1410 and used in conjunction with the kinematic data provided by collaborative robot block 1404 to monitor the surgical tools.

After being captured by the ultrasound (US) image capture module 1422, the LapUS data is transmitted to the image fusion block 1414. The image fusion block 1414 fuses the ultrasound images with the 3D endoscopic images that are then coupled into the overlay block 1418. The overlay block 1418 selectively overlays the graphical user interface and the medical image volume onto the fused ultrasound and endoscopic images. The combined image data including the overlaid graphics and images onto the fused images is coupled to the rendering block 1424 for rendering onto the hardware display 1430.

Figure 15:
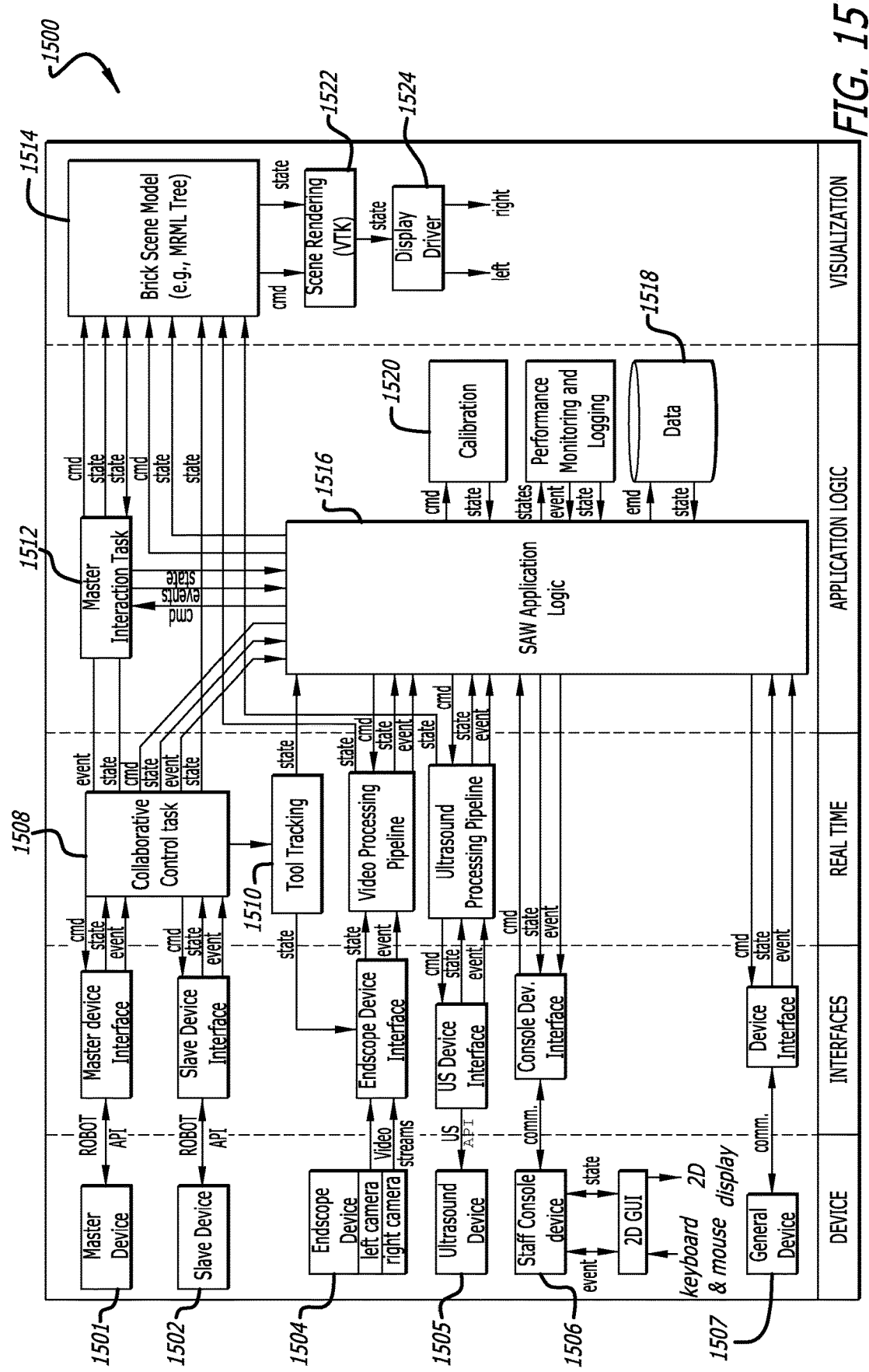
FIG. 15 is a diagrammatic view of a subsystem architecture (logical view).

FIG. 15 is a logical view of the subsystem architecture of SAW 1500. A robot manipulator (master device 1501 and a slave device 1502), image sources (endoscope image source 1504 and ultrasound image source 1505), external consoles 1506 (staff console) and other peripherals 1507 (general) are categorized as devices, and as such are interfaced to the application framework by means of device interfaces. These device-specific blocks create a layer of abstraction between external hardware or software modules in order to present a uniform interface to the application logic.

The collaborative control block 1508 couples the master and slave devices together. In a single-slave, single-master configuration, this block implements teleoperation control. In general, an application may include multiple masters and/or slaves; therefore, the collaborative control block provides a means to coordinate multiple manipulators. It contains a synchronous real-time loop for implementing control systems.

A video processing pipeline is used to implement visual tool/instrument tracking 1510. The visual tool/instrument tracking block 1510 receives state information from the collaborative control block 1508 in order to incorporate kinematic information into the tool tracking algorithm. Exemplary tool tracking algorithms and systems that may be used are described in U.S. patent application Ser. No. 11/130,471 entitled METHODS AND SYSTEM FOR PERFORMING 3-D TOOL TRACKING BY FUSION OF SENSOR AND/OR CAMERA DERIVED DATA DURING MINIMALLY INVASIVE SURGERY, filed on May 16, 2005 by Brian David Hoffman et al.

The master interaction block 1512 facilitates user interaction with menu widgets and graphical scene objects represented by the brick manager 1514. It provides the interface logic between the master manipulators and the brick manager 1514 when in masters-as-mice mode. Typical 2D windowing systems use the mouse input to create events (e.g., motion, click, release events) and bind callbacks to these events. The master Interaction block 1512 provides a similar mechanism for the 3D MTM inputs by querying the state of the manipulators and listening for clutch events. The interaction logic transforms these inputs into pointer motion, button click events and specific behaviors such as object selection, dragging, rotation, resizing, etc.

The brick manager 1514 is the three dimensional analog of a standard window manager, in that it supports 3D user input and interaction with 3D graphical objects, such as image volumes and models, markers, annotations and in-situ video streams. The visual scene that is maintained by the brick manager 1514 is ultimately rendered in stereo for overlay onto the surgical console display. It can be used to provide intraoperative visualization and graphical user interface (GUI). The brick manager 1514 renders the fixed/augmented view into an interactive window the surgeon can interact with. A display driver 1524 drives image data onto the left and right channels of the stereoscopic display.

Application-specific logic is encapsulated in SAW application block 1516 and is defined by the application developer within the scope of the SAW application framework. Once the "master Interaction" component has determined which widget is currently active, all events will be forwarded to the widget and its logical layer. If the application requires a more direct access to the MTMs, the application will be able to access the MTM's state and disable the event forwarding from the master interaction component.

Data block 1518 contains images, text, and other data which can be called by surgeon via the master interaction block 1512 and SAW Application Logic 1516.

System calibration is performed in calibration block 1520. Typical calibration tasks include kinematic calibration of the robot manipulators, calibration of the navigation system, ultrasound calibration, and model to video registration. Calibration block 1520 may also align a video image such as an ultrasound to the coordinate frame of a surgical instrument as seen under an endoscope. Some of these calibrations procedures are described further herein.

Figure 16:
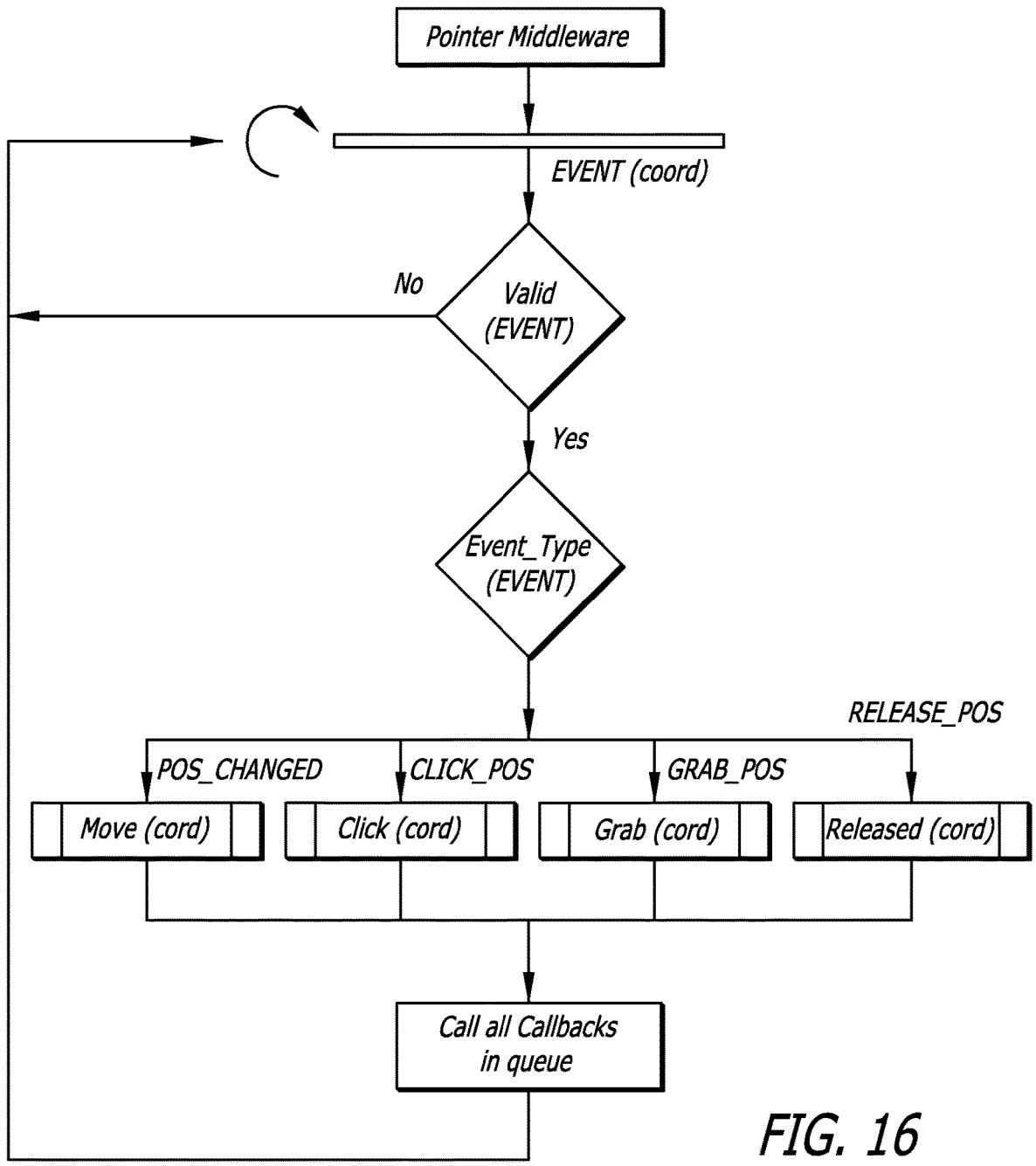
FIG. 16 is a diagrammatic view of basic three dimensional (3D) pointer interaction logic—event handling.
Figure 17:
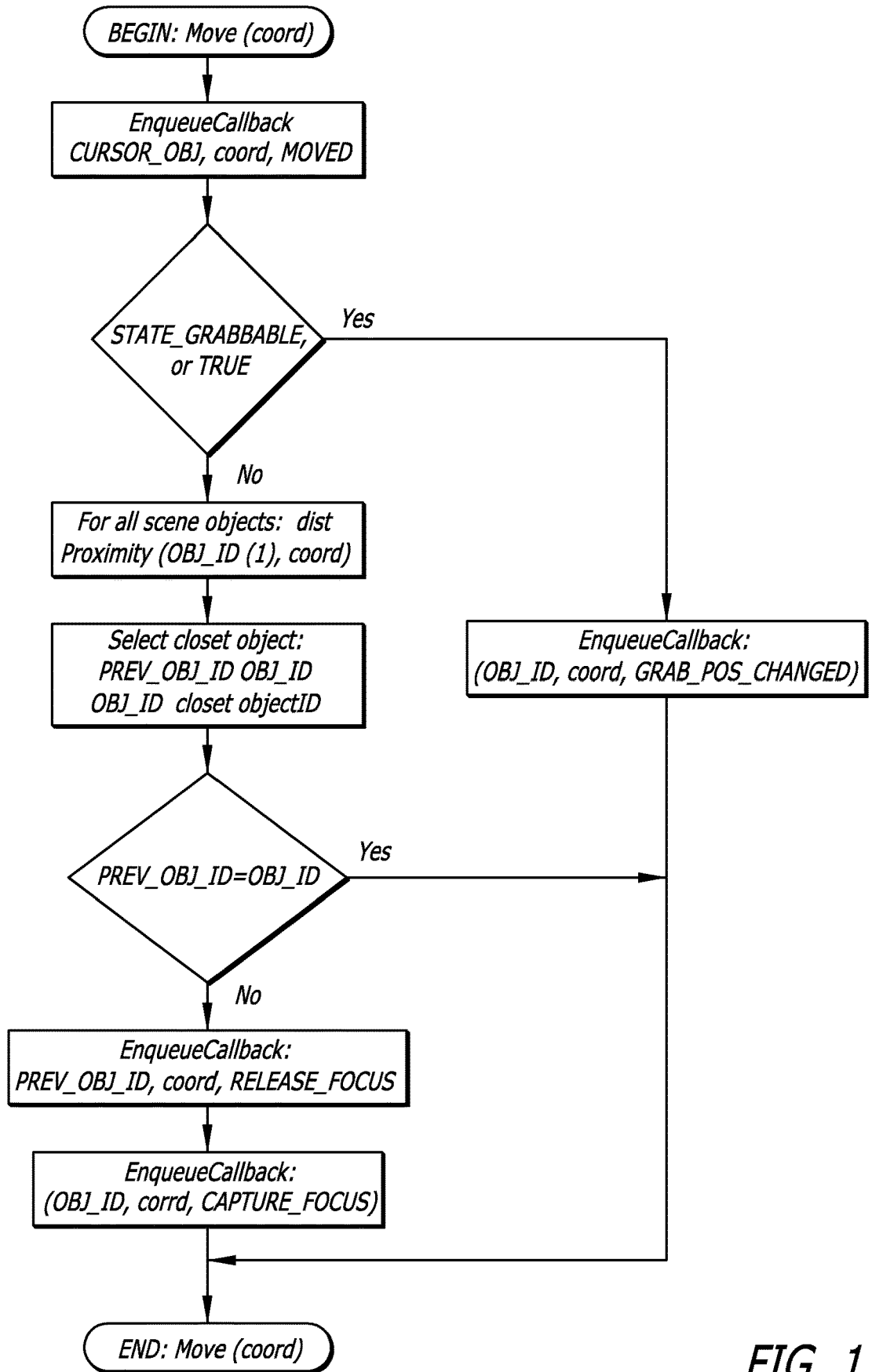
FIG. 17 is a diagrammatic view of basic 3D pointer interaction logic—move event.
Figure 18:
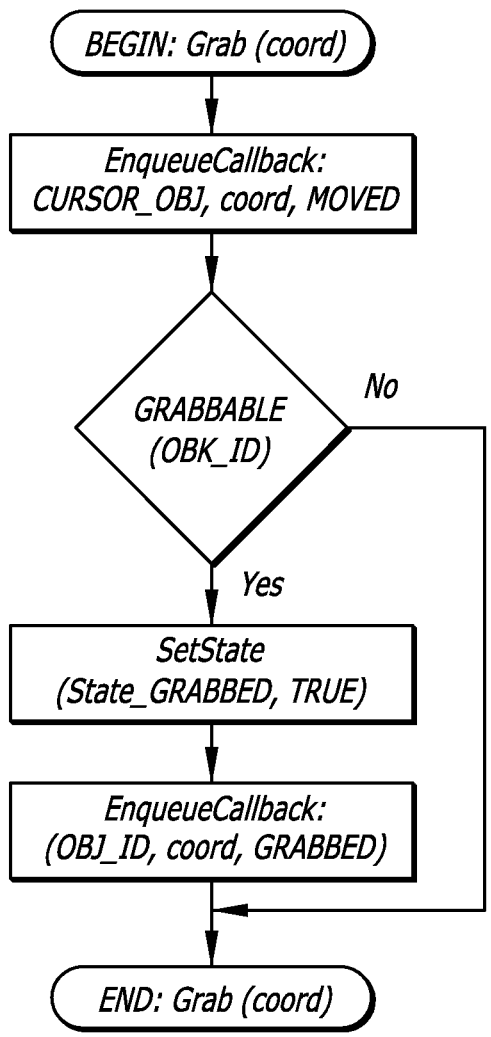
FIG. 18 is a diagrammatic view of basic 3D pointer interaction logic—grab event.

FIGS. 16, 17, and 18 are logic trees for basic 3D cursor interactions. Two events Move and Grab are diagrammed in more detail in FIGS. 17 and 18 respectively.

Figure 19:
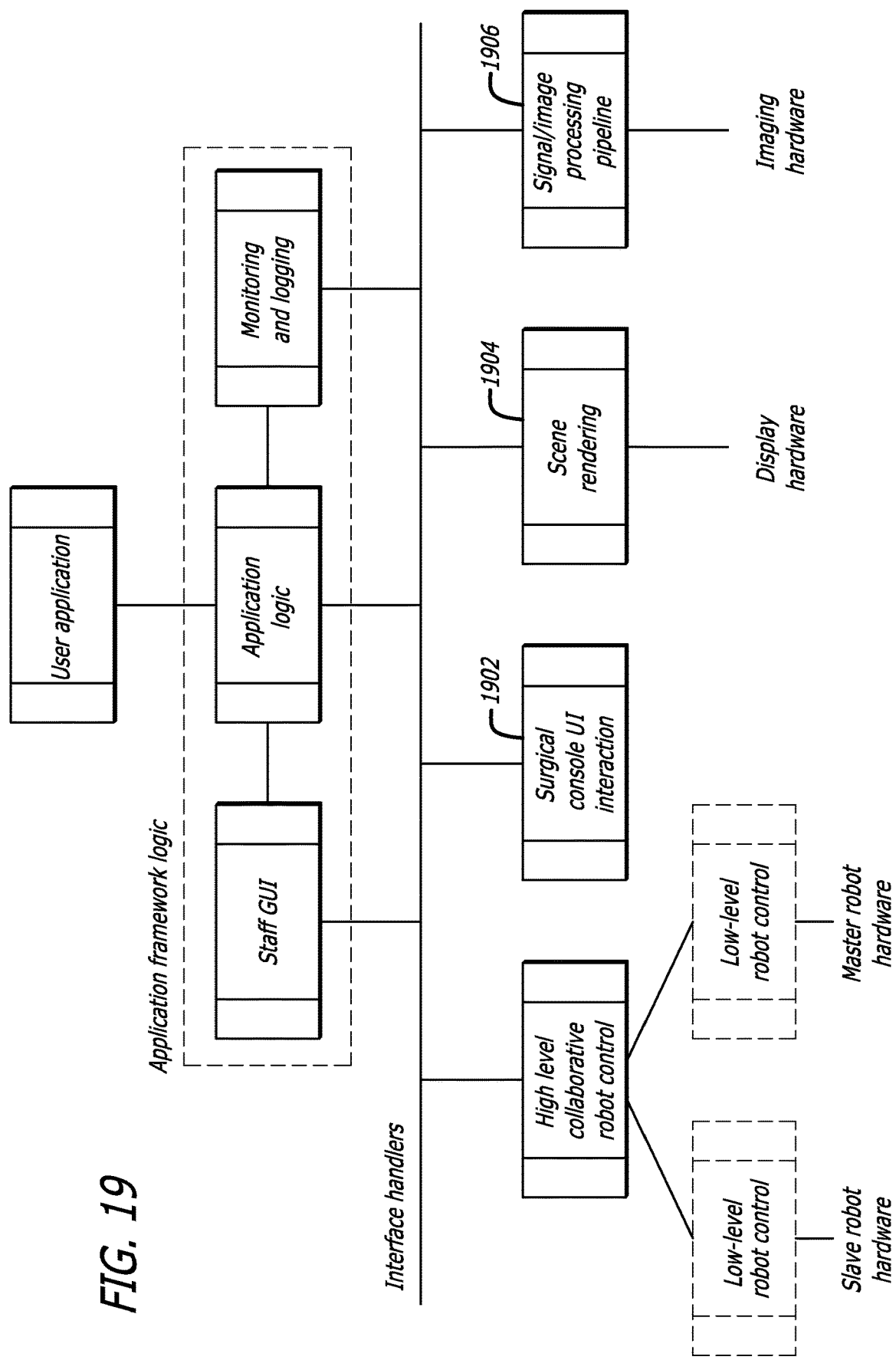
FIG. 19 is a diagrammatic view of a subsystem architecture (process view).

FIG. 19 depicts the concurrent units of execution in the system. In general, these execution units are provided by threads (e.g., multi-threading), rather than by multiple processes. Note, however, that the "low-level robot control" may be provided externally (e.g., when using the research API). In this case, it would be a separate process, possibly on a separate computer. Similarly, signal and image processing pipelines may be distributed as external processes on separate computing hardware.

Surgical console block 1902 is an interactive intraoperative 3D graphical user interface. The GUI may augment the master surgical interface for enhanced image visualization and control by the surgeon. Augmentation is accomplished by video overlay of medical volume data or overlay of live images from a video source such as a LapUS probe or other imaging device. Content specific interactive menus and icons are also placed on the GUI allowing the surgeon to rotate images, pan, or zoom images, and establish virtual operating boundaries for surgical tools.

Scene rendering block 1904 is a graphical rendering pipeline responsible for stereo visualization and overlay in the surgeon's console. In scene rendering block 1904, video signals from a video source such as an ultrasound may be overlaid onto the coordinate frame of a surgical instrument operating in the field of view of the endoscope. Video from the endoscopes are also processed into 3D images and displayed on the surgeon console or head mounted display.

Signal/image processing pipeline 1906 is a processing pipeline that is used for video processing such as instrument tracking and image overlay and other signal processing tasks. This pipeline may include the acquisition of images, video, and signals that originate from external devices or distributed system components. For some applications, computationally demanding or specialized processing may be performed on a dedicated hardware system. Thus, the signal/image processing pipeline 1906 component may also be performed by an external signal processing system.

Figure 20:
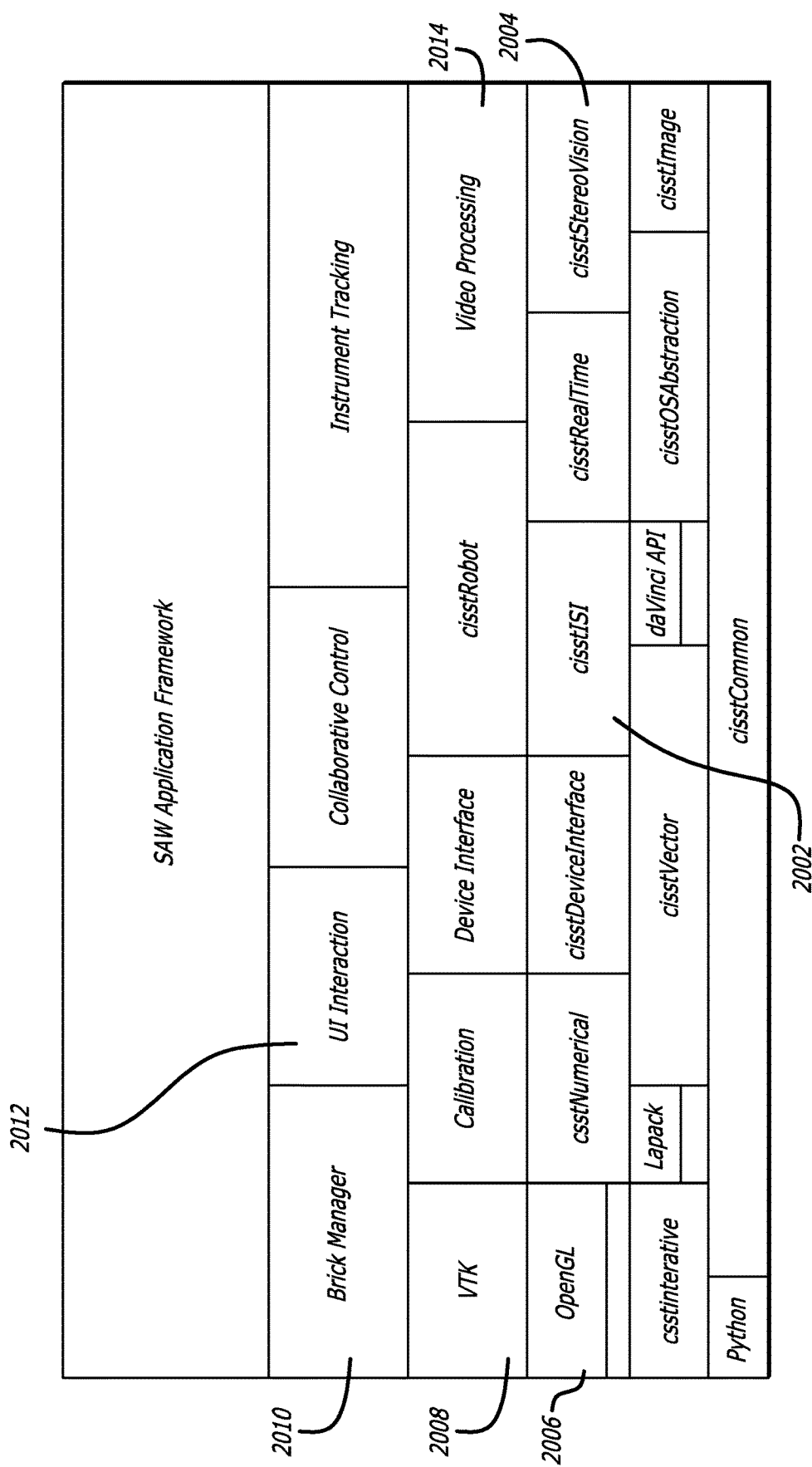
FIG. 20 is a diagrammatic view of a subsystem architecture (development view).

FIG. 20 depicts a hierarchical view of the core SAW software libraries and their dependencies. The bottom rows contain the CISST foundation libraries, as well as external packages such as Python, LAPACK, and the research API. The cisstDevice Interface library includes the abstract base class for all device interfaces, whether Device Tasks or Device Wrappers. Specific device interfaces are derived from this class. Similarly, cisstRobot defines generic robot capabilities, whereas robot-specific implementations are provided by modules such as cisstISI (for the Intuitive Surgical daVinci robot). The figure also shows higher-level functionality such as video processing, instrument tracking, and collaborative robot control. All of this is encompassed by the SAW application framework.

In more detail, cisstISI 2002 is a wrapper class that encapsulates ISI API functions with cisstlibrary-compatible interfaces and emulating these functions for non-daVinci hardware, where appropriate. Wrappers are device interfaces that do not include a thread of execution and are "wrappers" around the device drivers or vendor APIs. CisstStereoVision 2004 is an algorithm for managing stereo image pairs and geometry, used in presenting stereo endoscope images to the surgeon console or headset. Open GL stands for Open Graphics Library and is a standard specification defining a cross-language cross-platform API for writing applications that produce 3D computer graphics. The visualization toolkit VTK 2008 is an open source, freely available software system for 3D computer graphics, image processing, and visualization. As previously discussed, brick manager 2010 is a 3D scene manager for the surgeon console similar to a 2D window manager. Block 2012 is the user interface (UI) interaction module. The UI interaction module 2012 is the core interaction logic that defines the operation of the user interface at the surgeon console. This component manages user input from the master interface and interprets this input with respect to scene objects managed by the brick manager. Movements of the MTMs in combination with grip open and close motions are correlated with scene objects such as icons and menus to produce a predefined result.

Examples of the capabilities of an interactive user interface system are illustrated in the following scenarios. These are simplified examples for illustrative purposes only. While certain exemplary embodiments are described, it is to be understood that such embodiments are merely illustrative of and not restrictive on the broad invention, and that the embodiments of the invention not be limited to the specific uses shown.

Image Guidance Using a Laparoscopic Ultrasound Instrument

In this exemplary scenario, a dynamic laparoscopic ultrasound (LapUs) image is overlaid on a tracked LapUS instrument in the stereo endoscope view provided by the surgeon console of the surgical system.

Figure 21:
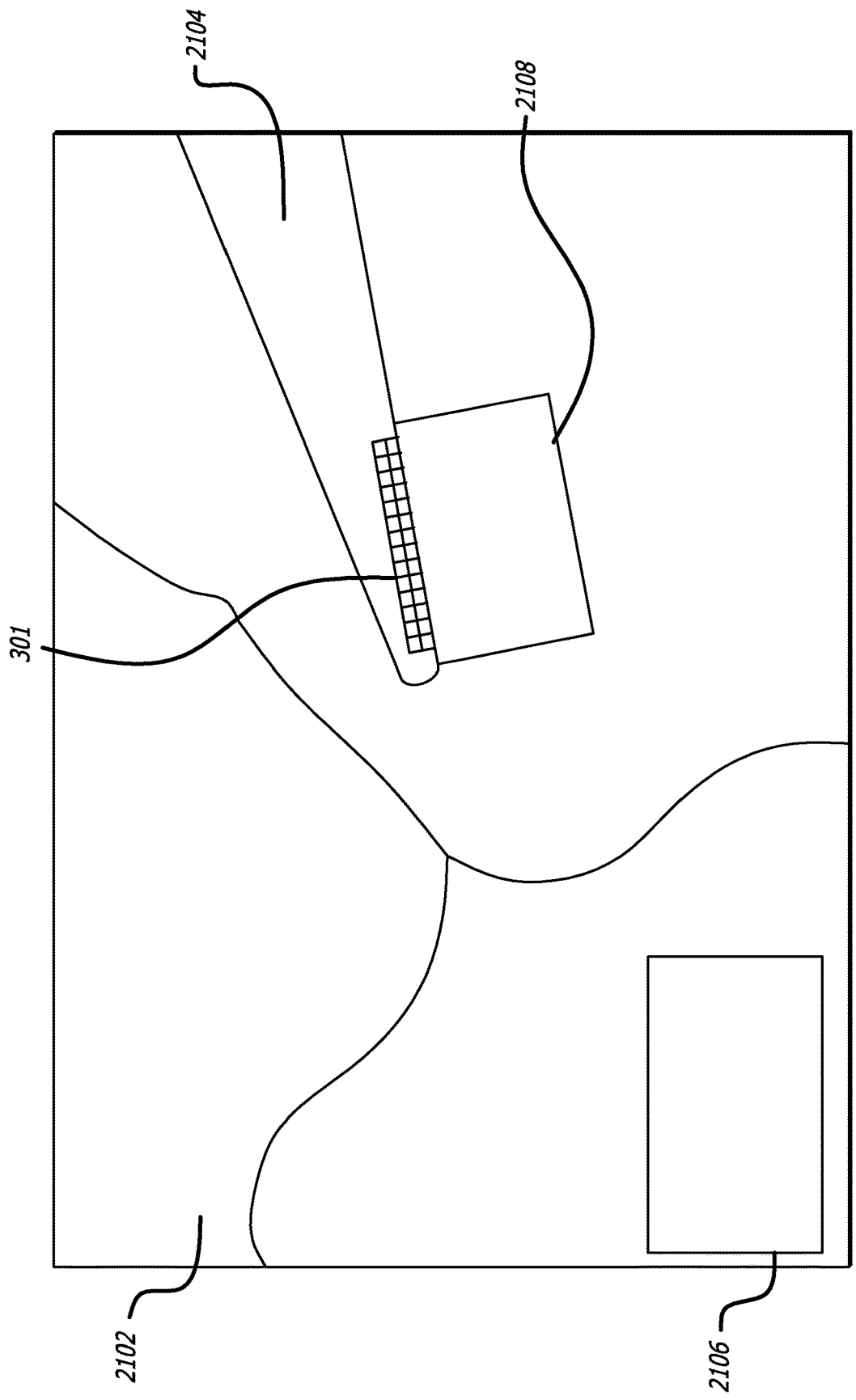
FIG. 21 is a diagrammatic view of a 3D interface display for a surgeon console in a minimally invasive surgical system.

FIG. 21 is a diagrammatic view of a stereoscopic interface display for a surgeon's console in a minimally invasive surgical system for a user to view images in three dimensions. The display shows tissue 2102 at a surgical site that is within the field of view of an endoscope (not shown). The display also shows an exemplary minimally invasive surgical instrument 2104 (e.g., a laparoscopic ultrasound instrument) that appears to extend into the visual field.

In one aspect, an ultrasound image of tissue is displayed within an inset window 2106 of the display (LapUS inset view). Alternatively, the inset window 2106 may be displayed outside the boundaries of the live video image.

In another aspect, a flashlight image window 2108 that shows an ultrasound image of tissue is electronically attached to the image of surgical instrument 2104 within the display (LapUS flashlight view). The images in the flashlight image window 2108 may be live image data (intra-operative images) from a LapUS probe or some other imaging source. As depicted in FIG. 21, the effect of the flashlight image window 2108 is that it appears attached to the instrument 2104 similar to how a flag is attached to a flagpole. However, the flashlight image window 2108 may be other shapes, and in some aspects is not necessarily attached to the image of surgical instrument 2104. U.S. Pat. No. 6,799,065 entitled IMAGE SHIFTING APPARATUS AND METHOD FOR A TELEROBOTIC SYSTEM, issued on Sep. 28, 2004 to Gunter D. Niemeyer, incorporated herein by reference describes an image shifting mechanism that may be used to facilitate the appearance of the flashlight image window 2108 being substantially connected to the LapUS probe.

The flashlight image window 2108 moves as the surgeon moves instrument 2104. The image displayed in the flashlight image window 2108 may become foreshortened as the surgeon moves instrument 2104, e.g., the surgeon points instrument 2104 more deeply into the surgical site. The flashlight image 2108 may change angle and orientation corresponding to the movement of the surgical instrument 2104 to indicate the orientation of the ultrasound sensor 301. That is, the ultrasound images slices captured by the ultrasound probe may be overlaid into the camera images so as to appear as to be emanating in proper perspective from the ultrasound sensor. Thus, the effect is of a flashlight that can be shined at various positions within the displayed image to provide enhanced visual information (e.g., the ultrasound image) to a surgeon.

Prior to engaging the SAW, a laparoscopic ultrasound instrument is attached to one of the active patient side manipulators (PSMs) and is inserted through a cannula into the body cavity. The ultrasound transducer is calibrated to the surgical instrument. Furthermore, endoscopic video outputs from the surgical system are connected to the SAW, video output from a diagnostic ultrasound device is connected to the SAW, video output of the SAW is connected to the master surgeon console, and the SAW may be connected to the surgical system through a network interconnection (e.g., Ethernet). A surgeon operates the master surgeon console which displays the live endoscopic images and allows the surgeon to operate the PSMs via the master tool manipulators (MTMs).

Figure 22A:
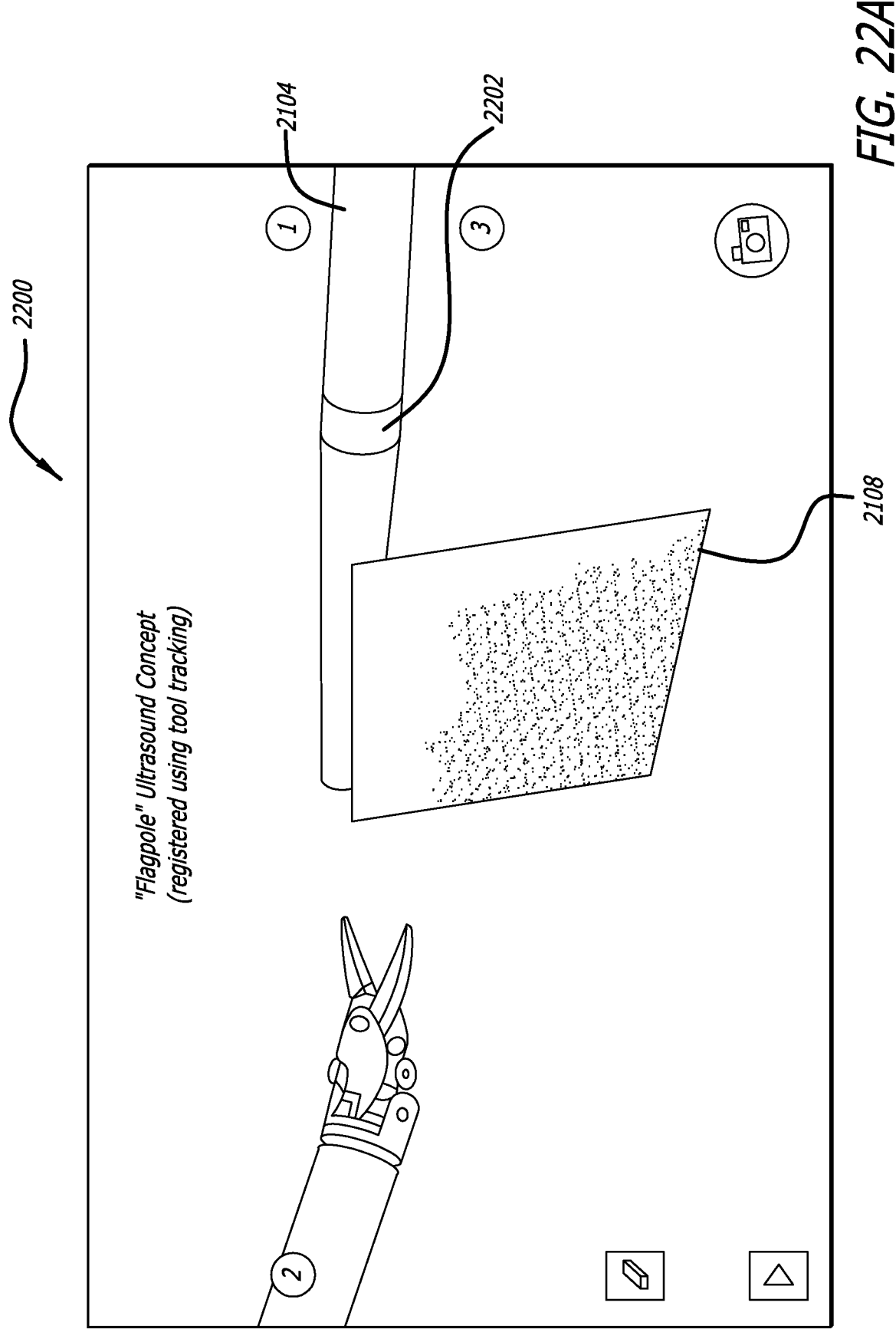
FIGS. 22A-22C are exemplary diagrammatic views of invoking the graphical user interface to overlay menu systems, icons, a pointer, and a flashlight view of images onto the captured camera images displayed in the 3D interface display of the surgeon console.
Figure 22B:
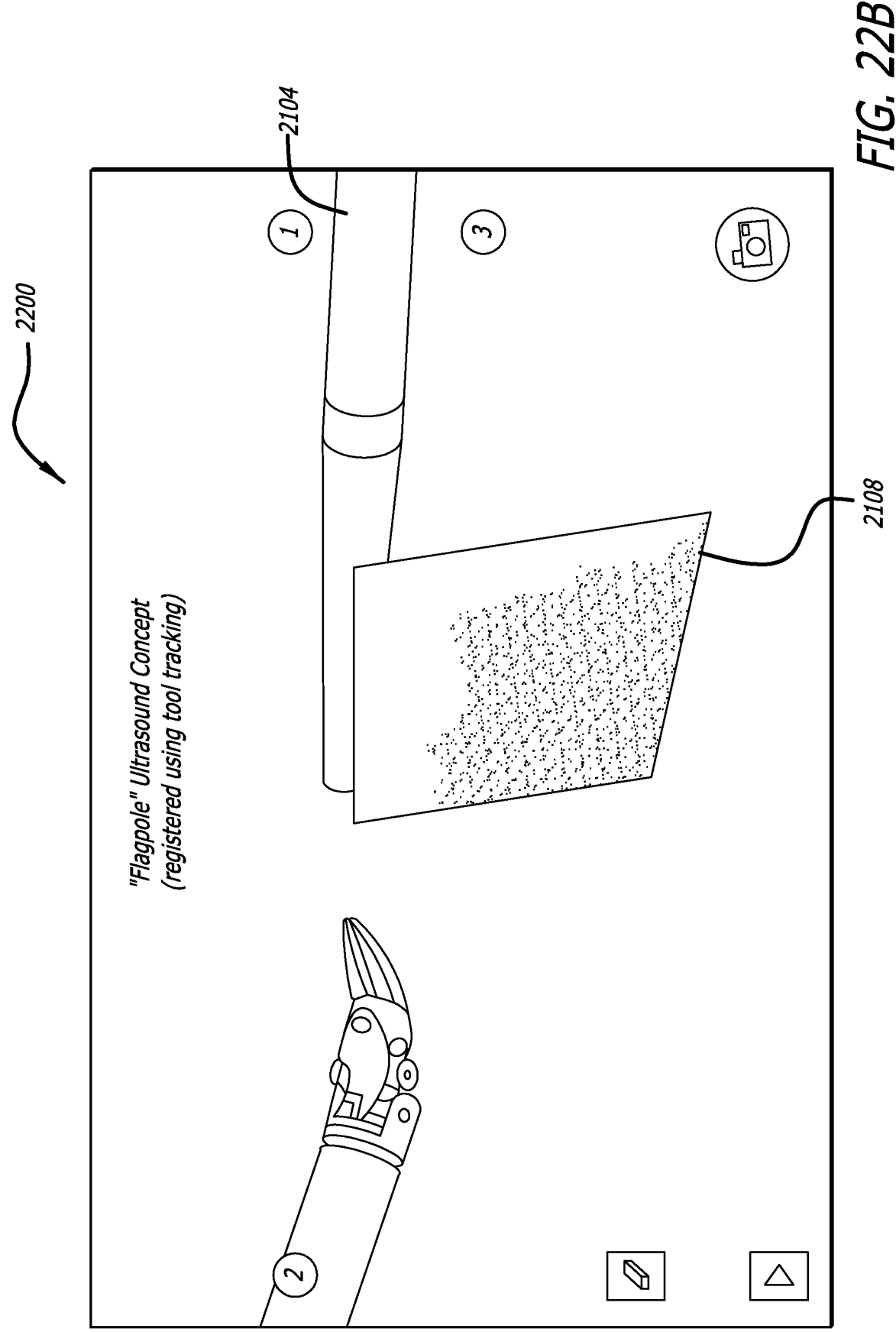
Figure 22C:
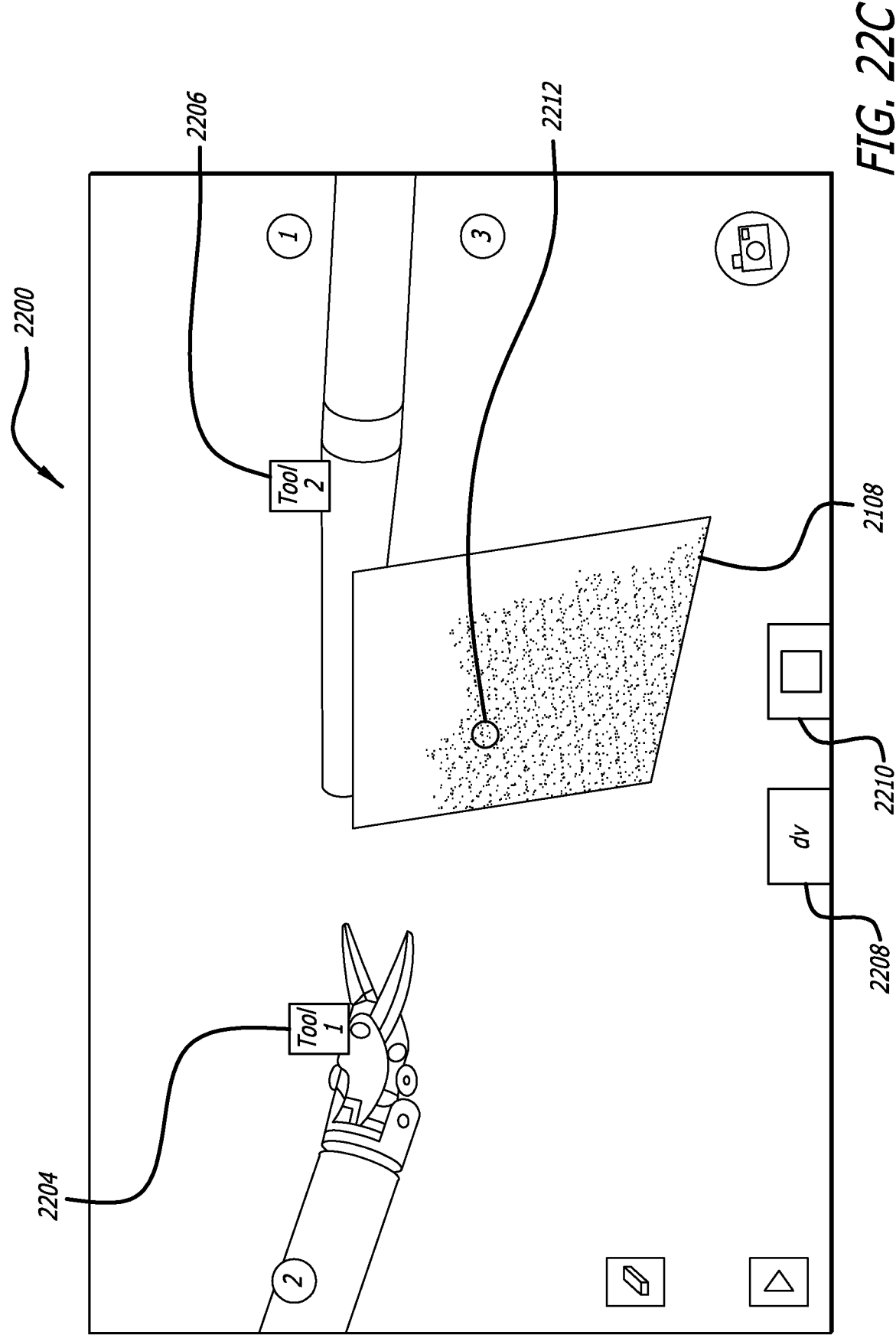

FIGS. 22A-22C are illustrations of a surgery performed while in the LapUS flashlight view mode. A flashlight image window 2108 is attached to the surgical instrument 2104 as shown in FIG. 21. In this example, the surgical instrument 2104 is a LapUS probe (see laproscopic ultrasound probe 150 illustrated in FIG. 3) with a wristed joint 2202 for increased degrees of freedom of movement.

In FIG. 22B, a first orientation of surgical instrument and flashlight image window 2108 are shown. In FIG. 22B, the orientation of the flashlight image window 2108 has slightly changed with a slight change in the orientation of the surgical instrument from that shown in FIG. 22A. Note that the flashlight image window 2108 is slightly away from the viewer compared to the flashlight image window 2108 illustrated in FIG. 22A. Also note that the video image displayed in flashlight view 22B has changed slightly as well due to foreshortening. LapUS probe 2104 captures slices of images under the ultrasound sensor 301 in the probe head. Thus, the captured image slices and the flashlight image window change as the probe head moves the ultrasound sensor 301 around the surgical site.

To engage the graphical user interface mode, a surgeon depresses the master clutch pedal on the surgeon console and closes both master input devices (e.g., MTMs) in order to enter a masters-as-mice mode. The master input devices may be held closed for a predetermined period of time in order to enter the masters-as-mice mode in another embodiment.

In FIG. 22C, the graphic user interface (GUI) mode is active. In the GUI mode, a 3D pointer/cursor 2212 and a first menu system (including menu buttons 2208 and 2210) may be overlaid onto the camera images of the surgical site displayed at the surgeon console. Graphical tool icons 2204 and 2206 may also be overlaid near each PSM instrument.

In FIG. 22C, various icons in the graphical user interface may be overlaid onto the images of the surgical site in the display 2200. An icon may provide information, open a menu system to provide additional control or functionality, and be context specific depending on what surgical instrument 2104 is being used. For example, graphical tool icons 2204 and 2206 indicate a masters-as-mice mode and a graphical user interface (GUI) mode has been entered for the master input devices. Furthermore, the graphical tool icons 2204 and 2206 adjacent their respective instrument may be selected to provide additional information or further control and/or functionality depending upon the type of surgical instrument.

In FIG. 22C, the first menu system including menu buttons 2208 and 2210 may be used to further interact with the graphical user interface. For example, menu button 2208 may be used to open and close the LapUS flashlight image window 2108 while menu button 2210 may be used to open and close a medical image view mode.

FIG. 22C also illustrates the 3D pointer 2212 overlaid upon images within the display. In this example, the surgeon has moved the pointer 2212 over the flagpole image window 2108 in the display with the master input devices in the masters-as-mice mode. To show the pointer in three dimensions selecting various surfaces, the size of the pointer may vary as its depth varies in response to the master input devices in the masters-as-mice mode. This may be seen in the comparison of pointer 2212 in FIG. 22C and pointer 2304 in FIG. 23.

Figure 23:
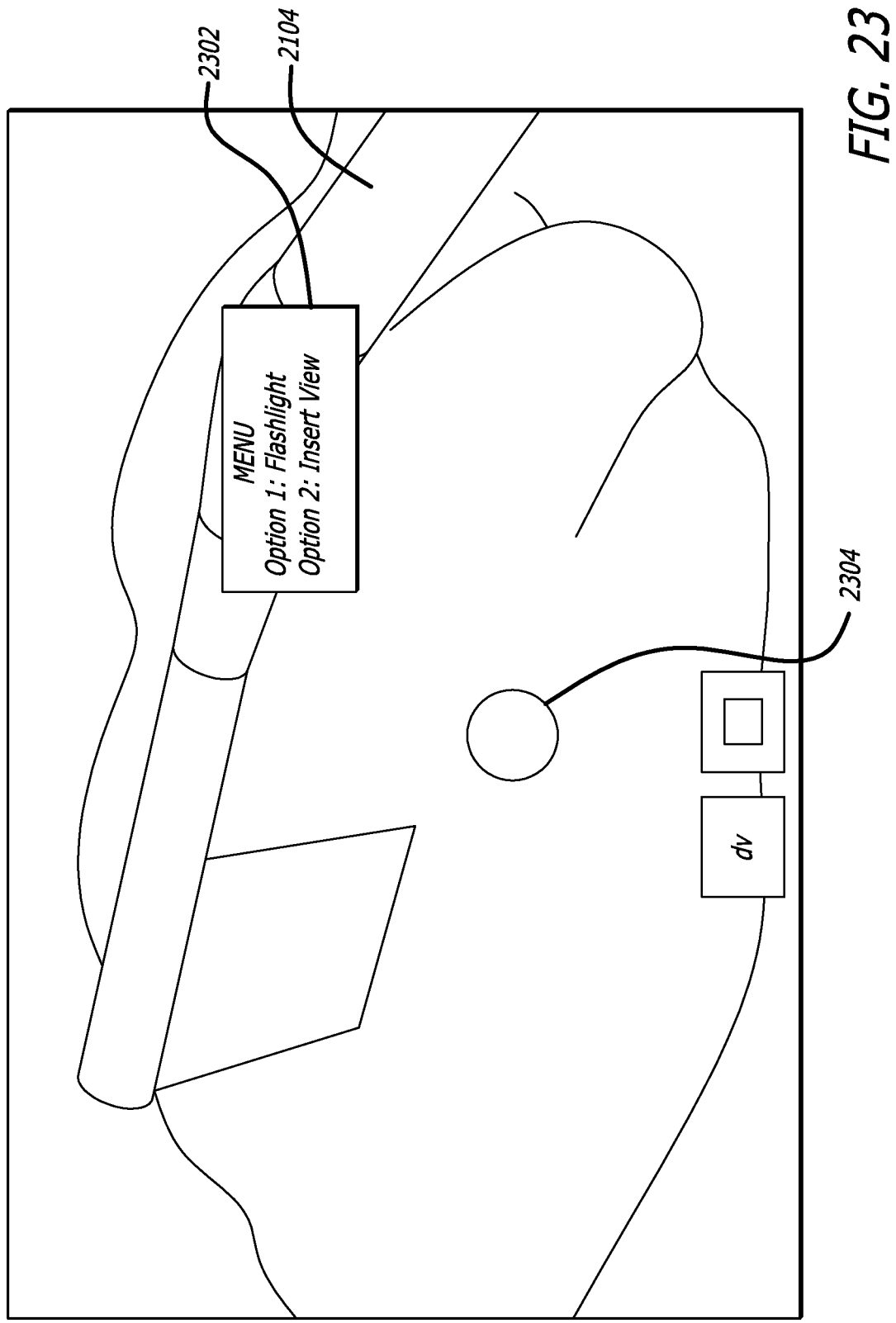
FIG. 23 is an exemplary diagrammatic view of a pointer being used to select menu items to select context sensitive menu items from a menu overlaid onto the captured camera images adjacent a surgical instrument.

FIG. 23 depicts a menu system 2302 which may be displayed in response to selection of an icon or menu button by the 3D pointer/cursor 2304 and the master input devices. The menu system 2302 that is overlaid onto the images may be context sensitive, such as being responsive to the type of surgical instrument 2104.

The following is description of an exemplary method of interacting with the GUI in the masters-as-mice mode. Other methods may be used to manipulate the 3D pointer using the master input devices (MTMs) and should be considered as part of the inventive concept disclosed in this application.

In one embodiment, the surgeon may move the 3D pointer by manipulating the primary MTM. Using the MTM, the surgeon moves the 3D pointer 2304 over the tool icon (e.g., icons 2201-2202 in FIG. 22C) attached to the ultrasound instrument and closes the grip on the MTM to signal click or select. A pull-down menu 2302 opens and may display options, such as option 1, a LapUS flashlight view, and option 2, a LapUS inset view.

The surgeon moves the primary MTM to highlight the first option, the LapUS flashlight view. The surgeon releases the grip on the primary MTM and the ultrasound flashlight image (a plane) is overlaid onto the camera images in a flashlight image window 2108 adjacent the ultrasound instrument 2104. When the surgeon releases the master, the menu system and tool icons disappear, while the ultrasound overlay remains. The overlaid ultrasound flashlight image window 2108 moves with the LapUS instrument, fixed to the coordinate frame of the ultrasound transducer/sensor 301.

Alternatively, the surgeon may select the second option, the LapUS inset view. In the LapUS inset view, the ultrasound image is overlaid onto the endoscopic image within an inset window 2106 in the stereoscopic display at the surgical console. The LapUS inset window 2106 may be resized by using the MTMs. The LapUS inset window 2106 may also be moved to different positions within the display on the master console.

By overlaying a GUI over live images from the endoscope and further overlaying ultrasound images captured by the ultrasound instrument onto the live images, the SAW fuses graphical objects with physical objects in a physical coordinate frame.

FIG. 12 shows an illustrative data flow diagram focusing on the robot API and the pipeline for video processing and visualization. This figure also shows the tool tracking and volume viewer subsystems. Although not specifically shown, calibration and registration functions may be performed.

Image Guidance Using a Medical Image Overlay

In this example, a medical image volume is opened at the surgical console of the surgical system. A medical image volume may be a pre-operative image including magnetic resonance images, computer tomography images, ultrasound images, positron emission tomography images, or other known medical image volumes that may be stored in known formats. The medical image volume is overlaid onto live endoscopic imagery displayed on the surgical console.

FIGS. 24A-24D illustrate a step-by-step procedure to open the medical image database. The master controller(s) (also referred to as master tool manipulators or input devices) that control the slave instrument(s) may be used to control a pointer 2212 in the display. The pointer may appear to operate in three dimensions rather than in two dimensions as generally appears on most graphical user interfaces. Since the display has a three dimensional appearance, the user interface can be thought of as having volume (like a brick) instead of being flat (like a two-dimensional window).

In one aspect the surgeon may move an overlaid ultrasound image or other pre- or intra-operative image by using one or more master controllers. The overlaid image is on, e.g., a live video image from an endoscope at the surgical site. The surgeon may move the overlaid image to align with the live video image of a particular tissue structure. In one aspect, one master controls the overlaid image position, and another master controls the overlaid image orientation. Such image movement control may be somewhat analogous to that of the endoscopic camera control mode in a robotic surgical system. In these aspects, the overlaid image is not automatically registered with a tissue structure seen in the live video.

Prior to engaging the SAW system, endoscopic video outputs from the robotic surgical system are connected to the SAW, video output of the SAW is connected to the master surgeon console, and the SAW may also be connected to the robotic surgical system via Ethernet.

The surgeon operates the master console showing stereo display of live endoscopic images.

Figure 24A:
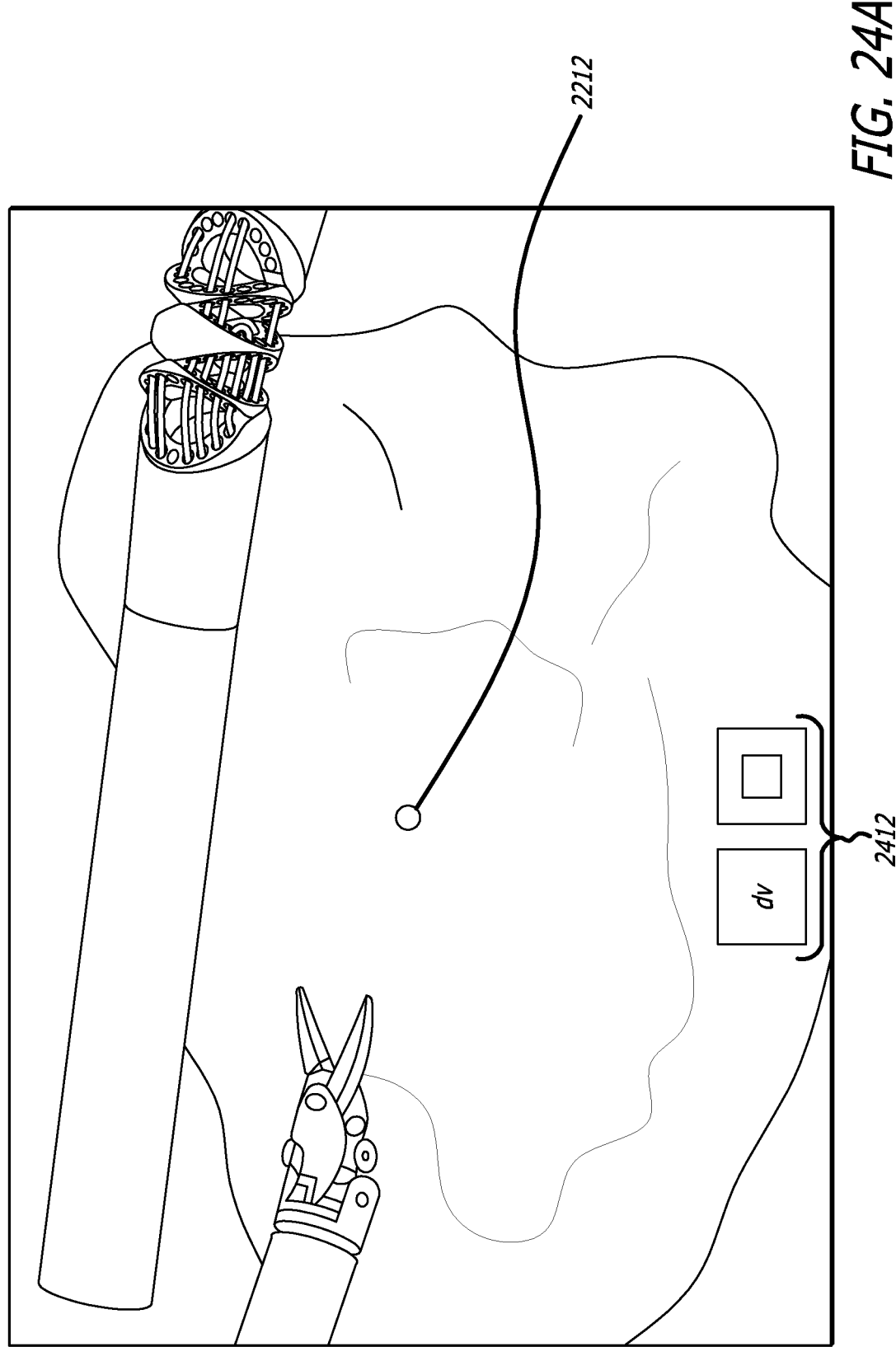
FIGS. 24A-24D are exemplary diagrammatic views of invoking the graphical user interface to overlay menu systems, icons, a pointer, and a medical image volume onto the captured camera images displayed in the 3D interface display of the surgeon console.

In FIG. 24A, the surgeon depresses the master clutch and enters the masters-as-mice mode activating the GUI mode wherein a 3D pointer/cursor 2212 and a menu system 2412 are overlaid onto camera images displayed in the display device of the surgical console. Graphical tool icons (e.g., icons 2204 and 2206 in FIG. 22C) may also overlaid near each of the PSM tools (not shown in FIG. 24A).

Figure 24B:
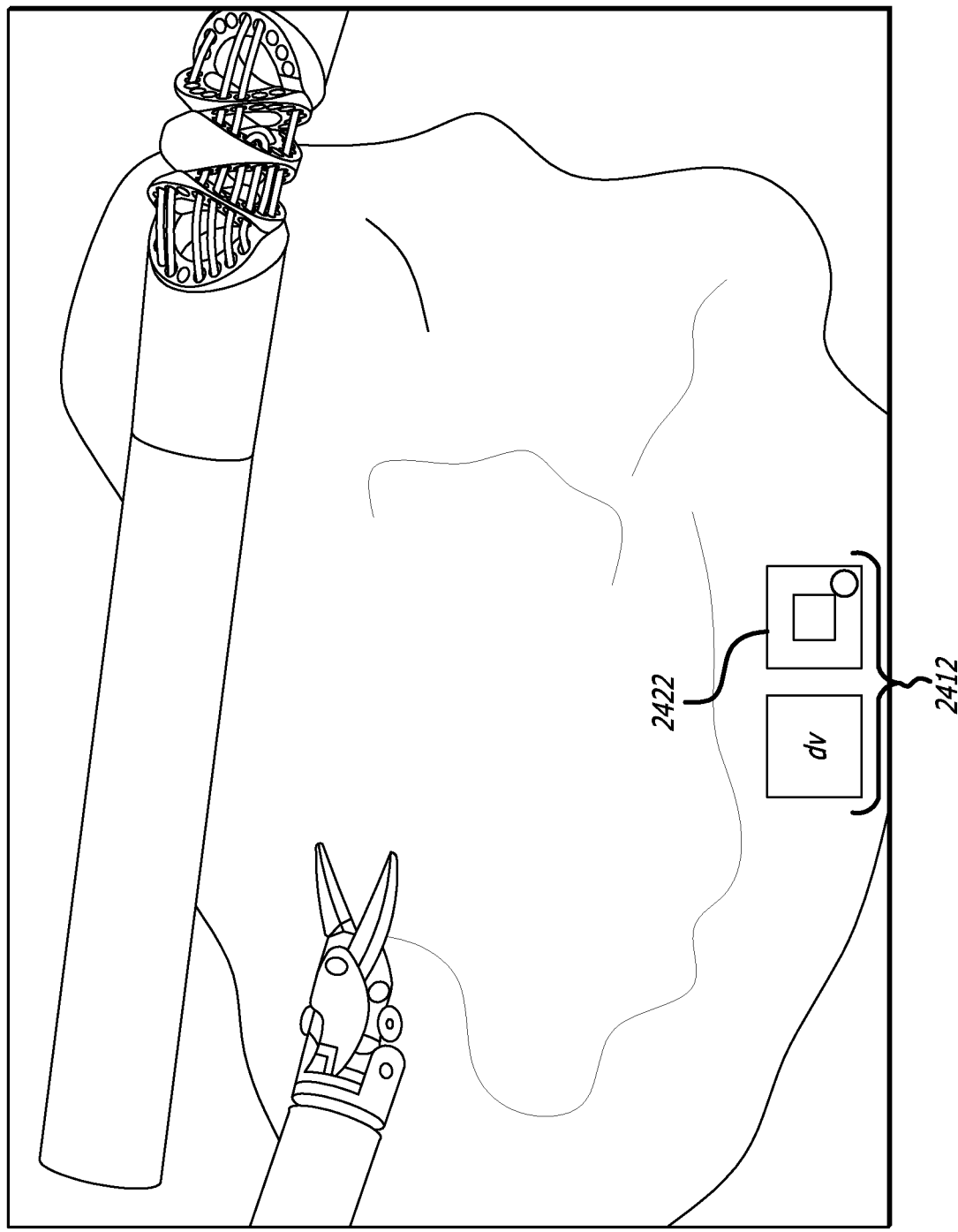

The surgeon moves the 3D pointer 2212 to a pull-down menu button 2422 visible on the overlaid menu system 2412 in FIG. 24B by manipulating the primary MTM. The button may be marked with text such as "View Image Volume" or an icon of an image volume. The surgeon may select the menu button in the GUI by closing the grip on the primary MTM. The pull-down menu may then open to display a list of predetermined image data sets listed by their unique identifiers. The pull-down menus may be context sensitive, such as the pull down menu 2302 overlaid onto the live camera images from the endoscopic camera as shown in FIG. 23.

Figure 24C:
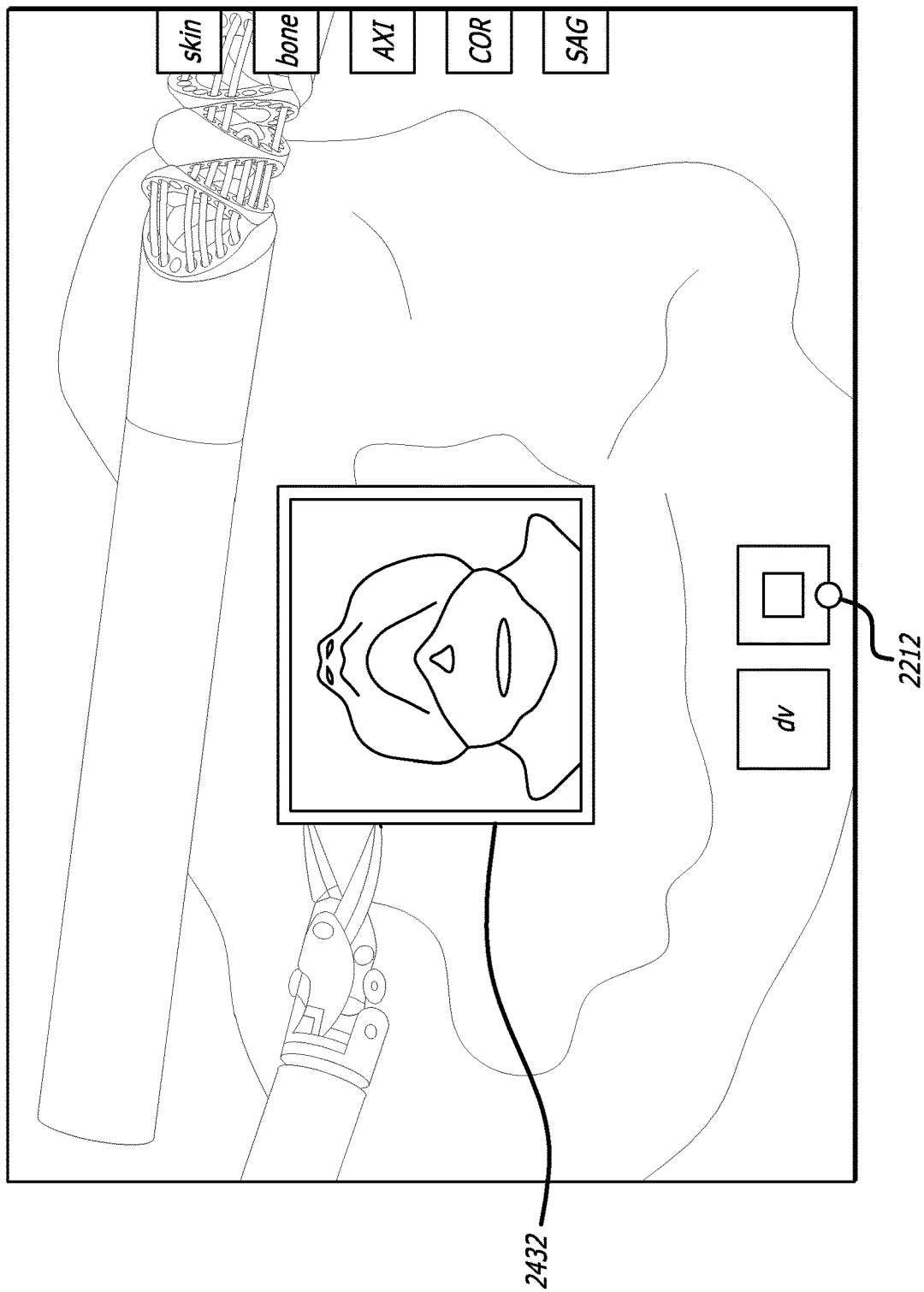
Figure 24D:
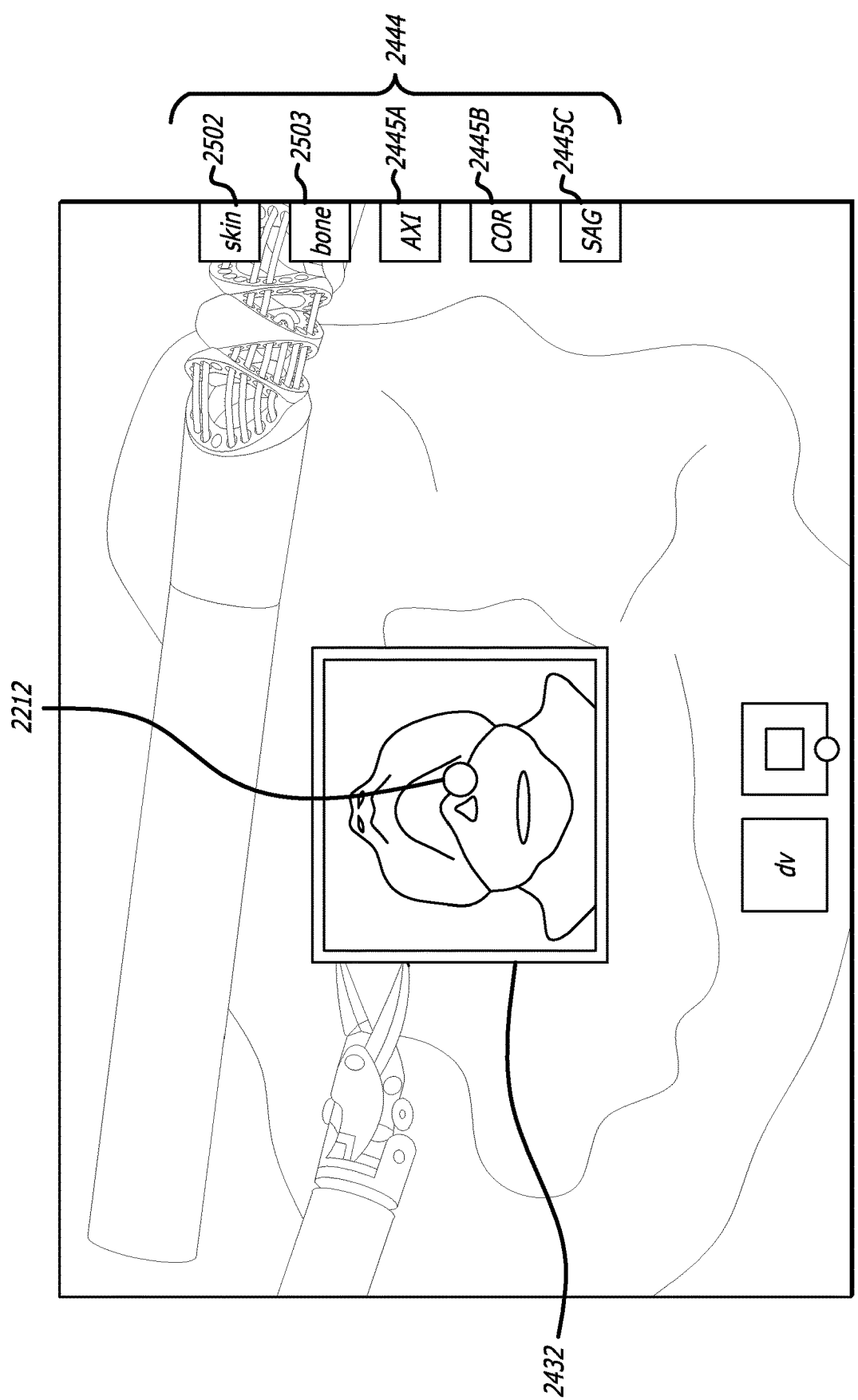

The surgeon highlights the desired image volume and releases the grip on the primary MTM causing an annotated image volume bounding box 2432 to be overlaid onto the camera images in the display of the surgeon console as may be seen in FIGS. 24C and 24D. Depending upon the image volume selected, a three dimensional image may be displayed in the bounding box 2432. Using other menu options 2445A-2445C in another menu system 2444, the surgeon may desire to display a single image slice within the bounding box.

Crosshairs (not shown) may optionally be used to indicate the location of the origin and eight corners of the image volume in the display. Crosshairs (not shown) may also be optionally used to indicate the location of the four corners of an active slice plane in the display.

The surgeon may manipulate the selected image volume by operating the MTMs singularly or conjunctively together in the masters-as-mice and GUI modes. For instance, the primary and/or secondary MTMs may be used to pan, zoom and rotate the image volume. U.S. Pat. No. 6,799,065 entitled IMAGE SHIFTING APPARATUS AND METHOD FOR A TELEROBOTIC SYSTEM, issued on Sep. 28, 2004 to Gunter D. Niemeyer, incorporated herein by reference, describes an image shifting mechanism that may be used to facilitate the manipulation of image volumes in response to the movement of the primary and/or secondary MTMs in the masters-as-mice mode.

Figure 25A:
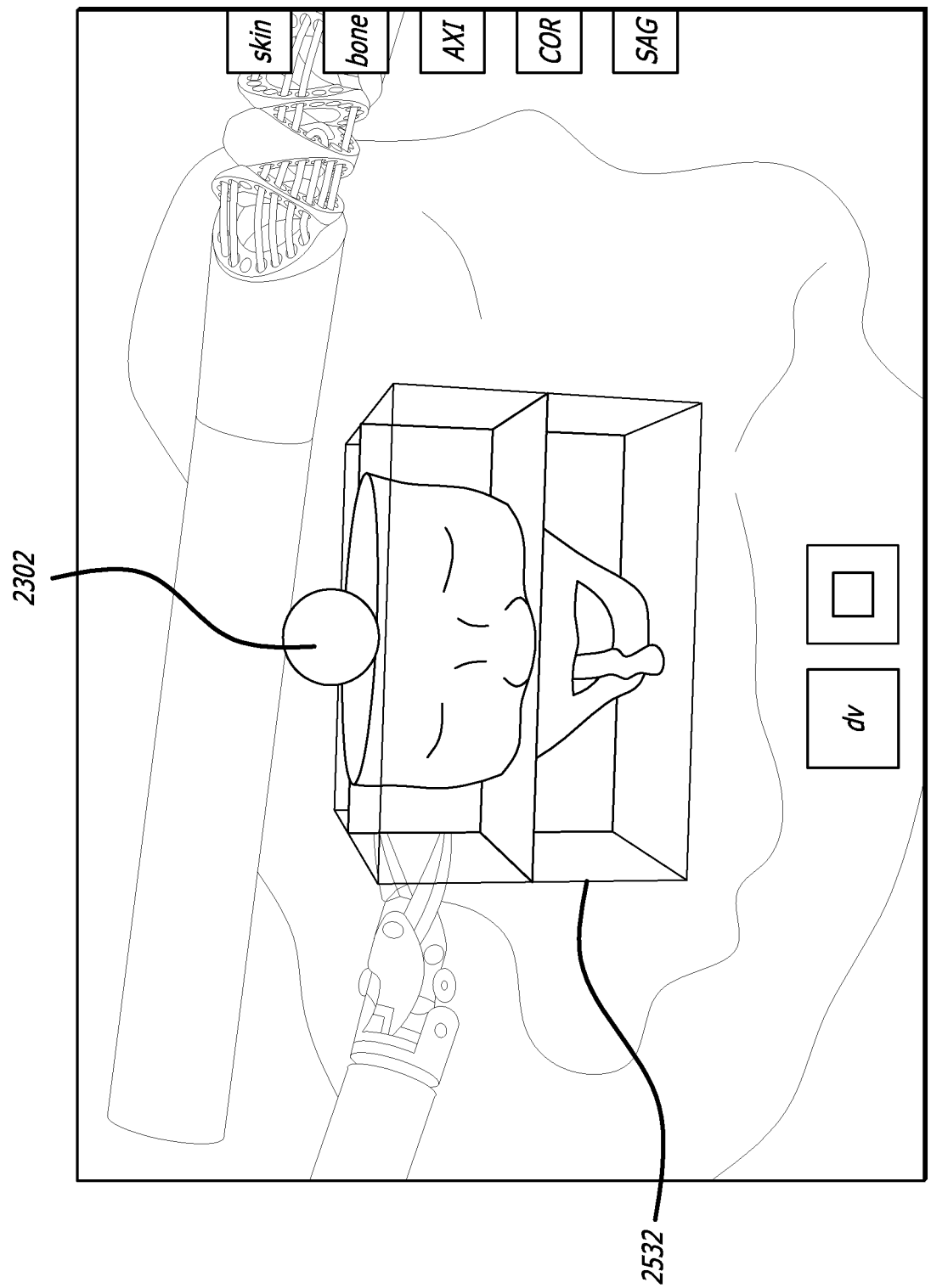
FIGS. 25A-25E are exemplary diagrammatic views of manipulating a medical image volume and selecting menu items overlaid on the captured camera images displayed in the 3D interface display of the surgeon console.
Figure 25B:
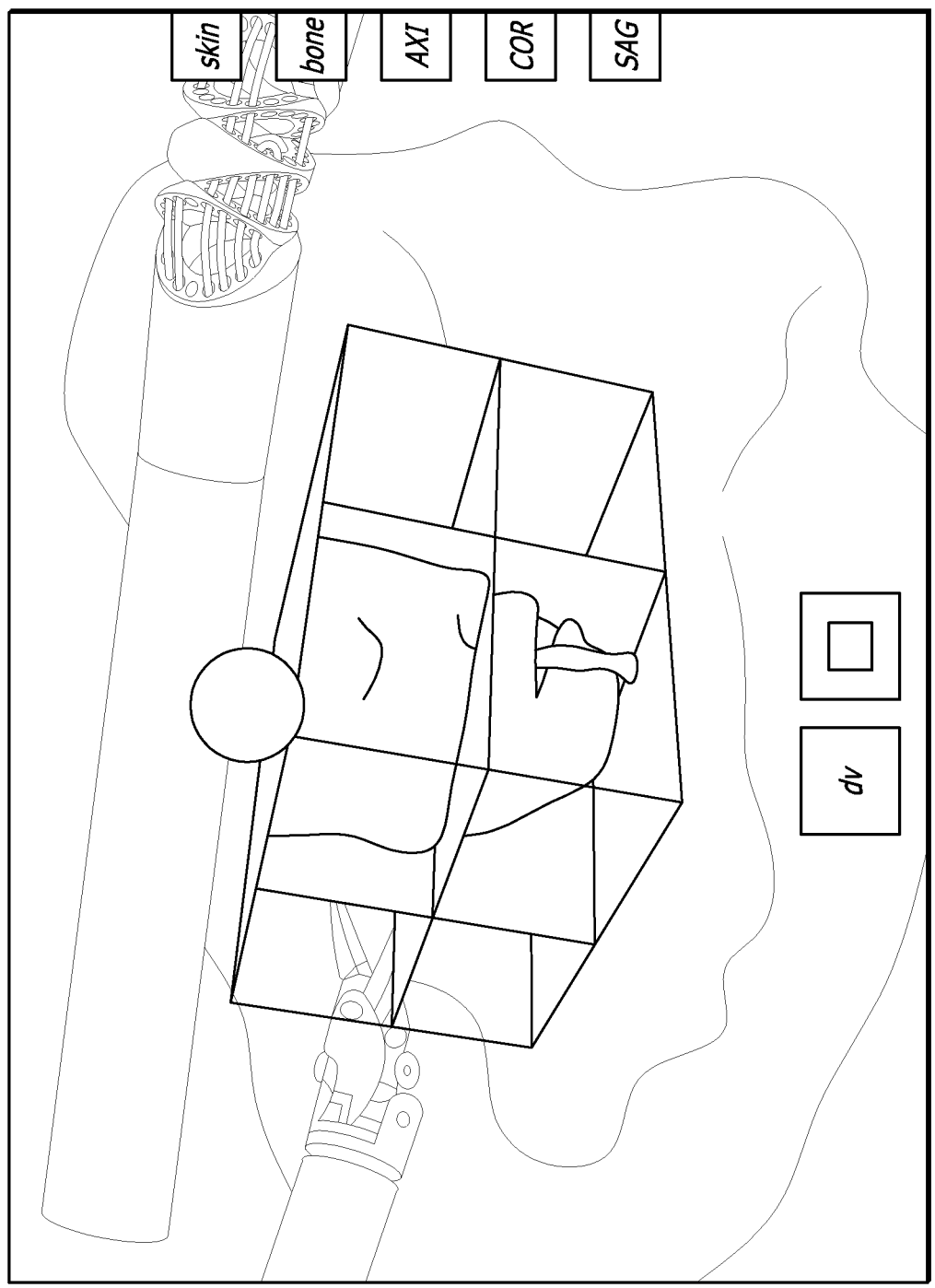
Figure 25C:
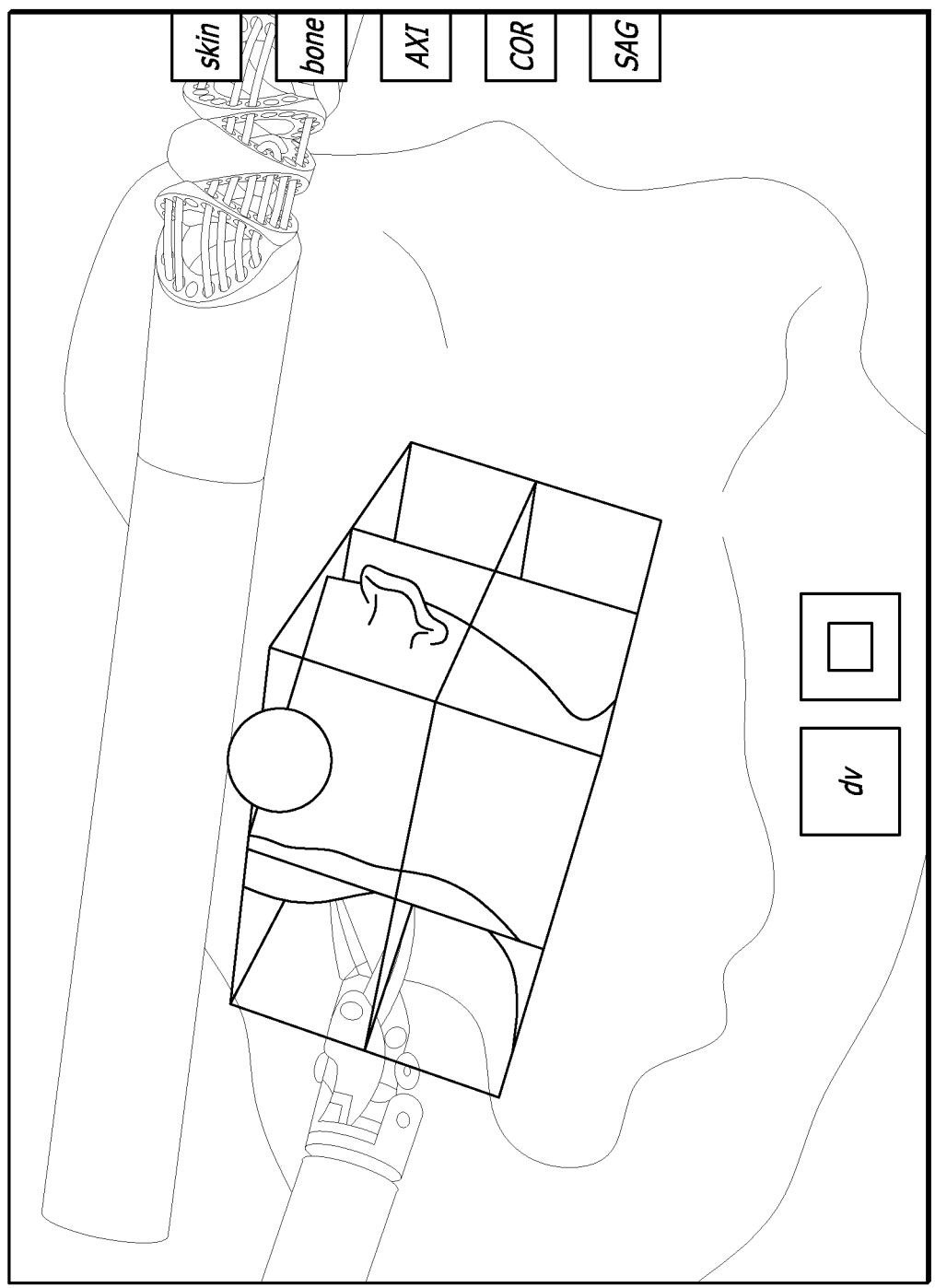

In one embodiment, the surgeon may move the 3D pointer 2302 over the image volume 2532 as shown in FIG. 25A and close the grip of the primary MTM to select the image volume. To pan the image volume, the primary MTM may be moved to translate the image volume from one position of origin to another.

The image volume may be rotated along any axis thereby changing the perspective. Relative motion between the primary and secondary MTM can control the image volume orientation. A surgeon may rotate the image volume until the perspective view of the image volume matches the perspective of the live endoscopic camera.

FIGS. 25A-25D illustrate the rotation of an image volume in a counterclockwise direction by manipulating the primary master input device (MTM) and the secondary master input device (MTM) together to form a relative motion there between.

Figure 25D:
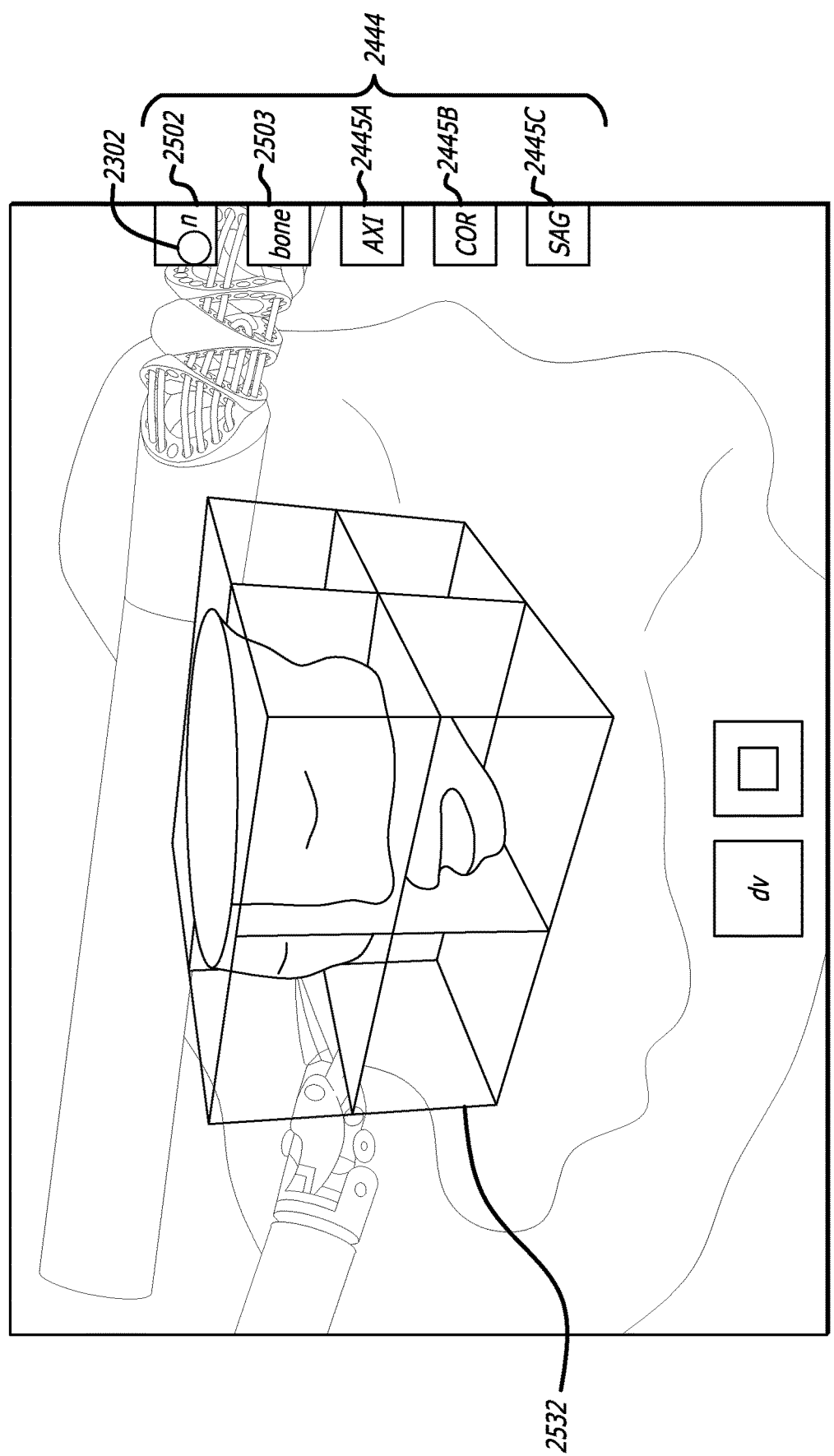
Figure 25E:
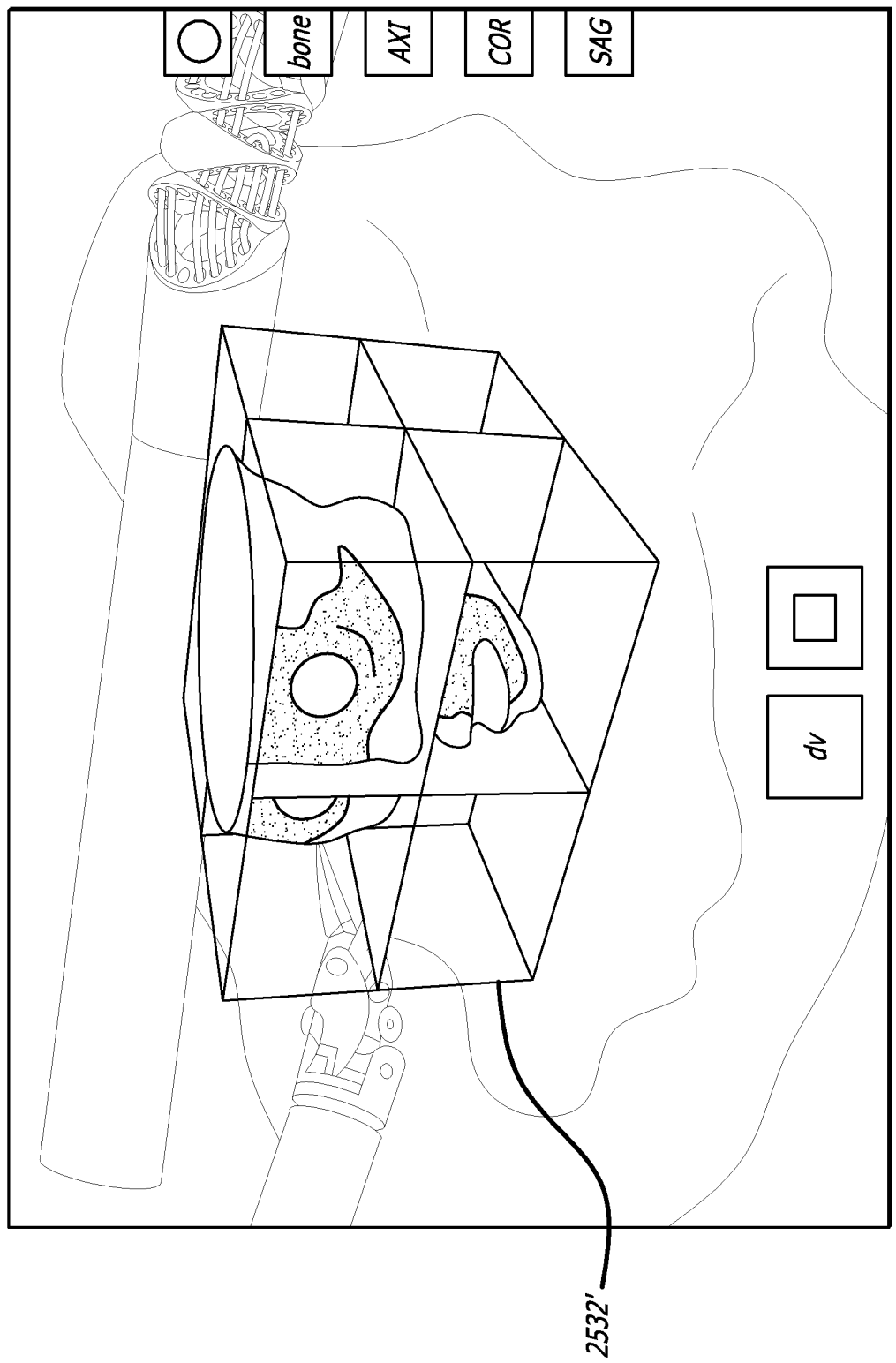

Menu options 2502, 2503, 2445A-2445C of a menu system 2444 overlaid onto the camera images displayed on the display as shown in FIG. 25D may allow the surgeon to further manipulate the image volume 2532. For instance, in FIG. 25D, the surgeon may opt to remove a surface layer or skin from the displayed image volume 2532 by clicking on a skin menu button 2502 with the cursor/pointer 2302 in a menu system 2444 associated with the image volume. The modified image volume 2532' is shown in FIG. 25E.

By selecting different menu options, such as sagittal view or axial view, an image slice 2632 of the image volume 2532 defined by a slice plane 2645 may be displayed within the bounding box 2532 of the image volume. Orientation of the slice plane 2645 may be controlled by movement of the MTMs in the MaM and GUI modes to view different image slices of the image volume.

In one embodiment, the surgeon moves the 3D pointer over one of the corners of the slice plane and closes the grip of the primary MTM to select the slice plane. The secondary MTM may be used to select another par of the slice plane by being positioned over a second corner. The relative motion between the primary and secondary input devices (MTMs) may be used to control the orientation of the slice plane. The primary and second MTMs may also be used to reformat the slice plane. The slice plane follows the motion of the primary MTM. Different slice planes may also be displayed as desired by the surgeon.

Figure 26A:
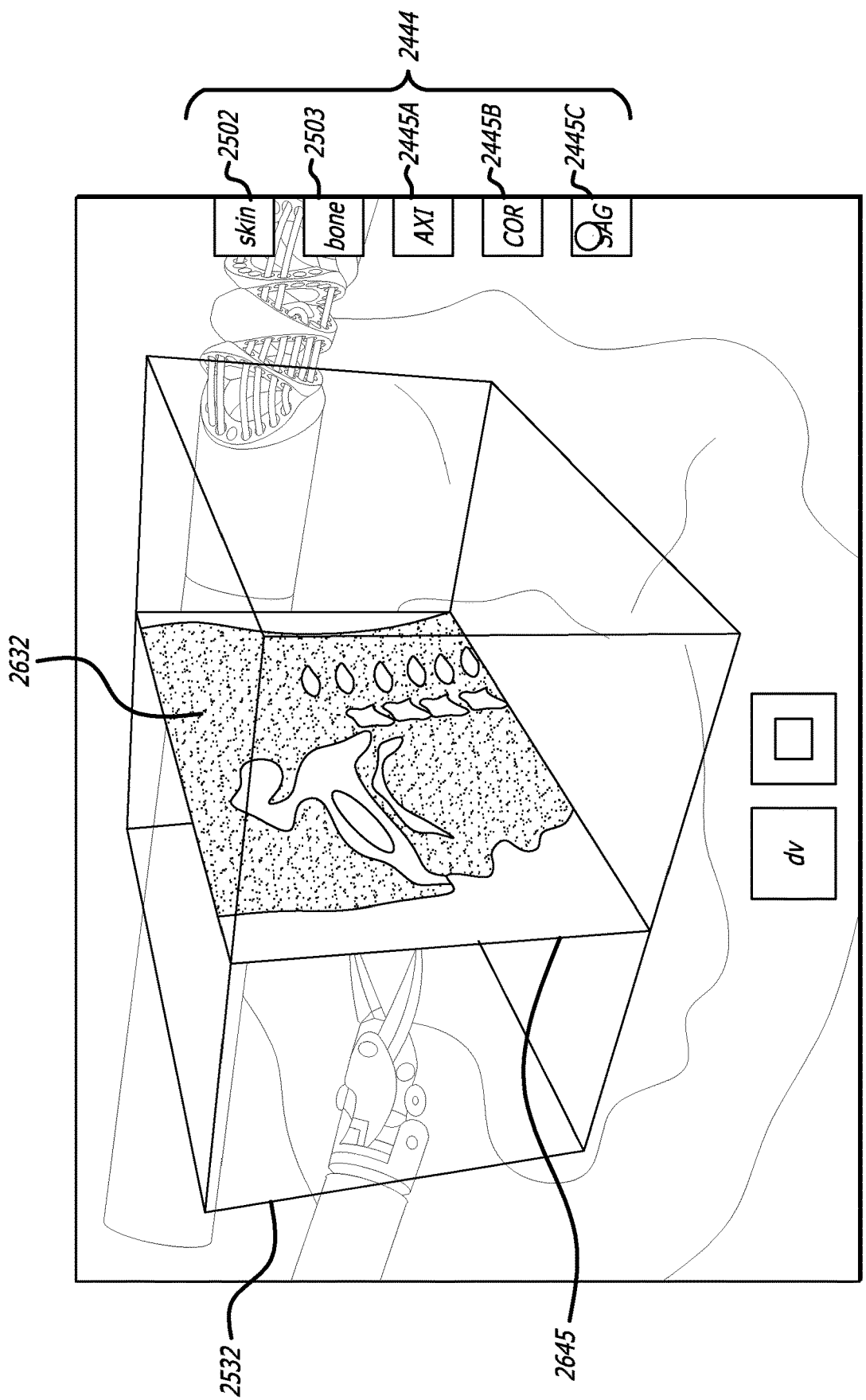
FIGS. 26A-26B are exemplary diagrammatic views of selecting menu items to display sagittal image slices of the medical image volume overlaid on the captured camera images displayed in the 3D interface display of the surgeon console.
Figure 26B:
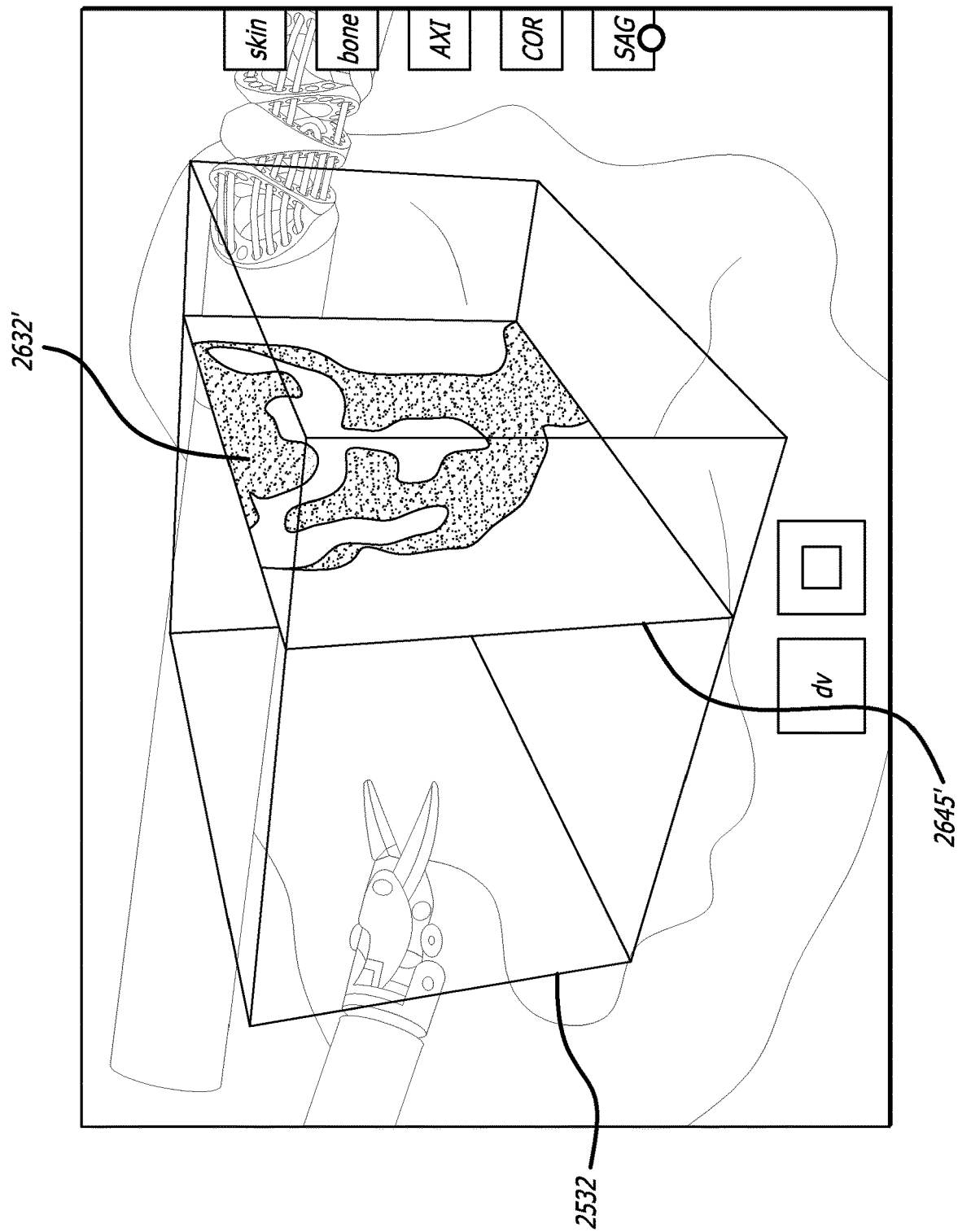

FIGS. 26A and 26B illustrate sagittal slice planes 2645, 2645' with different positions to form different image slices 2632,2632' of the same image volume 2532. Note that the slice plane 2632' illustrated in FIG. 26B is a slice plane taken further from the center of the skull, or more laterally than the slice plane 2632 illustrated in FIG. 26A.

Figure 27A:
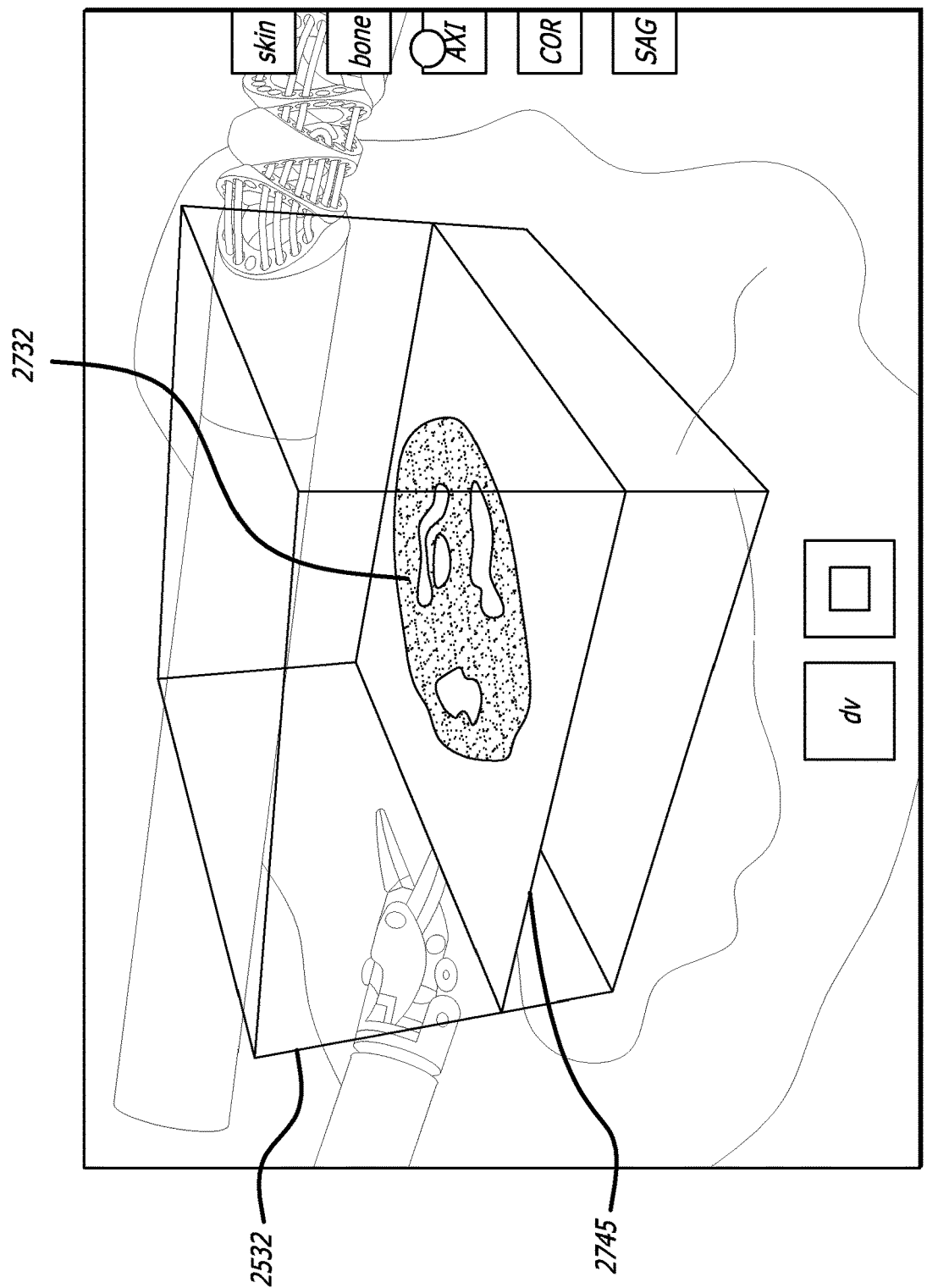
FIGS. 27A-27B are exemplary diagrammatic views of selecting a axial slice plane and manipulating the axial slice plane to display different image slices of the medical image volume overlaid on the captured camera images displayed in the 3D interface display of the surgeon console.
Figure 27B:
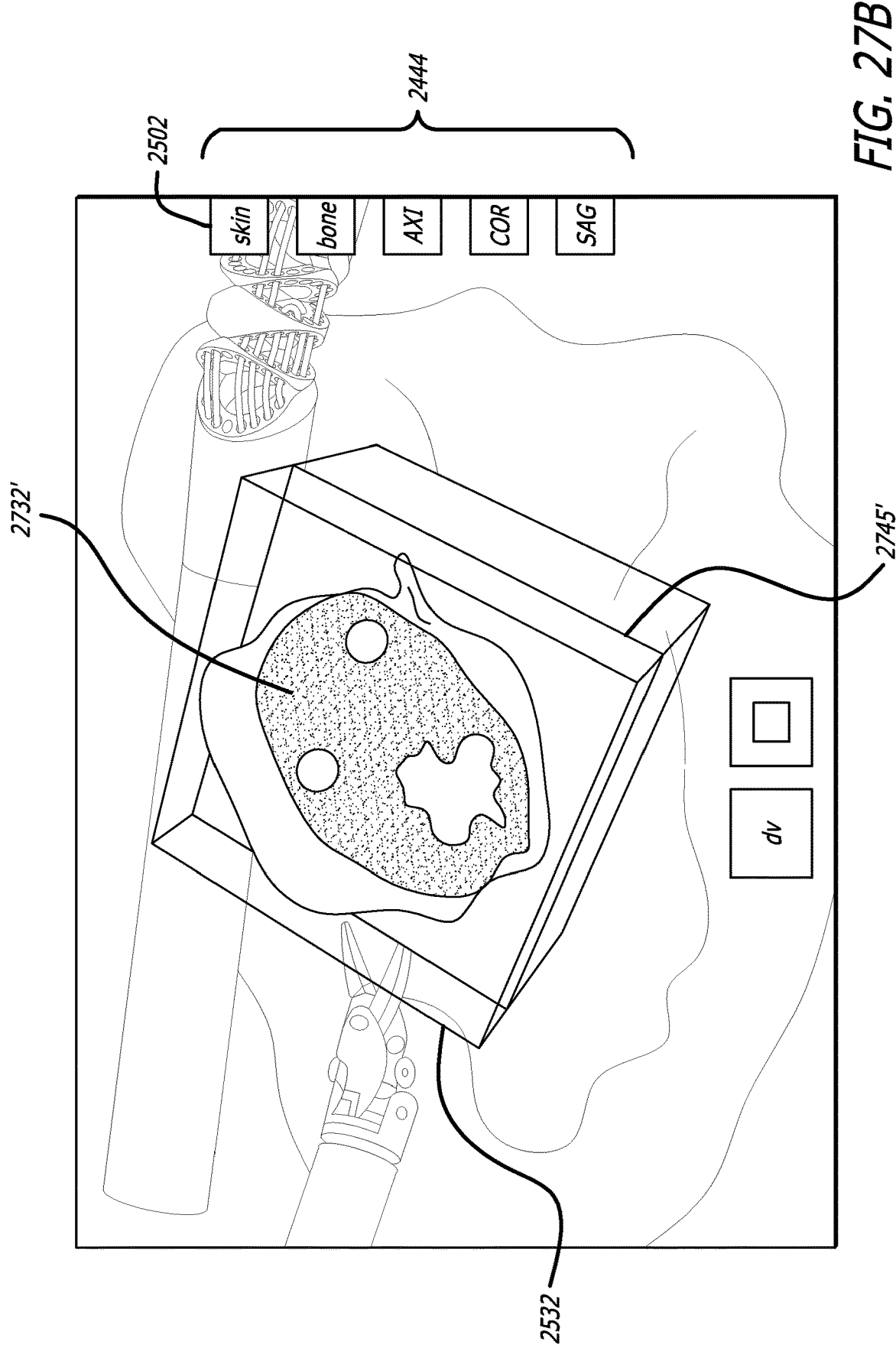

In FIGS. 27A and 27B, axial slice planes 2745,2745' are displayed slicing through the same three dimensional image volume 2532 with different positions to form different image slices 2732,2732'. Similar to sagittal view, the axial slices may be rotated or orientated by manipulating the MTMs. Also, different slices closer or further away from the crown of the skull may be displayed as the surgeon desires. In FIG. 27B, the surgeon has replaced the skin by selecting the appropriate menu button 2502 of the menu system 2444 while still in axial view.

To zoom in or out of the image volume, the primary and secondary MTMs may both be used. With the pointer over the image volume, the primary MTM is selected by closing its grip to select the image volume. The secondary MTM is also selected by closing its grip. A relative distance between the primary and secondary MTMs may then be used to control the level of zoom of a selected image volume or image slice. Thus, by selecting the image volume and then moving the MTMs to change their relative distance of separation, the surgeon may zoom in on or out from the image volume to display a desired level of detail.

Figure 28:
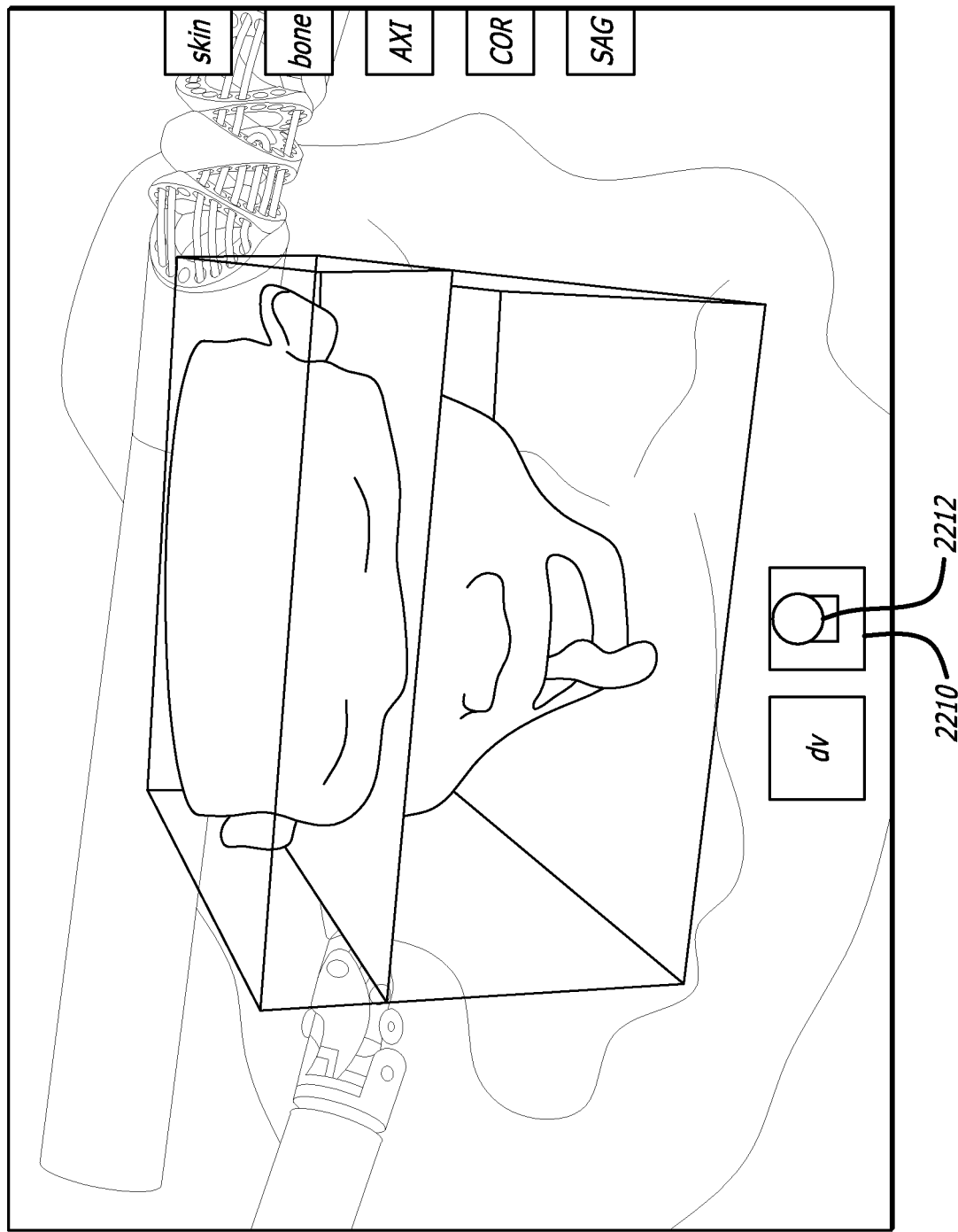
FIG. 28 is an exemplary diagrammatic view of menu selection to close a medical image volume.

To exit the image volume mode, a surgeon may re-select an image volume icon or menu button (e.g., menu button 2210). As depicted in FIG. 28, the surgeon selects the menu button 2210 once again with the pointer 2212 over it. This removes the overlay of the image volume 2532 and returns the initial display of the GUI in the MaM mode, such as shown in FIG. 24B.

To further exit the MaM, the surgeon may press the clutch pedal and click both master input devices (MTMs) so that the master input devices may return to control and couple motion into the minimally invasive surgical tools of the surgical system.

Note that the forgoing are simplified cases for illustrative purposes only and should not be considered as limiting the broad inventive concepts.

Mentoring

Another embodiment allows surgeons versed in the operation of a robotic surgical system to mentor another surgeon as a trainee. Two surgeon consoles are coupled with a single patient-side cart for mentoring purposes. One surgeon console is designated the supervisor console, while the second is the trainee console. A simplified case of mentoring is now described.

Before mentoring operations are conducted, two surgeon consoles are interfaced with the SAW. One patient side cart (PSC) is interfaced with the SAW and stereo endoscopic video output is connected to the SAW. Two sets of stereo video outputs of the SAW are connected, one to each of the da Vinci master consoles.

The supervisory surgeon depresses the master clutch pedal on the surgical console and holds the MTMs steady for three seconds, entering masters-as-mice mode. GUI mode becomes active and visible on both surgical consoles, a 3D pointer/cursor and menu system are overlaid onto the surgical consoles. Graphical tool icons appear at each of the PSM tools.

The supervisory surgeon moves the 3D pointer and selects "mentor mode" by closing the primary MTM grip while the pointer is appropriately positioned on the graphical menu system. The menu system disappears from the trainee console and PSM control is transferred to the trainee. A telestration menu appears on the supervisory console.

The camera clutch on the supervisory surgeon has shared control of the ECM. If both camera clutches are activated, then the trainee console takes precedence in order to direct the camera view. Menu options on the supervisory console allow the supervising surgeon to regain control of the PSMs, request control of the fourth arm to control telestration and to overlay pre-operative image volumes.

Further exemplary details of telestration may be found in U.S. patent application Ser. No. 11/322,866 entitled STEREO TELESTRATION FOR ROBOTIC SURGERY filed on Dec. 30, 2005 by Ben Lamprecht et al., which is incorporated herein by reference.

Virtual Fixtures and the Interactive Graphical User Interface

Another embodiment includes manipulation of virtual fixtures through an Interactive Graphical User Interface. With virtual fixtures, an interaction mode is formed in which the surgeon shares control of the robot with the computer process. These task-dependent computer processes may provide assistance to the surgeon by limiting the robot's motion within restricted regions and/or by influencing it to move along desired paths. U.S. Pat. No. 6,493,608 entitled ASPECTS OF A CONTROL SYSTEM OF A MINIMALLY INVASIVE SURGICAL APPARATUS, issued on Dec. 10, 2002 to Gunter D. Niemeyer, incorporated herein by reference, describes further details of limiting a robot's motion within restricted regions and/or influencing it to move along desired paths.

Virtual fixtures (VFs) may be generally classified as either forbidden region virtual fixtures (FRVFs) or guidance virtual fixtures (GVFs) (e.g., haptic guidance). FRVFs allow desired motion only in a predetermined task space, whereas GVFs provide assistance in keeping the motion on desired paths or surfaces. In this architecture, FRVFs are defined using a fixed number of virtual planes, whereas GVFs can be selected from a predefined set of primitives.

Figure 29:
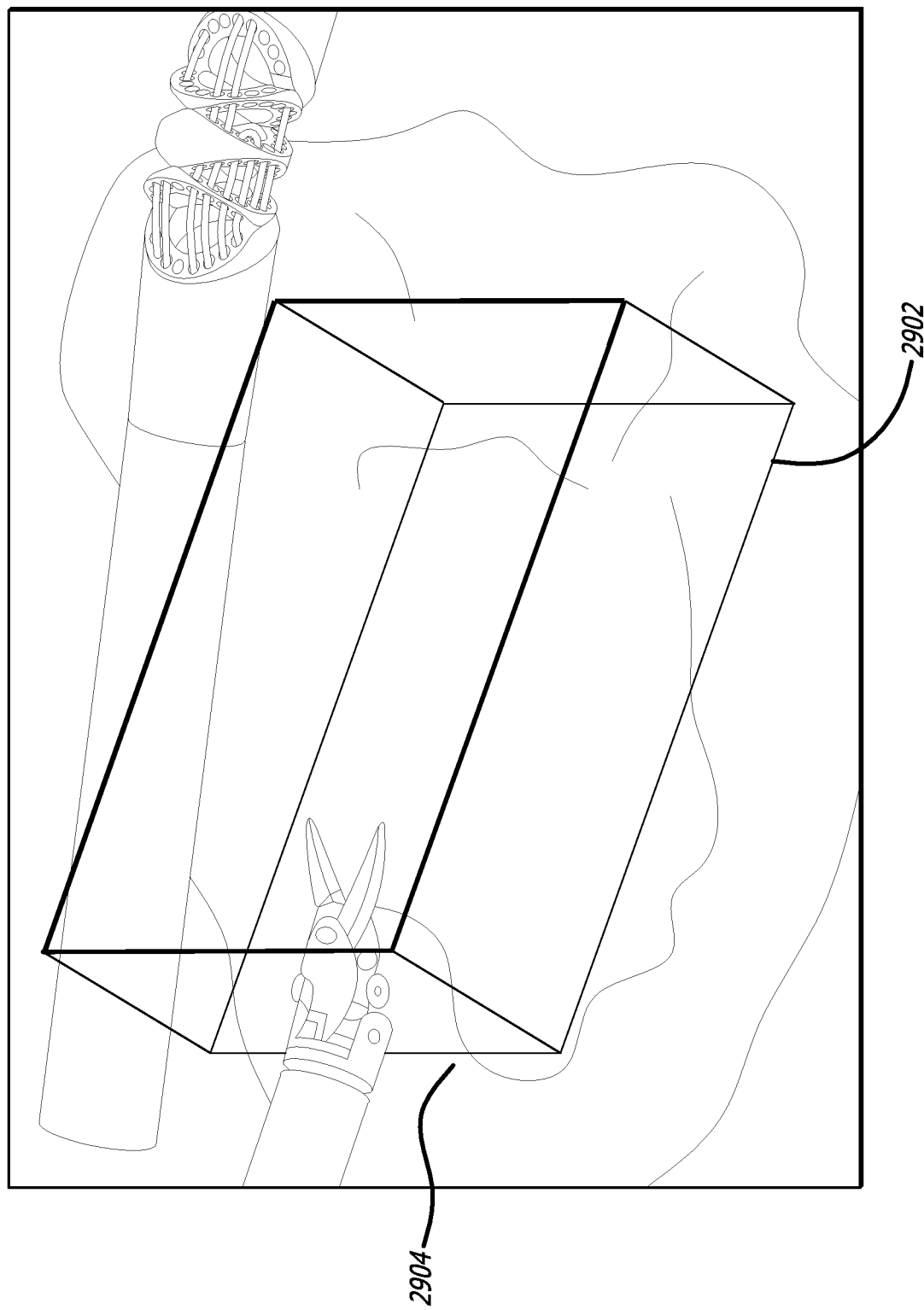
FIG. 29 is an exemplary diagrammatic view of boundaries of a virtual fixture overlaid onto the camera images of the surgical site in the 3D interface display of the surgeon console.

In FIG. 29, an exemplary virtual fixture 2902 in the shape of a bounding box is illustrated as being placed around a surgical gripper 2904. In this example of the virtual fixture 2902, the bounding box is open at the bottom allowing freedom of movement of the gripper 2904 towards the direction of the tissue. Lateral movement of the gripper 2904, as well as upward movement and forward movement of the gripper 2904, are curtailed by the sides of the bounding box in those directions. The forbidden region virtual fixtures set predefined limits on instrument movement to prevent undesired tissue collision. In another aspect, guidance virtual fixtures may be used to constrain a surgical instrument to move on a fixed trajectory. For example, a suturing trajectory may assist the surgeon to perform suturing movements along a curved path.

To enter Haptic Guidance mode the surgeon holds the MTMs steady for three seconds in order to enter masters-as-mice mode. The GUI mode becomes active and visible on the surgical console and a 3D pointer/cursor and menu system are overlaid onto the surgical console. Graphical tool icons appear at each of the PSM tools.

The surgeon moves the 3D pointer by manipulating one of the primary MTM, and selects "virtual fixture mode" by closing the primary MTM grip while the pointer is appropriately positioned on the graphical menu system. A new menu system appears on the surgeon console that allows adjustment of planes that define the boundary of forbidden regions. In this menu system, a number of 3D planes are visible to the surgeon.

By using the MTMs the surgeon can grab the available planes as previously discussed in masters-as-mice mode (See also medical image overlay, similar to adjustment of slice plane image). By moving the planes to desired locations, the surgeon may create boundaries in which robotic surgical tools will not traverse. It may be advantageous to define boundaries, especially in delicate surgeries to prevent accidental tissue destruction by sharp instruments.

Alternatively, in a GVF mode, the surgeon may choose to add fixtures to a surface plane or a predetermined path. These fixtures may be used to guide the surgical tool along the surface or path, automating certain steps and also allowing precise placement of surgical tools prior to actual cutting or shearing of tissue.

In one embodiment, context based menus may allow the surgeon to select from a list of predefined virtual fixtures listed by unique identifiers. Using this function may expedite placing boundaries and defining fixtures for routine surgeries and procedures.

After the boundaries or primitives are defined, the surgeon selects the "done" button by closing the primary MTM grip while the pointer is appropriately positioned on the graphical menu system. The surgeon releases the master clutch and returns to normal operating mode.

Modular Robotic Master/Slave Control System

In another aspect of the embodiments of the invention, the surgical assistant workstation provides a modular robotic master/slave control system. The modular robotic master/slave control system allows a single master controller (surgeon console) to be used to control two or more different types of patient-side slave manipulators (PSM). For example, in one aspect a single master control station (surgeon console) may be used to control a slave station or robot (patient side manipulator) with rigid surgical instruments (similar to the da Vinci® Surgical System instruments manufactured by Intuitive Surgical Inc.) that may be used for abdominal surgery. Alternately, the same master control station may be used to control a different slave station or robot (patient side manipulator) with flexible, snake-like surgical instruments that may be used for laryngeal surgery.

In another aspect, the master control station may be used to coincidentally control different types of slave stations (different patient side carts (PSC) with different patient-side slave manipulators (PSM)) that are coupled to it. For example, a minimally invasive surgical instrument system may comprise a master console, a first slave station, and a second slave station coupled together by the surgical assistant workstation. The robotic arm configuration of the first slave station is different from the robotic arm configuration of the second slave station such that different control signals to each are used in their control. The surgical assistant workstation adapts the master console to interchangeably control either the first slave station or the second slave station.

Conclusion

The embodiments of the invention have now been described with some detail. While certain exemplary embodiments have been described and shown in the accompanying drawings, it is to be understood that such embodiments are merely illustrative of and not restrictive on the broad invention, and that the embodiments of the invention not be limited to the specific constructions and arrangements shown and described, since various other modifications may become apparent after reading this disclosure. Instead, the embodiments of the invention should be construed according to the claims that follow below.

We claim:

1. A minimally invasive surgical system comprising:
   a stereoscopic endoscope to capture camera images of a surgical site and a first tool;
   a stereoscopic video display device of a surgeon console to display stereo video images to a user to view images with a three-dimensional (3D) appearance;
   a processor coupled to the stereoscopic endoscope and the stereoscopic video display device, in response to stored program instructions the processor is configured to
   overlay a first tool icon onto the one or more captured camera images of the surgical site, wherein the first tool icon is located adjacent the first tool without being on top of the first tool,
   receive a signal selecting the first tool icon; and
   overlay a first menu system onto the one or more captured camera images of the surgical site based on the selection of the first tool icon, the first menu system including a plurality of first menu buttons associated with the first tool to further control the first tool or provide information associated with the first tool.

2. The minimally invasive surgical system of claim 1, wherein in response to further stored program instructions the processor is further configured to
track a position of the first tool in the surgical site, and overlay the first tool icon near images of the first tool in the one or more captured camera images based on the tracking of the position of the first tool.

3. The minimally invasive surgical system of claim 2, wherein in response to further stored program instructions the processor is further configured to
adjust a size of the first tool icon in response to a change in depth of the first tool in the surgical site.

4. The minimally invasive surgical system of claim 1, further comprising
a first menu button in the first menu system configured to overlay intra-operative images captured by the first tool within an inset window onto the one or more captured camera images of the surgical site.

5. The minimally invasive surgical system of claim 1, further comprising
a second menu button in the first menu system configured to overlay intra-operative images captured by the first tool within a flashlight image window onto the one or more captured camera images of the surgical site.

6. The minimally invasive surgical system of claim 1, further comprising
images of a second tool captured by the stereoscopic endoscope;
a second tool icon overlaid onto the one or more captured camera images of the surgical site, the second tool icon located near the second tool; and
the processor overlays a second menu system onto the one or more captured camera images of the surgical site based on the selection of the second tool icon, the second menu system including a plurality of second menu buttons associated with a context of the second tool to further control the second tool or provide information associated with the second tool.

7. A surgeon console of a minimally invasive surgical system comprising:
a stereoscopic video display device to display live captured stereo camera images of a surgical site, and a first tool, with a three-dimensional (3D) appearance;
a processor coupled to the stereoscopic video display device, in response to stored program instructions the processor is configured to
overlay a first tool icon onto the one or more live captured camera images of the surgical site, wherein the first tool icon is located adjacent the first tool without being on top of the first tool,
receive a signal selecting the first tool icon; and
overlay a first menu system onto the one or more live captured camera images of the surgical site based on the selection of the first tool icon, the first menu system including a plurality of first menu buttons associated with the first tool to further control the first tool or provide information associated with the first tool.

8. The minimally invasive surgical system of claim 7, further comprising
a first menu button in the first menu system configured to overlay intra-operative images captured by the first tool within an inset window onto the one or more captured camera images of the surgical site.

9. The minimally invasive surgical system of claim 8, further comprising
a second menu button in the first menu system configured to overlay intra-operative images captured by the first tool within a flashlight image window onto the one or more captured camera images of the surgical site.

* * * * *

UNITED STATES PATENT AND TRADEMARK OFFICE
CERTIFICATE OF CORRECTION

| | |
|---|---|
| PATENT NO. | : 11,259,870 B2 |
| APPLICATION NO. | : 15/725271 |
| DATED | : March 1, 2022 |
| INVENTOR(S) | : Simon P. DiMaio et al. |

It is certified that error appears in the above-identified patent and that said Letters Patent is hereby corrected as shown below:

In the Specification

Column 1, Lines 32-34, should read:
--U.S. patent application Ser. No. 11/447,668 claims the benefit of U.S. provisional patent application Ser. No. 60/688,013 filed on June 6, 2005 by inventors Christopher J. Hasser, et al., entitled ROBOTIC ULTRASOUND PROJECT INVENTION MATERIAL.--

Signed and Sealed this
Fifth Day of July, 2022

Katherine Kelly Vidal
*Director of the United States Patent and Trademark Office*